United States Patent
Garzon

(10) Patent No.: US 11,820,782 B2
(45) Date of Patent: Nov. 21, 2023

(54) SALT FORMS OF AMINO PYRAZINE PURINE BASED SELECTIVE KINASE INHIBITOR

(71) Applicant: FTG BIO LLC, Hackensack, NJ (US)

(72) Inventor: Felix Tomas Garzon, Hackensack, NJ (US)

(73) Assignee: FTG BIO LLC, Hackensack, NJ (US)

( * ) Notice: Subject to any disclaimer, the term of this patent is extended or adjusted under 35 U.S.C. 154(b) by 25 days.

(21) Appl. No.: 16/497,109

(22) PCT Filed: Mar. 30, 2018

(86) PCT No.: PCT/IB2018/052222
§ 371 (c)(1),
(2) Date: Sep. 24, 2019

(87) PCT Pub. No.: WO2018/178944
PCT Pub. Date: Oct. 4, 2018

(65) Prior Publication Data
US 2021/0122766 A1    Apr. 29, 2021

(51) Int. Cl.
*C07D 519/00*    (2006.01)

(52) U.S. Cl.
CPC ........ *C07D 519/00* (2013.01); *C07B 2200/13* (2013.01)

(58) Field of Classification Search
CPC .... C07D 519/00; C07D 498/08; A61K 31/52; A61K 45/06
See application file for complete search history.

(56) References Cited

FOREIGN PATENT DOCUMENTS

WO    WO 2011078795    *    6/2011

OTHER PUBLICATIONS

STAHL. Handbook of Pharmaceutical Salts, 2002, pp. 280-281 (Year: 2002).*
"Prevention-Prostate Cancer", http://www.pcf.org/site/c.leJRIROrEpH/b.5802029/k.31EA/Prevention.htm, accessed Apr. 18, 2016 (Year: 2016).*
STAHL. Handbook of Pharmaceutical Salts, 2002, pp. 280-281 and 200-301. (Year: 2002).*
Cotton, Advanced Inorganic Chemistry, 1999. (Year: 1999).*
"Chembl4279073|C20H26N8O—PubChem", https://pubchem.ncbi.nlm.nih.gov/compound/53258965, create date Aug. 1, 2011, accessed Sep. 27, 2021. (Year: 2011).*
Vanhaesebroeck, B. et al. Nat. Rev. Mol. Cell. Biol. 2010, 11, 329-341.
Nahta, R. et al. Clin. Breast. Cancer, 2010, 10(Suppl 3), S72-78.
Cully, M. et al. Nat. Rev. Cancer. 2006, 6(3): 184-92.
Guertin, D, A. et al. Trends in Molecular Medicine, 2005, 11(8), 353-361.
Chiang, G, G. et al. Trends in Molecular Medicine, 2007, 13 (10), 433-442.
Jacinto and Hall. Nature Reviews Molecular and Cell Biology, 2005, 4, 117-126.
Sabatini, D. M. and Guertin, D. A. Defining the role of mTOR in Cancer. Cancer Cell, 2007, 12, 9-22.
Ciraolo, E. et al. Curr. Med. Chem. 2011, 18, 2674-2685.
Laplante, M and Sabatini, D. M. Cell, 2012,149(2), 274-93.
Yu, Y. et al. Science, 2011, 332 (6035) 1322-1326.
Lamming, D. W. et al. J. Clin. Invest. 2013, 123(3), 980-989.
Leinweber, F-J. Drug Metabolism Reviews, 1987, 18(4), 379-439.
Fenton, T. R. and Gout, I. T. International Journal of Biochemistry and Cell biology, 2011, 43(1) 47-59.
Heesom, K. J. and Denton, R. M. FEBS Letters, 1999, 457 (3), 489-493.
Zoncu, R. et al. Nature Reviews Molecular Cell Biology, 2011, 12(1), 21-35.
Brachmann, S. M. et al. PNAS (USA), 2009, 106(52), 22299-22304.
Molckovsky, A. and Siu, L. L. Journal of Hematology and Oncology, 2008, 1(1), Article 20.
Yap, T. A. et al. Current Opinion in Pharmacology, 2008, 8(4), 393-412.
Vilar, E. et al., Molecular Cancer Therapeutics, 2011 10(3), 395-403.
Janes, M. R. et al. Nature Medicine, 2010, 16(2), 205-213.
Showkat, M. et al. Molecular Biology International, 2014, Article ID 686984.
Poulsen, A. et al. J. Chem. Inf. Model, 2014, 54, 3238-3250.

\* cited by examiner

*Primary Examiner* — Noble E Jarrell
(74) *Attorney, Agent, or Firm* — MAINLINE INTELLECTUAL PROPERTY

(57) ABSTRACT

The present invention relates to amino pyrazine purine compounds that are useful as kinase inhibitors. More particularly, the present invention relates to 5-(2-(8-Oxa-3-azabicyclo[octan-3-yl)-9-(pentan-3-yl)-9H-purine-6-yl) pyrazin-2-amine compounds, including pharmaceutically acceptable salts thereof, method of preparations, pharmaceutical compositions containing these compounds and uses of these compounds in modulating phosphoinositide 3-kinase (PI3K-AKT), mammalian target of rapamycin (mTOR), DNA-PK and ATM kinase, and may be used as therapeutic agents or diagnostic probes and for the treatment of a number of proliferative conditions or disorders including tumors, cancers, hematological and lymphatic and B-malignancies, immunological and gene alterations disorders, inflammation, certain metabolic diseases, cardiovascular diseases, obesity, type 2 diabetes, anti-aging and neurological disorders.

12 Claims, 29 Drawing Sheets

SALT FORMS OF AMINO PYRAZINE PURINE BASED SELECTIVE KINASE INHIBITOR

PRIORITY PARAGRAPH

This application claims priority to the PCT application PCT/IB2018/052222 filed on 30 Mar. 2018, which claims priority to the Indian provisional application No. 201741011673, filed on Mar. 31, 2017, titled "SALT FORMS OF AMINO PYRAZINE PURINE BASED SELECTIVE KINASE INHIBITOR and are incorporated herein by reference.

TECHNICAL FIELD OF THE INVENTION

The present invention is in the technical field of amino pyrazine purine compounds that are useful as kinase inhibitors. More particularly, the present invention relates to esylate and oxalate salts of 5-(2-(8-Oxa-3-azabicyclo[octan-3-yl)-9-(pentan-3-yl)-9H-purine-6-yl)pyrazin-2-amine compound, pharmaceutically acceptable salts thereof, method of preparations, pharmaceutical compositions containing these compounds and uses of these compounds in modulating PI3K (phosphoinositide 3-kinase), AKT, mammalian target of rapamycin (mTOR), DNA-PK and Kinases, and may be used as therapeutic agents or diagnostic probes and for the treatment of a number of disorders including tumors, cancers, hematological and lymphatic malignancies, immunological disorders, gene alterations disorders, inflammation, certain metabolic diseases, cardiovascular diseases, obesity, type 2 diabetes, anti-aging and neurological disorders.

BACKGROUND OF THE INVENTION

Kinases, also known as phosphotransferases, transfer phosphate groups from high energy donor molecules to target molecules. Protein Kinases modify activity of specific proteins, involved in many cellular processes and implicated in number of medical conditions. Therefore, modulating activities of specific Kinases aid in controlling disease conditions.

The phosphatidylinositol 3-kinase (PI3K) AKT/PKB (subfamily of serine/threonine kinases) family constitutes a group of lipid kinases that convert phosphatidylinositol-4,5-bisphosphate to phosphatidylinositol-3,4,5-trisphosphate. This conversion initiates a signaling pathway crucial to many aspects of cell growth and survival, including divergent physiological processes such as cell cycle progression, differentiation, transcription, translation, and apoptosis.

Furthermore, PI3K is a crucial regulator of angiogenesis and enhanced metabolic activity in tumors. PI3K also modulates the activity of mammalian target of rapamycin (mTOR) by negative regulation of the tuberous sclerosis 1/2 (TSC1/2) complex. mTOR kinase can be activated by growth factors by cellular stresses. mTOR kinase activation plays a central role in regulating cell growth and cell survival via a wide range of cellular functions including translation, transcription, mRNA turnover, protein stability, actin cytoskeleton reorganization and autophagy.

The PI3K/AKT/mTOR pathway is the most commonly activated signaling pathway in human cancer. Dysregulation, either through multiple upstream receptor classes, amplification of PI3K, deletion of phosphatase and tensin homologue (PTEN) or activating mutations has been closely linked to the development and progression of a wide range of cancers. Researchers studying mTOR kinase biology have discovered a pathological connection between the dysregulation of mTOR cell signaling and a number of diseases including immunological disorders, cancer, hematological and lymphatic malignancies, gene alterations disorders, metabolic diseases, cardiovascular diseases, obesity, type 2 diabetes and neurological disorders.

mTOR is a serine/threonine kinase of 289 kDa that links mitogenic stimuli to cell growth and division. As mentioned mTOR is one of the important enzyme in the PI3-Akt pathway. mTOR is mammalian target of rapamycin. Rapamycin binds to FKBP12 and the complex then binds to and specifically inhibits mTOR. mTOR was also named as FKBP-RAP associated protein (FRAP), RAP FKBP12 target (RAFT1) and RAP target (RAPT1). Rapamycin inhibits the anabolic signals by mTOR that in turn responsible for organ rejection.

In humans, mTOR mediates anabolic signals from 2 sources; nutrients and activated growth factor receptors. mTOR exists as:

1. A rapamycin-sensitive complex, known to as mTOR complex 1 (mTORC1). Activation of mTOR results in increase protein translation as mTORC1 phosphorylates and activates the translation regulators eukaryotic initiation factor 4E-binding protein 1 and ribosomal p70 S6 kinase. Therefore, by inhibiting mTOR, rapamycin leads to a decrease in phosphorylation and a decrease in protein synthesis.
2. The second complex is known as mTOR complex 2 (mTORC2). mTORC2 is rapamycin-insensitive and interacts with rictor (rapamycin-insensitive companion of mTOR). mTORC2 regulates the pro-survival kinase Akt/PKB by phosphorylating it on S473. Full activation of AKT is brought together by T308 phosphorylation by PDK1 and S473 phosphorylation by mTORC2.

mTOR is also implicated in renal cell carcinoma involving hypoxia-inducible factor (HIF). With loss of Von Hippel-Lindau (VHL) gene function inhibits renal cell cancer, leading to accumulation of the oxygen-sensitive transcription factors HIF-1 and HIF-2. Accumulation of HIF-1 and HIF-2 yield hyper stimulation of vascular endothelial growth factor (VEGF), platelet-derived growth factor (PDGF), and transforming growth factor (TGF). This leads to activation of mTOR, which stimulates both a protein stabilization function and a protein translational function and increases HIF-1 activity.

mTOR Feedback Regulation: Multiple negative feedback loops regulate the mTOR pathway and various studies have shown that mTORC1 negatively affects the insulin-PI3K-AKT pathway. The insulin receptor substrate 1 (IRS1) is directly phosphorylated by S6K1 at multiple sites which impairs its function and leads to inhibitory effects on the insulin-PI3K-AKT pathway. Growth factor receptor-bound protein 10 (GRB10) is a recently discovered substrate of mTOR that is activated by mTOR phosphorylation and negatively controls insulin-PI3K-AKT signaling pathway by inhibiting the insulin receptor in its active form.

mTOR Downstream Pathway: The best-characterized downstream effectors of mTORC1 which are phosphorylated by activated mTOR kinase are S6K1 and 4E-BP1.

S6K1, the ribosomal protein S6 kinase (S6K), a serine/threonine kinase that belongs to the AGC kinase family, is an important regulator of cell growth and cell size. The S6K family consists of two genes (S6K1 and S6K2) which share an overall 70% sequence homology.

4E-BP1, which belongs to a family of three small (10-12 kda) proteins that act as inhibitors of translation initiation by binding and inactivating eIF4E (mRNA Cap binding protein), is the second well-characterized mTORC1 target. mTORC1 phosphorylates 4E-BP1 at several residues which promotes the dissociation of eIF4E from 4E-BP1 consequently mitigating the inhibitory effect of 4E-BP1 on eIF4E dependent translation initiation whereas the inhibition of mTOR by rapamycin is believed to cause 4E-BP1 dephosphorylation, which results in inhibition of protein translation.

Tuberous sclerosis complex gene products, TSC1 and TSC2 together to inhibit mTOR-mediated downstream signalling. TSC1 and TSC2 mutations show increased VEGF and activated mTOR pathways to angiogenesis.

Rapamycin, also known as sirolimus, is an antibiotic produced by *Streptomyces hygroscopicus*. It was developed initially as an anti-fungal drug directed against *Candida albicans, Cryptococcus neoformans*, and *Aspergillus fumigatus*. Later, rapamycin was developed as an immunosuppressive and an anti-cancer agent. Rapamycin also inhibits the oncogenic transformation of human cells induced by either PI3K or Akt.

The DNA-dependent protein kinase (DNA-PK) is a nuclear serine/threonine protein kinase that is activated upon association with DNA. There are sequence similarity between DNA-PKcs and PI 3-kinases. PI 3-kinase inhibitors have shown to inhibit DNA-PK.

PI3K/mTOR dual inhibitors: Dual PI3K/mTOR inhibitors were developed because of the above concerns over mTOR inhibitors. This was made possible because of the high homology that is shared by the kinase domains of PI3K and mTOR. These molecules inhibit mTORC1, mTORC2, and PI3K, thus inhibiting the phosphorylation of AKT, S6K1, and 4E-BP1, and are therefore attractive drugs for targeting cancers driven by PI3K activation. These inhibitors include XL-765, PI-103, and NVP-BEZ235 which are undergoing phase I/II clinical trials. PI-103 and NVP-BEZ235 have been found to suppress AKT as well as S6K1 in breast tumors and leukemia cells, although some studies suggest that such broad inhibition of cellular signalling may also impair growth of normal cells.

In summary, mTOR pathway plays a key role in nutrient homeostasis that regulates cellular growth and proliferation. mTOR regulates protein translation through effector molecules S6K1 and 4E-BP1. Dysregulation of the pathway is complicated by cross-talk between mTOR and other signalling pathways like AKT and PI3 kinase. Though mTOR pathway dysregulation manifests into various pathological states, it is not the only candidate responsible for the effect. Further downstream signalling is very complex that is understood by the fact that therapeutic regimens that target only mTOR are not very effective to treat cancer. Dual inhibitors that target both mTOR and PI3 kinase have shown promise in combating the disease.

Furthermore, these findings have generated intense interest in the development of small-molecule modulators of key proteins in this cascade, including the various PI3K isoforms and mTOR. The structural homology of the adenosine triphosphate (ATP) binding sites within the PIKK (phosphatidylinositol 3-kinase-related kinases) family has enabled the discovery of small molecule inhibitors with varying degrees of activity against mTOR and the isoforms of the class I PI3Ks.

Furthermore, Rapamycin, the inhibitor of mechanistic target of rapamycin (mTOR), has the strongest experimental support to date as a potential anti-aging therapeutic in mammals.

In addition, inhibition of cell growth represents a valid target for treating cancer, designing new drugs that inhibit mTOR will potentially have therapeutic value.

Thus, mTOR inhibitors have the potential to provide further biologically active compounds that have useful, improved pharmaceutical properties for the treatment of kinase related conditions or disorders.

Furthermore, there is also a need for small molecule inhibitors of related enzymes (e.g., PI3K, AKT) that functions upstream or downstream of the mTOR signaling pathway.

The compound 5-(2-(8-Oxa-3-azabicyclo[octan-3-yl)-9-(pentan-3-yl)-9H-purine-6-yl)pyrazin-2-amine (Compound I, FT1518 free base) was first described in PCT/SG2010/000474 (WO2011078795) and shows significant promise as a pharmaceutically active agent for the treatment of a number of medical conditions and clinical development of this compound is underway based on the activity profiles demonstrated by the compound.

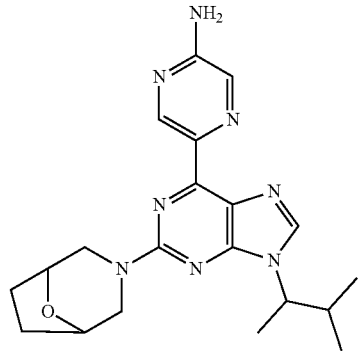

Chemical Name: 5-[2-(8-oxa-3-azabicyclo[3.2.1]octan-3-yl)-9-pentan-3-ylpurin-6-yl]pyrazin-2-amine, Molecular Formula: $C_{20}H_{26}N_8O$, Molecular Weight: 394.47.

Compound I

For formulation of pharmaceutical compositions, it is imperative that the pharmaceutically active substance can be reliably reproduced in a commercial scale and robust enough to withstand the conditions to which the pharmaceutically active substance is exposed.

Furthermore, from a manufacturing perspective, it is of high importance that the commercial manufacturing process of a pharmaceutically active substance, that the same compound is produced when the same manufacturing conditions are employed.

In addition, it is necessary that the pharmaceutically active substance exists in a solid form and minor changes in manufacturing conditions should not lead to large changes in the solid form of the pharmaceutically active substance produced.

In addition, it is necessary that the pharmaceutically active substance is stable. This is important to produce pharmaceutical formulations by incorporating pharmaceutically active ingredient. If the pharmaceutically active substance is hygroscopic ("sticky") and absorbs water over time, it becomes difficult to formulate the pharmaceutically active substance into a drug as the amount of substance in each dosage will vary greatly depending upon the degree of hydration. Furthermore, variations in hydration or solid form ("polymorphism") can change the physico-chemical properties.

In summary, for a pharmaceutical formulation, chemical stability, solid state stability, and "shelf life" of the pharmaceutically active agent are very important factors. It is desirable that the pharmaceutically active agent and any formulations containing it, must be capable of being stored over appreciable periods of time without exhibiting any physico-chemical characteristics change, such as its activity, moisture content, solubility characteristics, solid form and thereof.

In relation to 5-(2-(8-Oxa-3-azabicyclo[octan-3-yl)-9-(pentan-3-yl)-9H-purine-6-yl)pyrazin-2-amine, initial studies were carried out on the hydrochloride salt and indicated that polymorphism was prevalent, with the compound being found to adopt more than one crystalline form depending upon the manufacturing conditions. In addition, it was observed that the ratio of the polymorphs varied from batch to batch even when the manufacturing conditions remained constant. These batch-to-batch inconsistencies made the hydrochloride salt less desirable from a commercial viewpoint.

Accordingly, it would be desirable to develop salts of 5-(2-(8-Oxa-3-azabicyclo[octan-3-yl)-9-(pentan-3-yl)-9H-purine-6-yl)pyrazin-2-amine which overcome or improve one or more of the above identified problems.

In summary, there is an urgent need in the art to develop salts of 5-(2-(8-Oxa-3-azabicyclo[octan-3-yl)-9-(pentan-3-yl)-9H-purine-6-yl)pyrazin-2-amine small molecule inhibitors of mTOR (including mTORC1 and mTORC2) and/or PI3K and/or DNA-PK that can be used to treat diseases such as, wide range of cancers, hematological and lymphatic malignancies, and related hyper proliferative disorders, immunological, gene laterations disorders, inflammation, certain metabolic diseases, cardiovascular diseases, obesity, type 2 diabetes, anti-aging therapeutics and neurological disorders in animals and in humans.

SUMMARY OF THE INVENTION

According to an exemplary aspect, the present invention discloses amino pyrazine purine compounds that are useful as kinase inhibitors. More particularly, the present invention relates to 5-(2-(8-Oxa-3-azabicyclo[octan-3-yl)-9-(pentan-3-yl)-9H-purine-6-yl)pyrazin-2-amine compounds, including pharmaceutically acceptable salts thereof, method of preparations, pharmaceutical compositions containing these compounds and uses of these compounds in modulating phosphoinositide 3-kinase (PI3K/AKT), mammalian target of rapamycin (mTOR), DNA-PK and ATM kinase, and may be used as therapeutic agents or diagnostic probes and for the treatment of a number of proliferative conditions or disorders including tumors, cancers, hematological and lymphatic malignancies, immunological and gene alterations disorders, inflammation, certain metabolic diseases, cardiovascular diseases, obesity, type 2 diabetes and neurological disorders and regulation of the aging process.

In one embodiment, the present invention discloses oxalate and esylate of compound 5-(2-(8-Oxa-3-azabicyclo [octan-3-yl)-9-(pentan-3-yl)-9H-purine-6-yl)pyrazin-2-amine (FT1518 free base, initial precursor).

According to an exemplary aspect, the present invention deals with various salt screening experiments that were explored using acidic counterions to evaluate the salt forming affinity/propensity of FT-1518.

According to further exemplary aspect, the present invention deals with the salt formation and was confirmed primarily by PXRD and proton NMR. The results and observations of salt screening trials showed that there was feasibility of formation of tosylate, adipate, mesylate, malate, phthalate, fumarate, succinate, oxalate, maleate, nitrate, tartarate, malonate, camphor sulfonate, esylate, besylate, sulphate, and hydrochoride salts. Preparation of salts such as esylate, besylate, HCl, sulfonate, nitrate can be done by using precipitation from common solvent (here Tetrahydrofuran). Preparation of remaining salts among the confirmed can be prepared by solvent evaporation (slow) in a common solvent (acetone).

In one embodiment, the present invention deals with the solubility of salt in 10 mM potassium dihydrogen phosphate buffer (pH 6.8) & % purity (HPLC), crystallinity (PXRD), proton NMR, hygroscopicity & pseudopolymorph propensity (Dynamic Vapour Sorption), melting point & thermal events (DSC), % weight loss before melting point maximum up to 150° C. (TGA) was conducted to completely characterize the salt. This compilation of characterization of all the salts was used for primary salt selection for polymorph screening and stability studies.

In one embodiment, the present invention discloses physical form screening of selected salts (esylate and oxalate salts) the polymorph screening of the FT-1518 esylate and oxalate confirmed that there are few new physical forms identified in the experiments.

In one particular embodiment, FT-1518 esylate formed majorly three forms, form-1, form-2 and form-3. Based on the stability study, form-1 of FT-1518 esylate can be confirmed as most commonly existing physical form. Form-2 obtained from solvents (ethyl acetate and DCM) except ethanol and form-3 converted back to the initial salt form that is form-1 when exposed to heat and humidity at 40° C./75% RH for 7 days. Only form-2 obtained from cooling crystallization in ethanol remained same after stability study.

In one additional embodiment, the pharmaceutically active compositions containing the acceptable salts are having chemical stability, solid state stability, "shelf life" of the pharmaceutically active agent without exhibiting no physico-chemical characteristics change, such as its activity, moisture content, solubility characteristics, solid form and thereof that are devoid of the inconsistencies associated with existing hydrochloride salt forms of the 5-(2-(8-Oxa-3-azabicyclo[octan-3-yl)-9-(pentan-3-yl)-9Hpurine-6-yl) pyrazin-2-amine.

In one particular embodiment, the pharmacokinetic studies on the efficacy of the salts are done in vivo and in vitro by studying cell cytotoxicity, microsomal stability, Caco-2 permeability, plasma protein binding, intravenous and per oral pharmacokinetic profile of FT1518 (base); FT1518-Esylate salt and FT1518-Oxalate salt in male Sprague Dawley (SD) Rats and male Balb/c mice, anti-proliferative activity of FT-1518 in cancer cell lines.

In yet another embodiment, the esylate form of 5-(2-(8-Oxa-3-azabicyclo[octan-3-yl)-9-(pentan-3-yl)-9Hpurine-6-yl)pyrazin-2-amine found as potent inhibitor of cell growth in breast cancer (MCF-7), colon cancer (HCT-16) and prostate cancer (PC-3) cells compared to base and oxalate salt form.

In an additional embodiment, 5-(2-(8-Oxa-3-azabicyclo [Octan-3-yl)-9-(pentan-3-yl)-9Hpurine-6-yl)pyrazin-2-amine and its preferred salt forms as per the bacterial reverse mutation assay and FT 1518 base and salt forms showing stability in human, rat and dog microsomes.

In yet another embodiment, FT-1518 oxalate salt was identified and isolated as 4 physical forms, which were named as form-A, form-B, form-C and form-D. Many of these forms converted back to the initial salt form that is form-A during the stability study when exposed to heat and humidity at 40° C./75% RH for 7 days. Only form-D obtained from ethyl acetate:water (9:1) slurries remained same during this period.

In yet another embodiment, suitable physical forms of esylate and oxalate salts of FT1518 were selected.

Based on the stability studies of various physical forms of both salts and various crystallization processes in solvents of different polarity (ranging from non-polar to polar) of the physical forms of the both salts (esylate and oxalate of FT-1518), Form-1 (pattern-1) of esylate and form-A of oxalate seemed to be most occurring and stable forms.

In some embodiments the salts are crystalline.

In some embodiments the salt is the 1:1.125 Esylate salt (ratio of drug:counterion).

In some embodiments the salt is the 1:1.125 oxalate salt (ratio of drug:counterion).

In some embodiments the esylate salt also showed clear X-ray diffraction peaks on the 2theta scale values.

In some embodiments the 1H NMR of esylate salt trial (using THF) showed major peaks at 2.111, 1.998 and 1.981.

In some embodiments the oxalate salt also showed clear X-ray diffraction peaks on the 2theta scale values.

In some embodiments the 1H NMR of oxalate salt trial (using THF) showed major peak at 2.0085.

In yet another embodiment, FT-1518 ESYLATE: The PXRD of FT-1518 Esylate salt showed characteristic diffraction pattern. DSC thermogram showed slight broader endotherm at less than 100° C. (only residual solvent after recrystallization, which can be removed in process development), followed by two sharp endotherms at 231 and 246° C. TGA showed 0.915% weight loss up to 125° C. indicating no solvate or hydrate form.

| Esylate_Methanol | DSC: Endotherm - 259.85° C. (sharp) Followed by degradation | TGA: 0.8229% up to 125° C. |

In yet another embodiment, FT-1518 OXALATE: The PXRD of FT-1518 oxalate salt showed characteristic diffraction pattern different from that of Esylate salt. The DSC thermogram showed one endotherm at around 117° C. followed by degradation indicating endotherm. TGA data showed weight loss of about 0.44% by weight when heated up to 125° C.

According to a further exemplary aspect of the present invention, stability study of physical forms of FT-1518 salts: FT-1518 Esylate salt showed very less risk of polymorphism based on experiments performed to understand the polymorphism risk and its effect on the stability. Ft-1518 oxalate salt showed few polymorphs or physical forms when recrystallized in various solvents using various crystallization techniques. But, only in ethyl acetate:water (9:1) slurry, the new physical form persisted even after stability study at 40° C./75% RH.

The present invention also provides a pharmaceutical composition comprising salts as described above.

In an exemplary embodiment, the present invention describes a method of inhibiting a protein kinase, the method including exposing the protein kinase or a fragment or complex thereof or a functional equivalent thereof and/or co-factor(s) thereof to an effective amount of a pharmaceutically acceptable salts of amino pyrazine purine compounds.

In a further exemplary embodiment of the present invention describes a method of treating or preventing a condition in a mammal in which inhibition of one or more protein kinase(s) or a fragment or a complex thereof or a functional equivalent thereof, prevents, inhibits or ameliorates a pathology or a symptomology of the condition, the method including administration of as therapeutically effective amount of a pharmaceutically acceptable salts of amino pyrazine purine compounds.

In one embodiment of the present invention describes a method of treating a disease condition wherein the condition is selected from the group consisting of inflammation, rheumatoid arthritis, psoriasis, atherosclerosis, colitis, inflammatory bowel disease, pancreatitis, multiple sclerosis, autoimmune disorders, lupus, allergic encephalomyelitis, transplant rejection, endometriosis, leiomyoma, polycystic ovarian syndrome, hamartoma, tuberous sclerosis, Alzheimer's disease, Huntington's disease, Parkinson's disease, insulin-dependent diabetes mellitus, obesity, diabetic retinopathy, cardiac hypertrophy, and autosomal dominant polycystic kidney disease.

Yet another exemplary embodiment of the present invention describes hyperproliferative diseases wherein the hyperproliferative diseases include cancers and tumors such as adrenocortical adenoma, adrenocortical carcinoma, neuroblastoma, pheochromocytoma, osteoma, osteoid osteoma, osteochondroma, osteoblastoma, enchondroma, giant cell tumor of bone, aneurysmal bone cyst, fibrous dysplasia of bone, osteosarcoma, chondrosarcoma, Ewing's sarcoma, fibrosarcoma, gliomas, meningiomas, pituitary adenomas and nerve sheath tumors, preferably anaplastic astrocytoma, astrocytoma, central neurocytoma, choroid plexus carcinoma, choroid plexus papilloma, choroid plexus tumor, dysembryoplastic neuroepithelial tumour, ependymal tumor, fibrillary astrocytoma, giant-cell glioblastoma, glioblastoma multiforme (GBM), gliomatosis cerebri, gliosarcoma, hemangiopericytoma, medulloblastoma, medulloepithelioma, meningeal carcinomatosis, neuroblastoma, neurocytoma, oligoastrocytoma, oligodendroglioma, optic nerve sheath meningioma, pediatric ependymoma, pilocytic astrocytoma, pinealoblastoma, pineocytoma, pleomorphic anaplastic neuroblastoma, pleomorphic xanthoastrocytoma, primary central nervous system lymphoma, sphenoid wing meningioma, subependymal giant cell astrocytoma, subependymoma, trilateral retinoblastoma, carcinomas of pancreas, liver, breast, prostrate, cancers and tumour of testicular, ovarian, intestinal, gastric, uterine, endometrioid, neck, throat, bladder, vulval origin, blood cancers, leukemias, lymph cancer, B-cell malignancies, Waldenström's macroglobulinemia, multiple myeloma, lung cancers, kidney cancers, cervical cancer, colon and rectal cancers, skin cancers, melanomas, and various other cancers wherein the combined modulation of PI3K and mTOR mechanism would bring about remarkable improvement and therapeutic efficiency in various non-limiting examples.

Yet another exemplary embodiment of the present invention describes the pharmaceutical compositions and the salts wherein the pharmaceutical compositions and the salts can be in various forms such as combination, alone, with excipients, diluents, carriers, humectants, capsules, tablets, injectables (intravenous, muscular, hypodermal), oral, topical, in combination with polynucleotides, other biologicals, for targeted delivery, powders, suspensions, gels, hydrogels, logenzes, in combination with cryo, radiation therapies, binders, for curing, palliative care in humans, animals and such other organism wherein the pharmaceutical compositions and the salts can be employed to relieve them of the various ailments that can be controlled by modulating the PI3K and/or mTOR pathways.

The present invention also describes neurological disorders wherein neurological disorders include Alzheimer's disease, Parkinson's, Huntington and Pick's, diseases, cognitive disorders and epilepsy inflammatory diseases include irritable bowel syndrome, ulcerative colitis, Crohn's disease, Rheumatoid arthritis, Psoriasis but not limited to these alone.

Yet another exemplary embodiment of the present invention deals with use of a compound in the preparation of a medicament for treating a condition in an animal in which inhibition of one or more protein kinase(s) or a fragment or a complex thereof or a functional equivalent thereof, prevents, inhibits or ameliorates a pathology or a symptomology of the condition.

In another embodiment of the present invention provides a method of treating or preventing medical conditions comprising administration of a therapeutically effective amount of a salt of the invention to a patient in need thereof. In some embodiments the medical conditions are cancers and related hyper proliferative disorders, immunological disorders, inflammation, certain metabolic diseases, cardiovascular diseases, obesity, type 2 diabetes, neurological disorders and antiaging In one embodiment the present invention provides the use of a salt of the invention in the treatment of medical conditions. In some embodiments the medical conditions are cancers and related hyper proliferative disorders, immunological disorders, inflammation, certain metabolic diseases, cardiovascular diseases, obesity, type 2 diabetes and neurological disorders.

In one additional embodiment the present invention provides the use of a salt of the invention in the manufacture of a medicament for the treatment of medical conditions. In some embodiments the medical conditions are cancers and related hyper proliferative disorders, immunological disorders, inflammation, certain metabolic diseases, cardiovascular diseases, obesity, type 2 diabetes and neurological disorders.

In summary, the present invention deals with amino pyrazine purine compounds that are useful as kinase inhibitors. More particularly, the present invention relates to oxalate and esylate salts of Compound 5-(2-(8-Oxa-3-azabicyclo[octan-3-yl)-9-(pentan-3-yl)-9H-purine-6-yl)pyrazin-2-amine (FT1518 free base, initial precursor), including pharmaceutically acceptable salts thereof, method of preparations, pharmaceutical compositions containing these compounds and uses of these compounds in modulating phosphoinositide 3-kinase (PI3K/AKT), mammalian target of rapamycin (mTOR), DNA-PK and Kinases, and may be used as therapeutic agents or diagnostic probes and for the treatment of a number of proliferative conditions or disorders including tumors, cancers, immunological disorders, inflammation, certain metabolic diseases, cardiovascular diseases, obesity, type 2 diabetes and neurological disorders.

Several aspects of the invention are described below with reference to examples for illustration. However, one skilled in the relevant art will recognize that the invention can be practiced without one or more of the specific details or with other methods, components, materials and so forth. In other instances, well-known structures, materials, or operations are not shown in detail to avoid obscuring the features of the invention. Furthermore, the features/aspects described can be practiced in various combinations, though only some of the combinations are described herein for conciseness.

BRIEF DESCRIPTION OF THE FIGURES

In the drawings, like reference numbers generally indicate identical, functionally similar, and/or structurally similar elements. The drawing in which an element first appears is indicated by the leftmost digit(s) in the corresponding reference number.

DETAILED DESCRIPTION OF THE INVENTION

Figure 1:
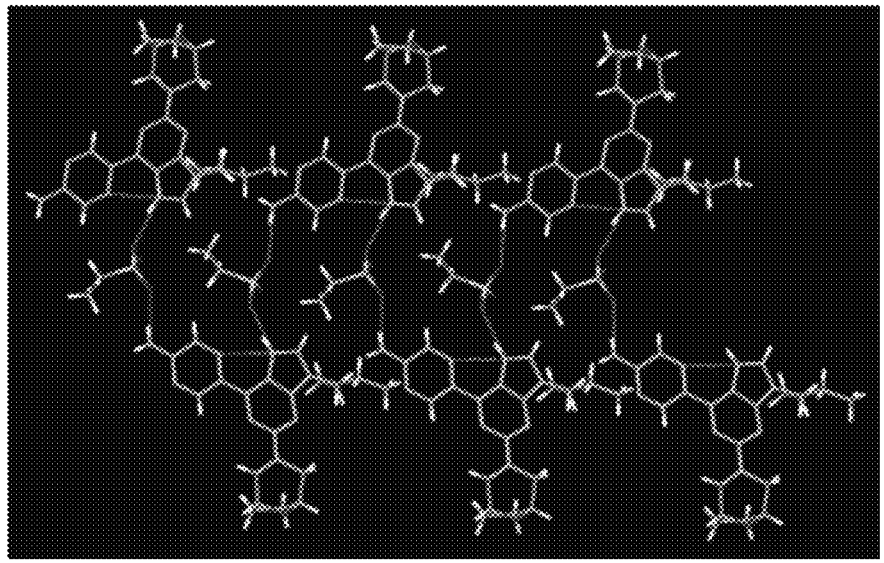
FIG. 1 depicts the FS00067855 cation . . . esylate anion, existed in the crystal lattice though N—H . . . O and extended in 1d lattice through N—H . . . O interaction according to an embodiment.

It is to be understood that the present disclosure is not limited in its application to the details of construction and the arrangement of components set forth in the following description or illustrated in the drawings. The present disclosure is capable of other embodiments and of being practiced or of being carried out in various ways. Also, it is to be understood that the phraseology and terminology used herein is for the purpose of description and should not be regarded as limiting.

The use of "including", "comprising" or "having" and variations thereof herein is meant to encompass the items listed thereafter and equivalents thereof as well as additional items. The terms "a" and "an" herein do not denote a limitation of quantity, but rather denote the presence of at least one of the referenced item. Further, the use of terms "first", "second", and "third", and the like, herein do not denote any order, quantity, or importance, but rather are used to distinguish one element from another.

As used herein, the singular forms "a", "an", and "the" include both singular and plural referents unless the context clearly dictates otherwise. By way of example, "a dosage" refers to one or more than one dosage.

The terms "comprising", "comprises" and "comprised of" as used herein are synonymous with "including", "includes" or "containing", "contains", and are inclusive or open-ended and do not exclude additional, non-recited members, elements or method steps.

All documents cited in the present specification are hereby incorporated by reference in their totality. In particular, the teachings of all documents herein specifically referred to are incorporated by reference.

Example embodiments of the present invention are described with reference to the accompanying figures.

In the drawings, like reference numbers generally indicate identical, functionally similar, and/or structurally similar elements. The drawing in which an element first appears is indicated by the leftmost digit(s) in the corresponding reference number.

Definitions

The following terms are used as defined below throughout this application, unless otherwise indicated.

The terms "tumor" or "tumor tissue" refer to an abnormal mass of tissue which results from uncontrolled cell division. A tumor or tumor tissue comprises "tumor cells" which are neoplastic cells with anomalous growth properties and no functional bodily function. Tumors, tumor cells and tumor tissue can be benign or malignant.

The phrase "differentially present" refers to differences in the quantity of the marker present in a sample taken from patients as compared to a control subject. A biomarker can be differentially present in terms of frequency, quantity or both.

"Diagnostic" means identifying a pathologic condition.

The terms "detection", "detecting" and the like, may be used in the context of detecting markers or biomarkers.

A "test amount" of a marker refers to an amount of a marker present in a sample being tested. A test amount can be either in absolute amount (e.g., µg/ml) or a relative amount (e.g., relative intensity of signals).

The terms "polypeptide," "peptide" and "protein" are used interchangeably herein to refer to a polymer of amino acid residues. "Polypeptide," "peptide" and "protein" can be modified, e.g., by the addition of carbohydrate residues to form glycoproteins.

The terms "subject", "patient" or "individual" generally refer to a human or mammals. "Sample" refers to a polynucleotides, antibodies fragments, polypeptides, peptides, genomic DNA, RNA, or cDNA, polypeptides, a cell, a tissue, and derivatives thereof may comprise a bodily fluid or a soluble cell preparation, or culture media, a chromosome, an organelle, or membrane isolated or extracted from a cell.

As used herein, "pharmaceutically acceptable salts" refers to salts that retain the desired biological activity of the above-identified compounds, and include pharmaceutically acceptable acid addition salts and base addition salts. Suitable pharmaceutically acceptable acid addition salts of compounds of Formula (I) may be prepared from an inorganic acid or from an organic acid. For example, inorganic acids are hydrochloric, sulfuric, and phosphoric acid. Appropriate organic acids may be selected from aliphatic, cycloaliphatic, aromatic, heterocyclic carboxylic and sulfonic classes of organic acids, examples of which are formic, acetic, propionic, succinic, glycolic, gluconic, lactic, malic, tartaric, citric, fumaric, maleic, alkyl sulfonic, arylsulfonic. In the case of agents that are solids, it is understood by those skilled in the art that the inventive compounds, agents and salts may exist in different crystalline or polymorphic forms, all of which are intended to be within the scope of the present invention and specified formulae.

As used herein, "Prodrug" means a compound that undergoes conversion within a biological system, usually by metabolic means (e.g. by hydrolysis, reduction or oxidation). For example an ester prodrug of a compound of formula (I) containing a hydroxyl group may be convertible by hydrolysis in vivo to the parent molecule.

As used herein, "therapeutically effective amount" or "effective amount" is an amount sufficient to effect beneficial or desired clinical results. An effective amount can be administered in one or more administrations. An effective amount is typically sufficient to ameliorate, stabilize, reverse, palliate, slow or delay the progression of the disease state.

As used herein, "functional equivalent" is means variants of the specific protein kinase species described herein. Furthermore, kinases may have isoforms, such that while the primary, secondary, tertiary or quaternary structure of a given kinase isoform is different to the prototypical kinase, the molecule maintains biological activity as a protein kinase. Isoforms may arise from normal allelic variation within a population and include mutations such as amino acid substitution, addition, truncation, deletion, or duplication. In addition, "functional equivalent" may also include variants generated at the level of transcription. Other functional equivalents may include kinases having altered post-translational modification.

Administration of said compounds to humans or animals can be by any of the accepted modes for enteral administration such as oral or rectal, or by parenteral administration such as subcutaneous, intramuscular, intravenous and intradermal routes. Injection can be bolus or via constant or intermittent infusion. The active compound is included in a pharmaceutically acceptable carrier or diluent and in an amount sufficient to deliver to the patient a therapeutically effective dose.

The compounds can be administered in any form or mode which makes the compound bioavailable. One skilled in the art of preparing formulations can readily select the proper form and mode of administration depending upon the particular characteristics of the compound selected, the stage of the condition to be treated, the condition to be treated, and other relevant circumstances.

The present disclosure also provides a pharmaceutical pack or kit comprising one or more containers filled with one or more of the ingredients of the pharmaceutical compositions. In such a pack or kit can be found a container having a unit dosage or more of the pharmaceutically acceptable compound (s). The kits can include a composition comprising an effective dosage of the compound either as concentrates (including lyophilized compositions), wherein the concentrates can be diluted further prior to use or they can be provided at the concentration of use, where the vials may include one or more dosages. Furthermore, in kits, single dosages can be provided in sterile vials so that the physician can employ the vials directly, where the vials will have the required amount and concentration of the compound(s). In addition, along with such container(s) can be written materials such as instruction manuals for use, or a notice as prescribed by a governmental agency regulating the manufacture, use or sale of pharmaceuticals or biological products, which notice reflects approval by the agency of manufacture, use or sale for human or animal administration.

The compounds may be used or administered in combination with one or more additional drug(s) for the treatment of the disorder/diseases mentioned. The components can be administered in the same formulation or in different formulations. If administered in different formulations, the compounds may be administered sequentially or simultaneously with the other drug(s). When administered in combination with one or more additional drugs, the compounds may be used in a combination therapy. Therefore, one or more of the compounds may be administered either simultaneously (as a combined preparation) or sequentially to provide a desired effect. This is particularly desirable where the therapeutic effect of each compound is different and the combined effect of the two drugs provides an improved therapeutic result.

Pharmaceutical compositions of the present teaching for parenteral injection comprise pharmaceutically acceptable sterile aqueous or nonaqueous solutions, dispersions, suspensions or emulsions as well as sterile powders for reconstitution into sterile injectable solutions or dispersions just prior to use. For examples, suitable aqueous and nonaqueous carriers, diluents, solvents or vehicles include water, ethanol, polyols (such as propylene, glycol, glycerol, polyethylene glycol, and the like), and suitable mixtures thereof, vegetable oils, and injectable organic esters such as ethyl oleate. Proper fluidity of the pharmaceutical compositions can be maintained by the use of coating materials (for example, lecithin), by the maintenance of the required particle size in the case of dispersions, and by the use of surfactants.

These compositions may also contain adjuvants such as preservative, wetting agents, emulsifying agents, and dispersing agents. Prevention of the action of micro-organisms may be ensured by the inclusion of various antibacterial and antifungal agents, for example, paraben, chlorobutanol, phenol sorbic acid, and the like. it may also be desirable to include isotonic agents such as sugars, sodium chloride, and the like. Prolonged absorption oldie injectable pharmaceutical form may be brought about by the inclusion of agents that delay absorption such as aluminium monostearate and gelatin.

If required, and for more effective distribution, the compounds can be incorporated into slow release or targeted delivery systems such as polymer matrices, liposomes, nano particles, and microspheres.

The injectable formulations can be sterilized, for example, by filtration through a bacterial-retaining filter, or by incorporating sterilizing agents in the form of sterile solid compositions that can be dissolved or dispersed in sterile water or other sterile injectable medium just prior to use.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner.

Liquid dosage forms for oral administration include pharmaceutically acceptable emulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethyl formamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof.

Besides inert diluents, the oral compositions can also include adjuvants such as wetting agents, emulsifying and suspending agents, sweetening, flavoring, and perfuming agents.

Suspensions, in addition to the active compounds, may contain suspending agents as, for example, ethoxylated isostearyl alcohols, polyoxyethylene sorbitol and sorbitan esters, microcrystalline cellulose, aluminium metahydroxide, bentonite, agar-agar, and tragacanth, and mixtures thereof.

Compositions for rectal or vaginal administration are preferably suppositories which can be prepared by mixing the compounds of this invention with suitable non-irritating excipients or carriers such as cocoa butter, polyethylene glycol or a suppository wax which are solid at room temperature but liquid at body temperature and therefore melt in the rectum or vaginal cavity and release the active compound.

Dosage forms for topical administration of a compound of this invention include powders, patches, sprays, ointments and inhalants. The active compound is mixed under sterile conditions with a pharmaceutically acceptable carrier and any needed preservatives, buffers, or propellants which may be required.

The amount of compound administered will preferably treat and reduce or alleviate the condition. A therapeutically effective amount can be readily determined by an attending diagnostician by the use of conventional techniques and by observing results obtained under analogous circumstances. In determining the therapeutically effective amount a number of factors are to be considered including but not limited to, the species of animal, its size, age and general health, the specific condition involved, the severity of the condition, the response of the patient to treatment, the particular compound administered, the mode of administration, the bioavailability of the preparation administered, the dose regime selected, the use of other medications and other relevant circumstances.

Experimental Embodiments

The compound FT-1518 was crystalline in nature and was found to be non-hygroscopic in normal room temperature conditions. The crystalline form of this drug substance was subjected for salt screening study using various approaches and then evaluated for confirmation of salt formation.

The compound is freely soluble in dimethyl sulphoxide, N, N-dimethyl acetamide, N-methyl pyrrolidone, ethanol, dichloromethane, methanol, 1,4-dioxane, Tetrahydrofuran, acetone, isopropyl alcohol; soluble in ethyl acetate, acetonitrile, toluene and isopropyl acetate, 0.11N HCl; slightly soluble in methyl tertiary butyl ether; and insoluble in diethyl ether, n-hexane, n-heptane and purified water.

Acidic counterions were selected based on pKa (basic) value of the compound around 1.70 and 4.07 to perform salt screening. Many experiments were conducted based on various approaches of salt screening such as precipitation, solvent evaporation, and anti-solvent precipitation techniques. Salt formation was confirmed using analytical techniques such as powder XRD and proton NMR. The results and observations of salt screening trials confirmed the possibility of formation of tosylate, adipate, mesylate, malate, phthalate, fumarate, succinate, oxalate, maleate, nitrate, tartarate, malonate, camphor sulfonate, esylate, besylate, sulphate, and hydrochloride salts.

The oxalate, mesylate, esylate and maleate salts are considered for further evaluation based on solubility in pH 6.8 buffer. Based on improved solubility by many folds and the pH of the 2% w/v aqueous solutions of the short listed salts of FT-1518, esylate and oxalate salts of FT-1518 were selected for further screening of physical forms and form selection. Between esylate and oxalate salts, one of the salt will be selected based on physicochemical and pharmacokinetic properties (already being conducted by FTG).

The FT-1518 esylate and oxalate salts were crystalline in nature and were found to be non-hygroscopic at ambient conditions. The crystalline forms of these salts were subjected for physical form screening studies employing various crystallization conditions and solution mediated conditions for physical form screening and then evaluated for any physical form change during these experiments.

The polymorph screening of the FT-1518 esylate and oxalate identified new physical forms existence. The salts identified depicted higher solubility in aqueous media compared to in organic solvents.

FT-1518 esylate salt demonstrated the presence of form-1 (as assigned) in majority of the solvents employed for recrystallizations. Form-1 was formed in solvents during solvent evaporation from THF, acetone, ethanol, acetonitrile, methanol, THF:water (9:1); slurry experiments in THF, Toluene, and THF:toluene (1:1). It also existed in two other forms, form-2 and form-3. Form-2 was obtained in ethyl acetate (slurry at 25° C. and 40° C.), dichloromethane and ethanol (cooling crystallization). Whereas, form-3 was obtained in methanol (cooling crystallization). Based on the stability studies, form-1 of FT-1518 esylate was concluded as most commonly occurring physical form while forms 2 3 got converted back to the initial salt form 1 when exposed to heat and humidity (40° C./75% RH) for a period of 7 days. Form-2 obtained from cooling crystallization in ethanol remained same after stability study.

FT-1518 oxalate salt was identified and isolated as 4 physical forms, which were named as form-A, form-B, form-C and form-D. FT-1518 oxalate showed form-A in majority of the solvents for recrystallization using various methods. Form-A was isolated when recrystallization of compound was done in acetone, acetonitrile, ethanol and THF using solvent evaporation (slow) method; ethyl acetate and n-hexane using slurry methods; in acetonitrile and Tetrahydrofuran using cooling crystallization. Form-B was isolated only when recrystallized in 1, 4-dioxane using solvent evaporation method. Form-C was isolated only in methanol in both solvent evaporation and cooling crystallization techniques. Form-D was isolated only in ethyl acetate and water (9:1) slurry methods. All forms except form-D obtained from ethyl acetate:water (9:1) slurries converted back to form-A during the stability study when exposed to heat and humidity at 40° C./75% RH for 7 days.

Characterization Methods

Thermal Analysis by TGA (Make: TA Instruments, Model: Q5000)

Thermo gravimetric analysis (TGA) was conducted on a TA Instruments Q500 instrument. A sample size of approximately 5-10 mg was used in a standard aluminium pan. The sample was heated at 10° C./min from ambient temperature to 300° C. under dry nitrogen at 25 mL/min.

Thermal Analysis by DSC (Make: TA Instruments, Model: Q2000)

Differential scanning calorimetry (DSC) analysis was conducted on a TA Instruments Q2000 instrument. A sample size of approximately 3-5 mg was weighed out into a standard aluminium DSC pan; the pan was hermetically sealed with a pin hole. The sample was heated at 10° C./min from ambient temperature to 300° C. under dry nitrogen at 50 mL/min. In case of disturbances occurring due to the volatile liquids or gases, open pan analysis will be done.

pXRD (Make: Bruker, Model: D8 Advance)

X-ray powder diffraction data were obtained using a Bruker D8 Advance diffractometer equipped with a 90 position auto-changer rotating sample stage and LYNXEYE detector. The radiation was CuKα (1.541'8 Å) with the voltage and current of 40 kV and 40 mA, respectively. Data was collected at room temperature from 2.000° to 40.00° 2θ; step size was 0.02° and step time 0.2s. The diffracted beam equipped with 0.23 soller slit programmable divergent (0.3°) and anti-scattering (3.96°) slits and a 0.02 mm nickel filter. Samples were prepared on a zero-background sample holder and the stage was rotated with a revolution time of 15 rotations per minute.

Solubility Determination and Chemical Purity Determination by HPLC

The below given parameters were used for HPLC analysis of FT-1518 and its salts for solubility and chemical purity determination.

TABLE A

| List of equipments | |
|---|---|
| Column | Inertsil ODS 3v, 250 × 4.6 mm, 5µ |
| Column temperature | 25° C. |
| Detector wavelength | 240 nm |
| Gradient elution (time/% mobile phase-B) | 0/20, 5/20, 15/80, 20/80, 25/20, 30/20 |
| Flow rate | 1.0 mL/min |
| Injection volume | 10 µL |
| Run time | 30 minutes |
| Mobile phase A | 0.01M KH2PO4 buffer |
| Mobile phase B | Acetonitrile |
| Sample preparation | 0.5 mg/mL |
| Diluent | Water: acetonitrile (50:50) |

Dynamic/Gravimetric Vapor Sorption (DVS) Analysis

Sorption isotherms were obtained using a VTI-SA+- moisture sorption analyzer from TA instruments. The sample temperature was maintained at 25° C. by the instrument controls. The humidity was controlled by mixing the streams of dry and wet nitrogen, with a total flow rate of 200 mL/minute. The weight change of the sample as a function of % RH was constantly monitored by microbalance.

Typically, 5 to 20 mg of the sample was weighed under ambient conditions in a tared mesh stainless steel basket. The sample was loaded and unloaded at 40% RH and 25° C. A moisture sorption isotherm was performed as outlined. The standard isotherm was performed at 25° C. at 10% RH intervals over a 0 to 90% RH range. Sample was dried at 40° C. from ambient room conditions to 0% RH.

Characterization

Characterization of Crystalline Form

Figure 9:
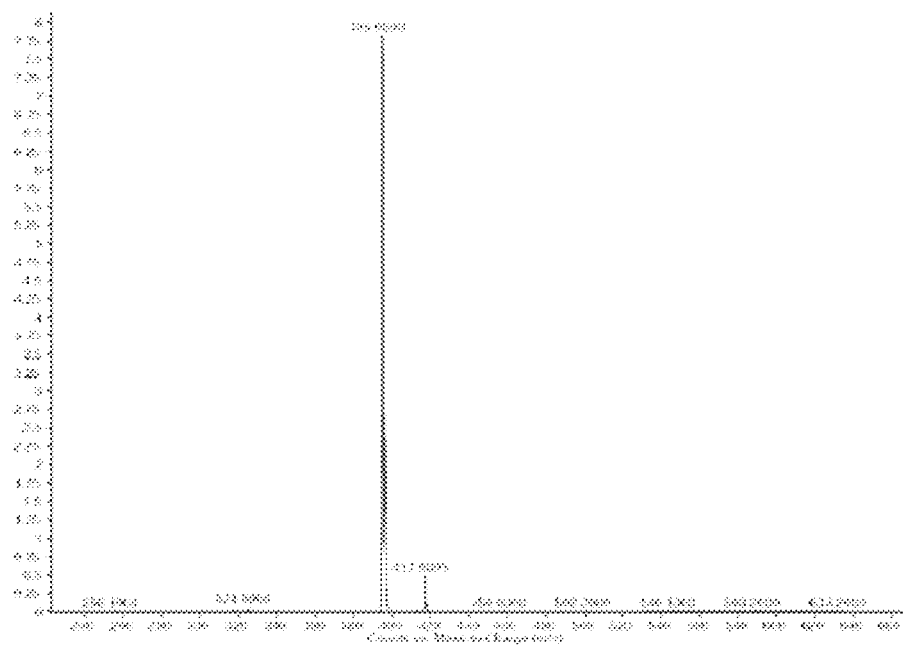
FIG. 9 illustrates the Mass spectrum of FT-1518 (+ ESI scan mode)
Figure 10:
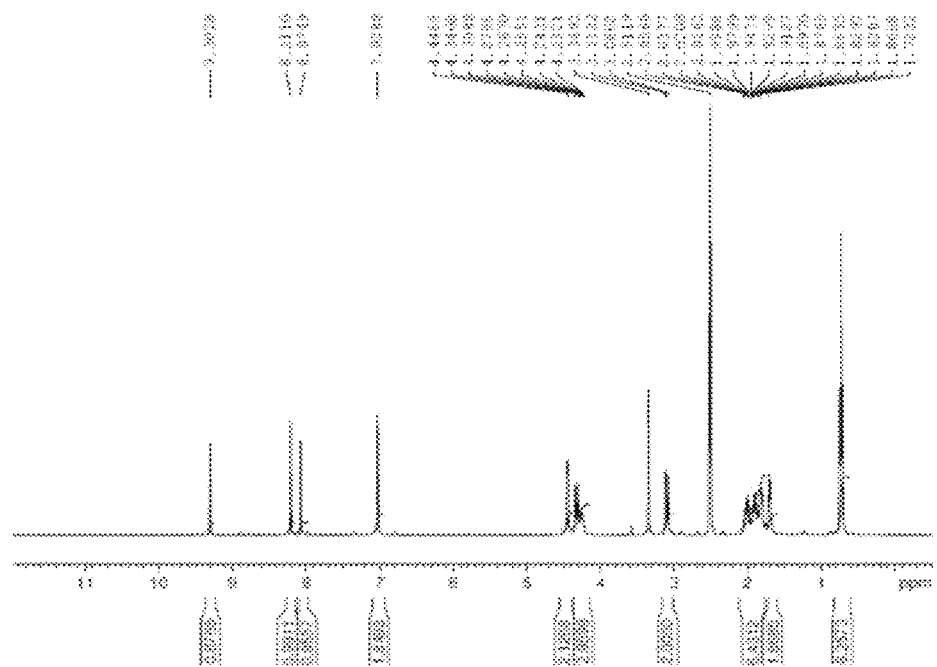
FIG. 10 illustrates the 1H-NMR of FT-1518 (in DMSO-D6)

The solid state properties of the crystalline drug substance FT1518 were studied using pXRD, DSC, TGA, Sorption-desorption isotherm, Mass spectrum+ESI scan mode), 1H-NMR of FT-1518 (in DMSO-D6). Results of Mass spectrum+ESI scan mode), 1H-NMR of FT-1518 (in DMSO-D6) are shown in FIGS. 9 and 10 respectively.

The evaluated initial parameters of the drug FT 1518 substance are shown in table no 1.

TABLE 1

| Drug substance physical parameters of crystalline form | | |
|---|---|---|
| Parameter | Method | Result |
| X-ray diffraction | 2-40° (2 theta) | Characteristic sharp diffraction patterns observed indicating crystallinity |
| Thermogravimetric analysis | Equilibrate at 25° C. Heat at 10° C./min up to 300° C. | <10.5% weight loss up to 100° C. indicating no hydrate or solvate and about 1.583% weight loss up to 150° C. |

TABLE 1-continued

Drug substance physical parameters of crystalline form

| Parameter | Method | Result |
|---|---|---|
| Thermal analysis by DSC | Equilibrate at 25° C. Heat at 10° C./min up to 300° C. | One melting indicating endotherm at around 185.37° C. No exotherm observed immediately after melting endotherm indicating no degradation immediately after melting. |
| Hygroscopicity and solvate formation | Drying: 40° C. for 2 h until 0-2% RH Sorption cycle: At 25° C., 0 to 95% RH Desorption cycle: At 25° C., 95 to 0% RH Equilibration condition for step change: 0.002% wt. change in 5 minutes | There was about <2% moisture uptake up to 70% RH and up to 5.72% moisture uptake at 95% RH. It was found to be slightly hygroscopic. As there was no hysteresis observed during desorption cycle, it was confirmed that it has no affinity to form hydrate. |
| Mass spectrum | Theoretical mass should be 394.47 Daltons | Peak indicating the mass of FT1518 showed m/z value of 395. |

Qualitative Solubility of FT-1518 in Various Media 2 mg quantity of API was taken in glass vial and small portions of solvent was added with vortexing till the clear solution is obtained (at room temperature or heating up to 50-60° C.). The approximate qualitative solubility of drug substance in various solvents is summarized in table 2.

TABLE 2

Summary table of qualitative solubility study

| Solvent/Media | Solubility (mg/mL) |
|---|---|
| Purified water | <1 |
| n-hexane | <1 |
| n-heptane | <1 |
| diethyl ether | <1 |
| Methyl tertiary butyl ether | 1 to 5 |
| Toluene | 10 to 25 |
| isopropyl acetate | 10 to 25 |
| 0.1N Hydrochloric acid | 25 to 50 |
| Acetonitrile | 25 to 50 |
| Ethyl acetate | 25 to 50 |
| Isopropyl alcohol | 50 to 100 |
| Acetone | 50 to 100 |
| Dimethyl sulphoxide | >100 |
| N,N-dimethyl acetamide | >100 |
| N-methyl pyrrolidone | >100 |
| Ethanol | >100 |
| dichloromethane | >100 |
| Methanol | >100 |
| 1,4-dioxane | >100 |
| Tetrahydrofuran | >100 |

Salt Screening

Selection of Counter Ions

Based on the quantitative solubility data, the compound was found to be practically insoluble in purified water and soluble in organic solvents. The acidic counter ions were selected because of the weakly basic pKa values 1.70 and 4.07 (predicted 0.43 and 4.07). The acidic counterions were selected to screen the salt forming propensity of FT1518 compound. Theoretically, counterions with pKa values less than 2 units than basic pKa value of the compound are ideal for salt formation. (Table 3)

TABLE 3

Table of selected counterions for salt screening

| Counter ion | pKa |
|---|---|
| Hydrochloric acid | −7 |
| Nitric acid | −1.3 |
| Hydrobromic acid | −9 |
| Sulphuric acid | −1.5 |
| p-toluene sulfonic acid | −1.34 |
| methane sulfonic acid | −2.6 |
| naphthalene sulfonic acid | 0.27 |
| camphor sulfonic acid | 1.5 |
| citric acid | 3.13, 4.76 |
| maleic acid | 2.0, 6.26 |
| malonic acid | 2.8, 5.67 |
| lauric acid | 5.3 |
| salicylic acid | 2.97, 13.82 |
| malic acid | 3.4, 5.11 |
| fumaric acid | 3.03, 4.44 |
| tartaric acid | 3.04, 4.37 |
| succinic acid | 4.19, 5.57 |
| oxalic acid anhydrous | 1.25, 4.23 |
| pamoic acid | 2.67 |
| benzene sulfonic acid | −2.8 |
| phthalic acid | 2.94, 5.40 |
| adipic acid | 4.43, 4.41 |
| acetic acid | 4.75 |
| ethane sulfonic acid | 1.68 |

Salt Feasibility Trials

A common solvent method in which drug and counter ion would be soluble was optimised and salt screening was performed. So, qualitative solubility of counter ions was also performed in some solvents. Stoichiometrically, 1:1.125 ratio of drug and counter ion was selected to prepare solutions during salt screening experiments. (Table 4)

TABLE 4

Stoichiometrically (1:1.125) equivalent amount of counterion required for mono salt screening

| Counter ion | Weight (in mg) for 1 mg of free base | volume to be added for liquids (µL) |
|---|---|---|
| HCl | 3.121 | 2.6 |
| HNO$_3$ | 5.394 | 3.6 |
| H$_3$PO$_4$ | 8.390 | 4.5 |
| HBr | 6.927 | 4.6 |
| H$_2$SO$_4$ | 8.396 | 4.6 |
| p-toluene sulfonic acid | 14.742 | -NA- |
| methane sulfonic acid | 8.227 | 5.5 |

TABLE 4-continued

Stoichiometrically (1:1.125) equivalent amount of counterion required for mono salt screening

| Counter ion | Weight (in mg) for 1 mg of free base | volume to be added for liquids (μL) |
|---|---|---|
| 2-napthalene sulfonic acid | 17.827 | -NA- |
| camphor sulfonic acid | 19.887 | -NA- |
| citric acid | 16.448 | -NA- |
| maleic acid | 9.937 | -NA- |
| malonic acid | 8.909 | -NA- |
| lauric acid | 17.150 | -NA- |
| salicylic acid | 11.825 | -NA- |
| malic acid | 11.480 | -NA- |
| fumaric acid | 9.937 | -NA- |
| tartaric acid | 12.849 | -NA- |
| succinic acid | 10.110 | -NA- |
| oxalic acid anhydrous | 7.708 | -NA- |
| pamoic acid | 33.250 | -NA- |
| benzene sulfonic acid | 13.541 | 10.3 |
| pthalic acid | 14.224 | -NA- |
| adipic acid | 12.511 | -NA- |
| acetic acid | 5.141 | 4.9 |
| ethane sulfonic acid | 9.428 | 6.98 |

Note:
-NA- not applicable

Note: —NA— not applicable

Solubility of FT-1518 was checked in various counter ion solutions before performing salt screening to obtain an estimate of feasibility of salt formation in the respective counter ions.

TABLE 5

Summary table of qualitative solubility study of FT1518 in aqueous media containing counterions

| aqueous media | solubility in mg/mL |
|---|---|
| 0.1N $H_2SO_4$ | >100 |
| 0.1N HCl | 25 to 50 |
| 0.1N benzene sulfonic acid | 10 to 25 |
| 0.1N Maleic acid | 10 to 25 |
| 0.1N citric acid | 10 to 25 |
| 0.1N p-toluene sulfonic acid | 10 to 25 |
| 0.1N malonic acid | 5 to 10 |
| 0.1N oxalic acid | 5 to 10 |
| 0.1N tartaric acid | 5 to 10 |
| 0.1N HBr | 1 to 5 |
| 0.1N methane sulfonic acid | 1 to 5 |
| 0.1N succinic acid | 1 to 5 |
| 0.1N malic acid | 1 to 5 |
| 0.04N phthalic acid | <1 |
| 0.1N adipic acid | <1 |
| 0.1N lauric acid | Lauric acid doesn't dissolve in water at this concentration |
| 0.1N phthalic acid | phthalic acid doesn't dissolve in water |
| 0.1N pamoic acid | Pamoic acid doesn't dissolve in water at this concentration |
| 0.1N $HNO_3$ | Not performed |
| 0.1N camphor sulfonic acid | Not performed |
| 0.1N napthalene sulfonic acid | Not performed |
| 0.1N fumaric acid | Not performed |
| 0.1N salicylic acid | Not performed |
| 0.1N acetic acid | Not performed |

Using common solvent/solvent mixture conditions, various methods of salt formation like cooling crystallisation, solvent evaporation (slow), Antisolvent precipitation and precipitation of the salts from the solution were performed using various combinations.

Salt Screening Trials

Mostly common solvent technique was used. The common solvent system in which drug and counter ions will be soluble separately were selected.

Antisolvent precipitation and ion exchange methods were also evaluated for few salt screening trials.

A common approach where the drug (about 30 mg) was dissolved in suitable amount of organic solvent and counter ion solution was added. Then, heated at 50° C. to 60° C. for few minutes and allowed to equilibrate to room temperature to observe if any salt formation occurs due to crystallization or precipitation from solution.

Initial Shortlisting of Salts Screened

The prepared salts were shortlisted based on properties like solubility, pH of 2% w/v aqueous solution, chemical and physical stability.

Initially, equilibrium solubility and chemical % purity of the salts formed was determined in pH6.8 0.01M phosphate buffer (potassium dihydrogen phosphate buffer) using HPLC. (Table 6)

TABLE 6

Solubility and chemical % purity of the salts screened

| Name of salt | Solubility in pH 6.8 buffer (mg/mL) | % purity |
|---|---|---|
| Free base of FT-1518 | 0.02 | 97.22 |
| Maleate | 1.87 | 96.99 |
| Mesylate | 5.85 | 96.77 |
| Tartarate | 8.54 | 96.82 |
| Succinate | 0.34 | 96.80 |
| Fumarate | 2.62 | 97.29 |
| Adipate | 0.19 | 97.63 |
| Oxalate | 10.21 | 96.68 |
| Tosylate | 0.88 | 96.27 |
| Nitrate | 0.47 | 95.04 |
| Malonate | 1.55 | 97.56 |
| Camphor sulfonate | 8.32 | 96.56 |
| HCl salt | 0.57 | 96.89 |
| Esylate | 77.98 | 97.75 |
| Sulphate | 35.38 | 97.34 |
| Besylate | 5.5 | 96.54 |

Based on solubility, preference of salts was as given below which showed many fold or significant increase in solubility: Esylate>sulphate>oxalate>tartarate>camphor sulfonate>mesylate>besylate>Fumarate>maleate>Malonate The shortlisted salts based on solubility were kept at 40° C./75% RH for 7 days in open condition and then analyzed for % purity by HPLC, PXRD (to understand the physical form risk) and pH in 2% w/v aqueous dispersion/solution. (Table 7)

TABLE 7

1 week Stability of the salts 40° C./75% RH shortlisted based on solubility and % purity

| Name of salt | % purity | XRD | pH of 2% w/v aqueous dispersion/solution |
|---|---|---|---|
| FT-1518 | 97.82 | Same as initial form | — |
| Oxalate | 97.04 | Same as initial form | 2.6 (dispersion) |
| Sulphate | 97.85 | Same as initial form | 1.8 (soluble) |
| Fumarate | 95.81 | Same as initial form | — |
| Tartarate | 96.89 | Same as initial form | — |
| Mesylate | 97.07 | Same as initial form | 2.2 (dispersion) |
| Camphor sulfonate | 97.00 | Same as initial form | 2.6 (wet mass) |
| Esylate | 98.07 | Same as initial form | 2.1 (soluble) |
| Besylate | 98.22 | Some form conversion (risk of polymorphism) | 2.4 (dispersion) |

Summary of Salts Shortlisted:
Based on Stability and Solubility,
  Esylate>sulphate>oxalate>camphor sulfonate>mesylate>besylate would be order of choice for salt selection.
  Based on pH observation, order of preference
  Oxalate>camphor sulfonate>besylate>mesylate>esylate>sulphate
Total Preference:
  Oxalate>esylate>camphor sulfonate>mesylate=besylate
Esylate Salt Trials

TABLE 8

Summary table of salt feasibility trials by ethane sulfonic acid

| counterion | Ethane sulfonic acid | Ethane sulfonic acid | Ethane sulfonic acid |
|---|---|---|---|
| ratio (drug: counterion) | 1:1.125 | 1:2.1 (di-salt) | 1:1.125 |
| Solvent media | Common solvent technique-solvent evaporation | Common solvent technique-solvent evaporation | Common solvent technique-Precipitation from solution |
| solvent system used | Acetone | acetone | THF |
| Experimental | Stirred at 50° C. for 1 hour and kept at RT after saturation. | Stirred at 50° C. for 1 hour and kept at RT after saturation. | Stirred at 50° C. for 1 hour and kept at RT after saturation. |
| observations | Crystallised or solid formed | Solid paste obtained | Precipitate obtained. |

Figure 11:
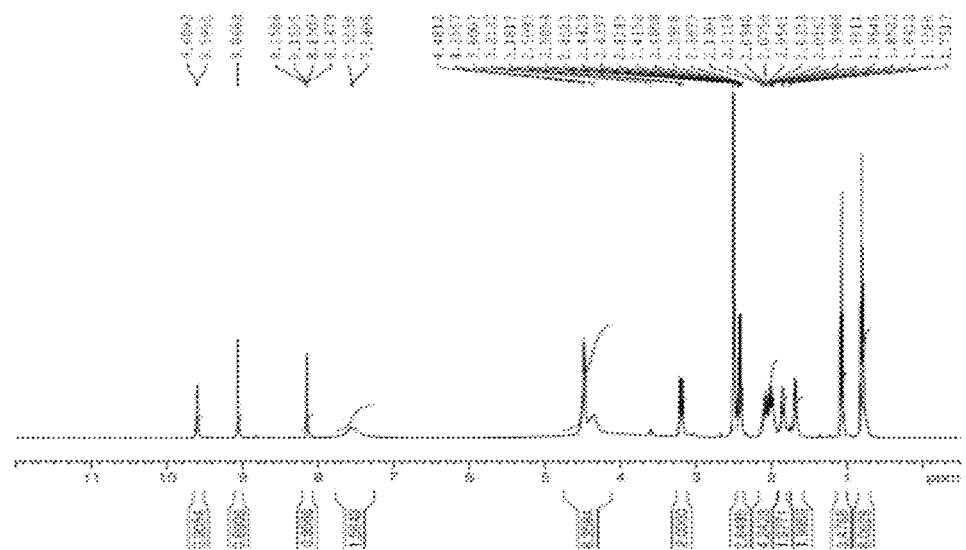
FIG. 11 illustrates the 1H NMR of esylate salt trial (using THF)

Esylate salt formation using acetone and tetrahydrofuran were confirmed from PXRD. FIG. 11 depicts 1H NMR of esylate salt when precipitated from tetrahydrofuran and confirms the salt formation.

Oxalate Salt Trials

TABLE 9

Summary table of salt feasibility trials by oxalic acid

| counterion | Oxalic acid | Oxalic acid | Oxalic acid |
|---|---|---|---|
| ratio (drug: counterion) | 1:1.125 | 1:1.125 | 1:1.125 |
| Solvent media | Common solvent technique-solvent evaporation | Common solvent technique-solvent evaporation | Common solvent technique-solvent evaporation |
| solvent system used | Ethanol | methanol | IPA |
| Experimental | Stirred at 50° C. for 1 hour and kept at RT after saturation. | Stirred at 50° C. for 1 hour and later evaporated in vacuum slowly | Stirred at 50° C. for 1 hour and later evaporated in vacuum slowly |
| observations | crystallised or solid formed | crystallised or solid formed | crystallised or solid formed |

Summary of Oxalate Salt Trials

Figure 12:
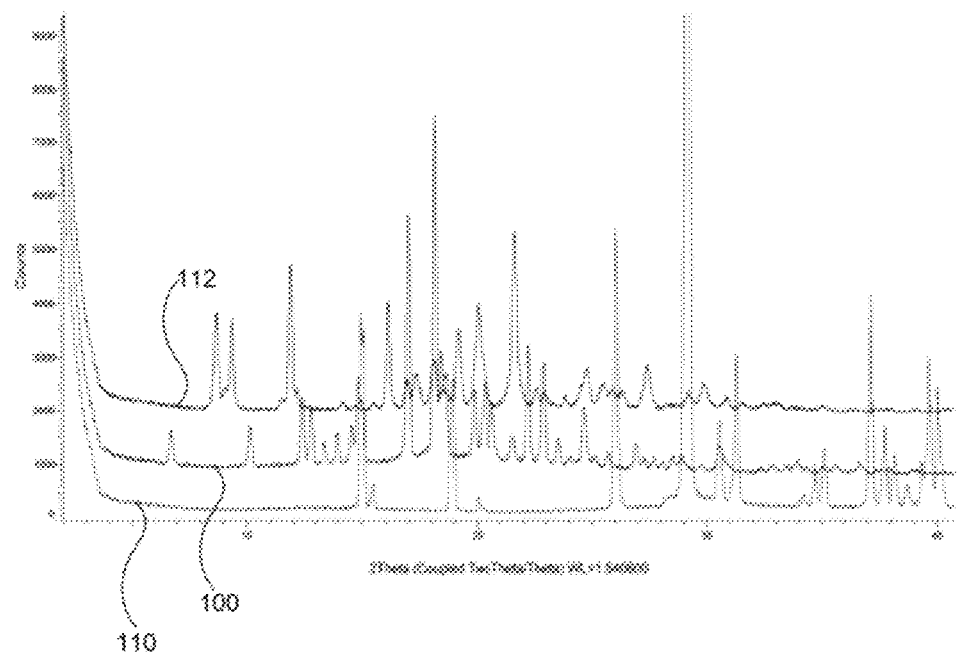
FIG. 12 illustrates the PXRD overlay of oxalate salt trials (using ethanol)
Figure 13:
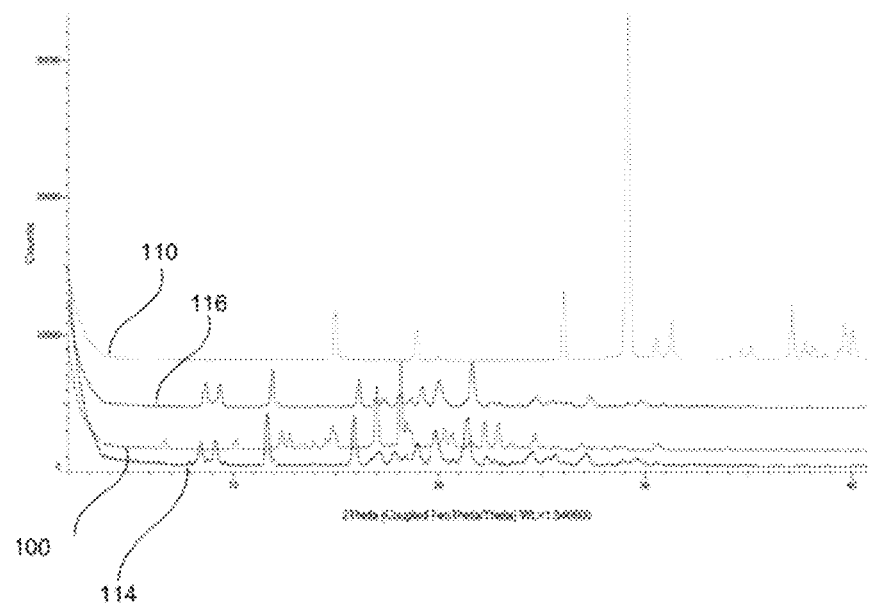
FIG. 13 illustrates the PXRD overlay of oxalate salt trials (using methanol, IPA)
Figure 14:
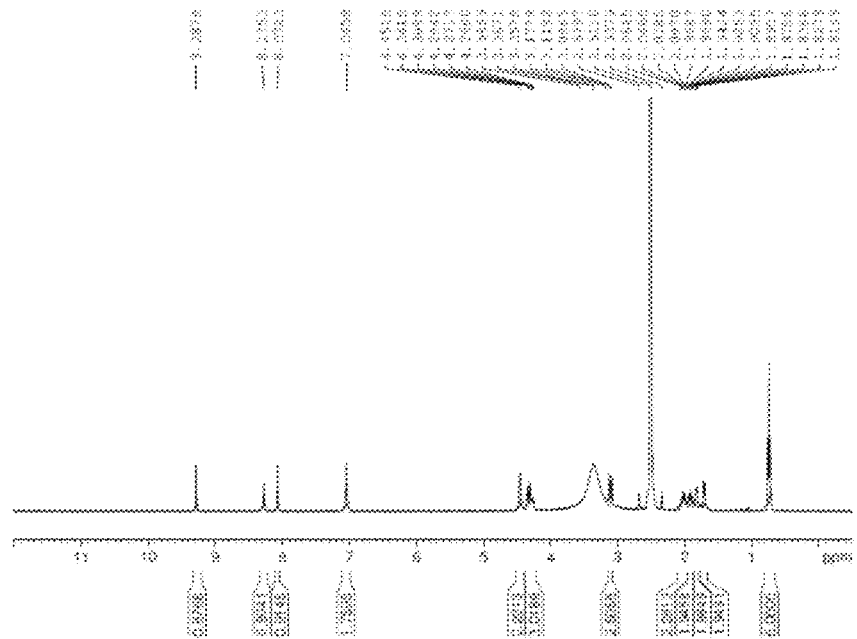
FIG. 14 illustrates the 1H NMR of oxalate salt trial (using ethanol)

Oxalate salt formation was confirmed from PXRD and 1H NMR. FIG. 12 depicts a PHRD overlay of oxalate salt recrystallized from ethanol. In FIG. 12, X-ray diffraction pattern 112 of oxalate salt recrystallized from ethanol was compared with the diffraction pattern 100 of FT-1518 base and diffraction pattern 110 of oxalic acid. FIG. 13 depicts a PHRD overlay of oxalate salt when recrystallized from methanol and IPA. XRD patterns 114 of oxalate salt formed by methanol and 116 of oxalate formed by IPA were compared with the XRD patterns 100 of FT-1518 base and 110 of oxalic acid. Oxalate salt formation was confirmed from PXRD and 1H NMR when recrystallized from methanol and IPA. FIG. 14 depicts 1H NMR of oxalate salt recrystallized using ethanol.

Physical Form Screening of Selected Salts

To proceed with selection of salts and physical form screening for further development, esylate and oxalate salts of FT-1518 were screened.

Initial Characterisation of Esylate and Oxalate Salts of FT-1518

Characterization of FT-1518 Esylate

The solid state properties of the amorphous drug substance FT-1518 were studied using pXRD, DSC and TGA for both Esylate salt and oxalate salt that are formed.

Summary of Initial Characterization:

FT-1518 ESYLATE: The PXRD of FT-1518 esylate salt showed characteristic diffraction pattern. DSC thermogram showed slight broader endotherm at less than 100° C. (only residual solvent after recrystallization, which can be removed in process development), followed by two sharp endotherms at 231 and 246° C. TGA showed 0.915% weight loss up to 125° C. indicating no solvate or hydrate form.

Figure 15:
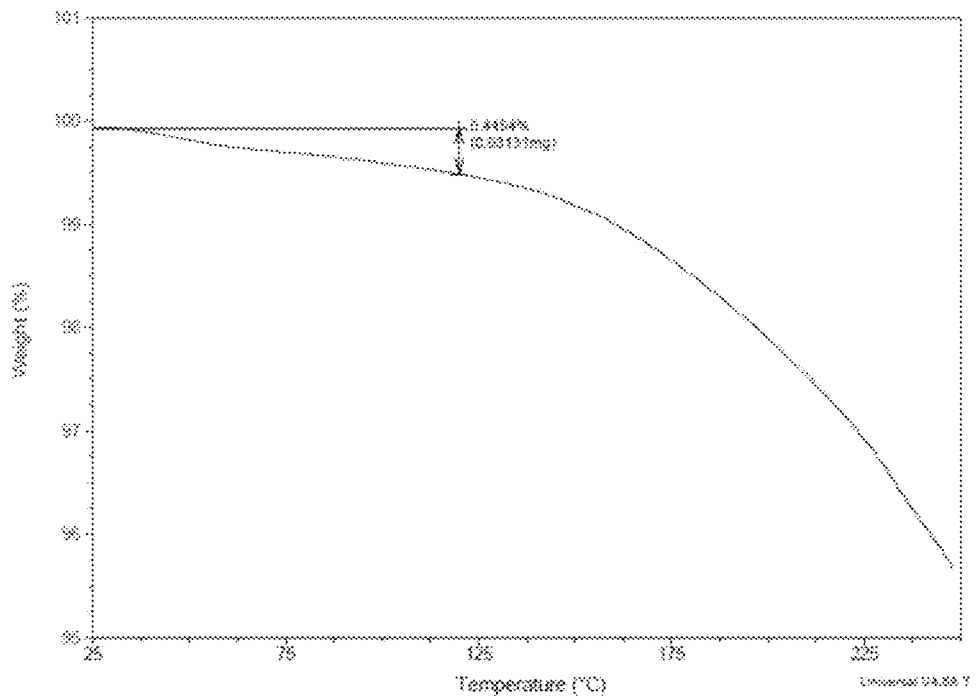
FIG. 15 illustrates the TGA thermogram of oxalate salt

FT-1518 OXALATE: The PXRD of FT-1518 oxalate salt showed characteristic diffraction pattern different from that of esylate salt. The DSC thermogram showed one endotherm at around 117° C. followed by degradation indicating endotherm. FIG. 15 depicts TGA thermogram of the oxalate salt that is formed. The TGA data showed weight loss of about 0.44% by weight when heated up to 125° C.

Solubility of FT-1518 Free Base, Esylate and Oxalate

Qualitative Solubility:

Weighed quantity of API was taken in glass vial and small portions of solvent was added with vortexing till the clear solution is obtained (at room temperature or heating up to 50-60° C.). The approximate kinetic solubility of free base, esylate and oxalate salts of FT-1518 in various solvents is summarized in table 10, 11 and 12 respectively.

TABLE 10

Summary table of kinetic/visual solubility study of free base

| Solvent/media | solubility in mg/mL |
|---|---|
| Water | <1 |
| n-hexane | <1 |
| n-heptane | <1 |
| diethyl ether | <1 |
| Methyl tertiary Butyl Ether | 1 to 5 |
| Toluene | 10 to 25 |
| isopropyl acetate | 10 to 25 |
| 0.1N HCl | 25 to 50 |
| Acetonitrile | 25 to 50 |
| Ethyl acetate | 25 to 50 |
| 2-propanol | 50 to 100 |
| Acetone | 50 to 100 (initially was soluble, now seems to be insoluble) |
| Dimethyl sulphoxide | >100 |
| N,N-Dimethyl acetamide | >100 |
| N-Methyl 2-Pyrrolidone | >100 |
| Ethanol | >100 |
| dichloromethane | >100 |
| Methanol | >100 |
| 1,4-dioxane | >100 |
| Tetra hydro furan | >100 |

TABLE 11

Summary table of kinetic/visual solubility study of Esylate salt

| Solvent/media | solubility of Esylate in mg/mL |
|---|---|
| ethyl acetate | <1 |
| Tetrahydrofuran | <1 |
| Acetone | <1 |
| Toluene | <1 |
| n-hexane | <1 |
| 1,4-dioxane | 1 to 5 |
| Dichloromethane | 5 to 10 |
| Propan-2-ol | 10 to 25 |
| Ethanol | 25 to 50 |
| Methanol | 50 to 100 |
| Acetonitrile | >100 |
| Dimethyl sulphoxide | >100 |
| N-Methyl 2-Pyrrolidone | >100 |

TABLE 12

Summary table of kinetic/visual solubility study of Oxalate salt

| Solvent/media | solubility of Oxalate in mg/mL |
|---|---|
| Dichloromethane | <1 |
| ethyl acetate | <1 |
| Toluene | <1 |
| n-hexane | <1 |
| Acetone | 1 to 5 |
| 1,4-dioxane | 5 to 10 |
| Tetrahydro furan | 10 to 25 |
| Methanol | 10 to 25 |
| Ethanol | 10 to 25 |
| Propan-2-ol | 10 to 25 |
| Acetonitrile | 50 to 100 |
| Dimethyl sulphoxide | >100 |
| N-Methyl 2-Pyrrolidone | >100 | pH Vs Solubility Study of Salts and Free Base of FT-1518:

In 2 mL volume of buffers (ranging from pH 1.2 to 7.4) and purified water, compound (either free base or esylate or oxalate) was added with increments until the compound doesn't dissolve further in the medium and compound remains undissolved or excess in the solution. The samples were kept for overnight at ambient room temperature to saturate/equilibrate. The dispersions were filtered through 0.45 μm PVDF or nylon membrane filters and the filtrates were analysed using RP-HPLC for determination of solubility of compounds in various buffers and purified water.

TABLE 13

Summary table of pH vs solubility study

| | Solubility in mg/mL | | |
|---|---|---|---|
| Medium | Free base | Esylate salt | Oxalate salt |
| Water | 0.12 | >539.39 | 11.03 |
| pH 1.2 HCl | >50.25 | >587.07 | >52.76 |
| pH 3.0 Citrate buffer | 2.11 | >76.38 | 20.25 |
| pH 4.0 Acetate buffer | 0.34 | 53.25 | 1.05 |
| pH 5.0 Acetate buffer | 0.14 | 0.84 | 0.14 |
| pH 6.8 Phosphate buffer | 0.11 | 79.08 | 5.28 |
| pH 7.4 Phosphate buffer | 0.1 | 40.8 | 0.76 |

Physical Form Screening Study of FT-1518 Esylate

Cooling Crystallization of FT-1518 Esylate

Weighed quantity of drug substance was dissolved in small amount (enough volume to solubilize API) in solvent by heating at 50-55° C. Clear solutions obtained were kept for evaporation at refrigerated conditions. The experimental conditions in which the cooling crystallisation was performed is mentioned in table 14.

TABLE 14

Cooling crystallization experiments of FT-1518 Esylate

| Samples | volume (mL) | Initial | 1 day | 3 Days |
|---|---|---|---|---|
| DCM | 10 | soluble | Crystals formed | Crystals formed |
| ethanol | 4 | soluble | Crystals formed | Crystals formed |
| methanol | 2 | soluble | Crystals formed | Crystals formed |
| acetonitrile | 1 | soluble | Still a Solution | Still a Solution |

Figure 16:
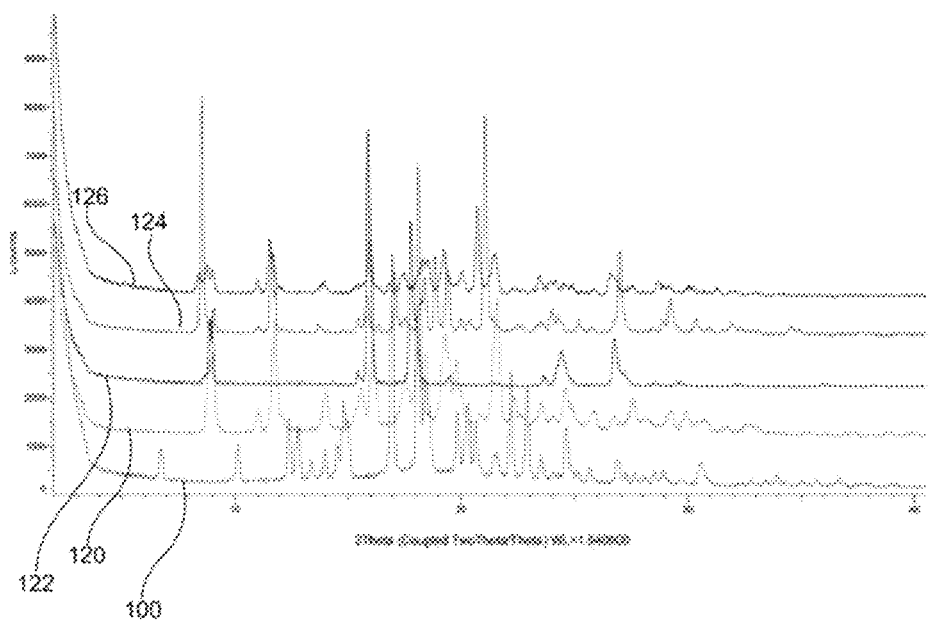
FIG. 16 illustrates the overlay of pXRD of polymorph screening of FT-1518 Esylate by cooling crystallization
Figure 17:
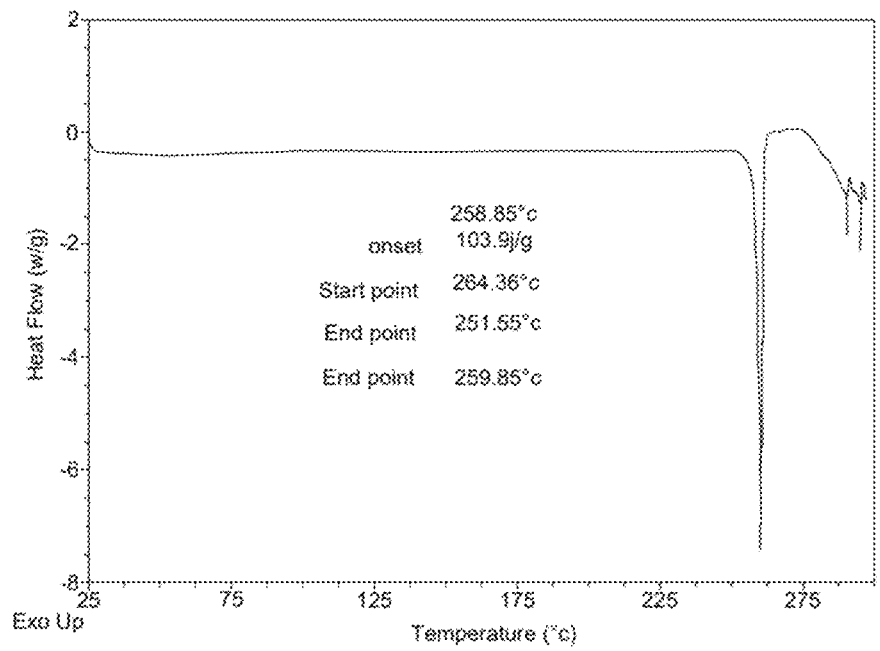
FIG. 17 illustrates the DSC of FT-1518 Esylate crystallized in methanol by cooling crystallization

FIG. 16 depicts PXRD of polymorph screening of FT-1518 Esylate by cooling crystallization. XRD patterns 122, 124, and 126 of esylate salt formed by cooling crystallization in methanol, ethanol, and DCM respectively, were compared with XRD pattern 120 of esylate salt and 100 of FT-1518 base. It can be seen from FIG. 16 that distinct forms than FT-1518 base are formed by cooling crystallization in methanol, ethanol, and DCM. XRD pattern 122 of esylate salt formed by cooling crystallization in methanol matches with the XRD pattern 120 of esylate salt. FIG. 17 illustrates DSC of FT-1518 Esylate crystallized in methanol by cooling crystallization. The results of TGA and DSC of physical form screening samples by cooling crystallization experiment are shown in Table 15.

TABLE 15

Results of cooling crystallization experiments of FT-1518 Esylate

| Sample name | DSC | TGA |
|---|---|---|
| Esylate_Dicholoromethane | Endotherm - 257.73° C. , 241.13° C. (sharp) | 0.4918% up to 125° C. |
| esylate_Ethanol | Endotherm - 242.12° C. , 256.88° C. (sharp) Followed by degradation | 1.091% up to 175° C. |
| Esylate_Methanol | Endotherm - 259.85° C. (sharp) Followed by degradation | 0.8229% up to 125° C. |
| Esylate salt initial | Endotherm - 112.44° C. (broad), 231.19° C., 236.65° C. (sharp) | 0.915% up to 125° C. |
| Free base | Endotherm −185.37° C. | 0.36% up to 100° C.; 1.58% up to 150° C. |

Summary of Polymorph Screening of FT-1518 Esylate by Cooling Crystallization:

New forms were obtained in crystallized samples of ethanol and DCM. Based on DSC of methanol crystallized sample, it was concluded that the form with higher and single melting point can be crystallized the most stable form of Esylate of FT-1518 in methanol.

Solvent Evaporation Screening of FT-1518 Esylate

Figure 18:
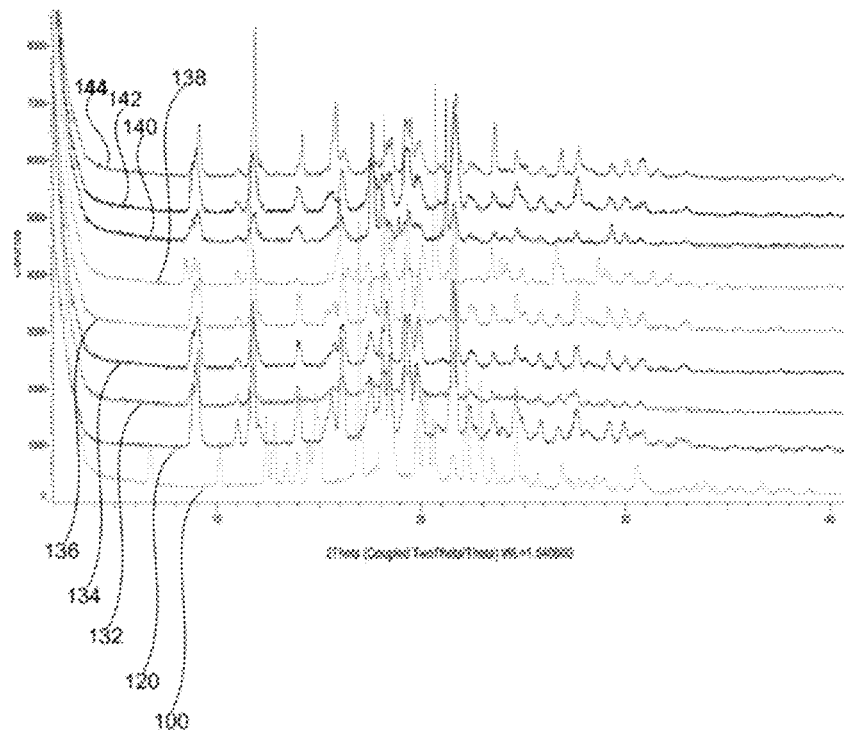
FIG. 18 illustrates the overlay of pXRD of Physical form screening of FT-1518 Esylate by solvent evaporation
Figure 19:
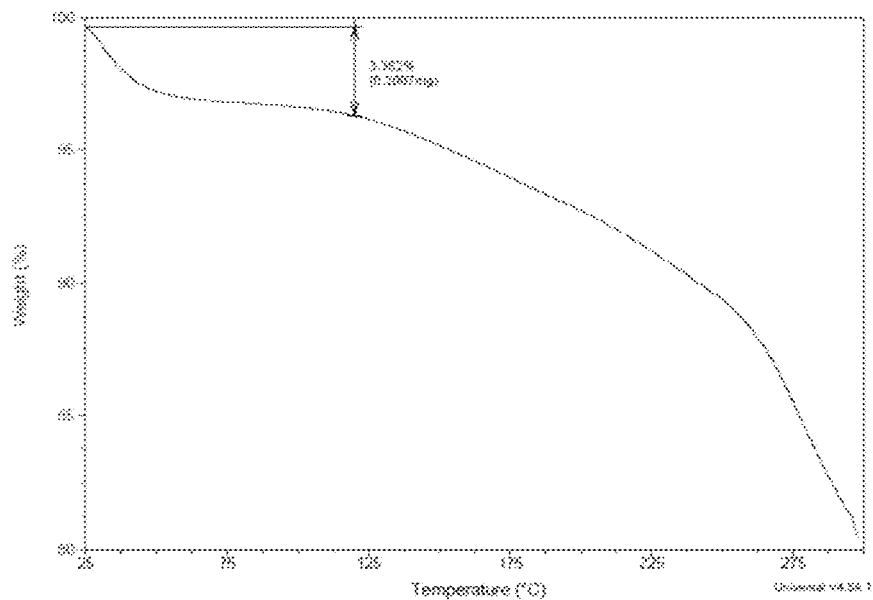
FIG. 19 illustrates the TGA of FT-1518 Esylate crystallized in dichloromethane by solvent evaporation
Figure 20:
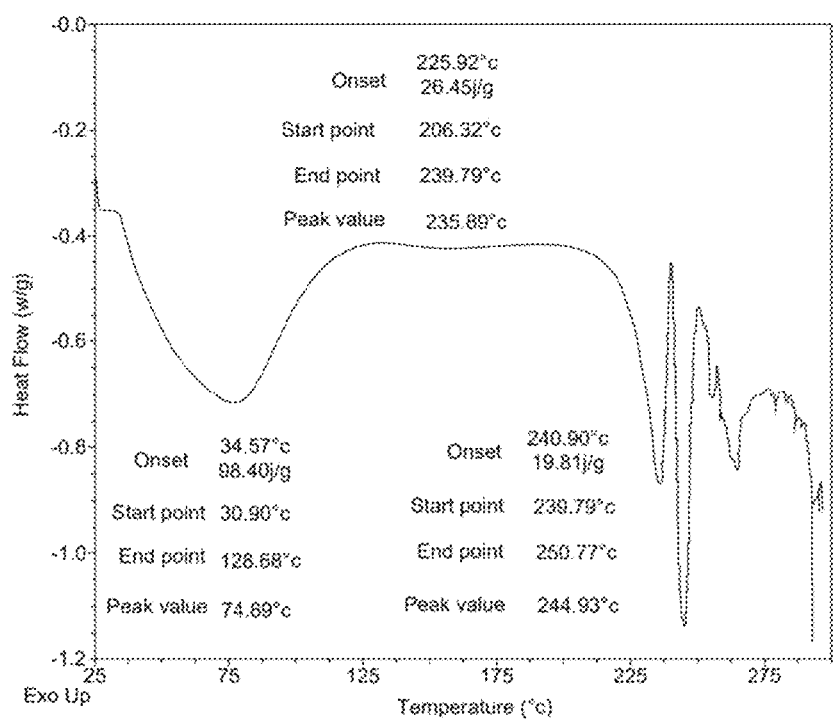
FIG. 20 illustrates the DSC of FT-1518 Esylate crystallized in dichloromethane by solvent evaporation
Figure 21:
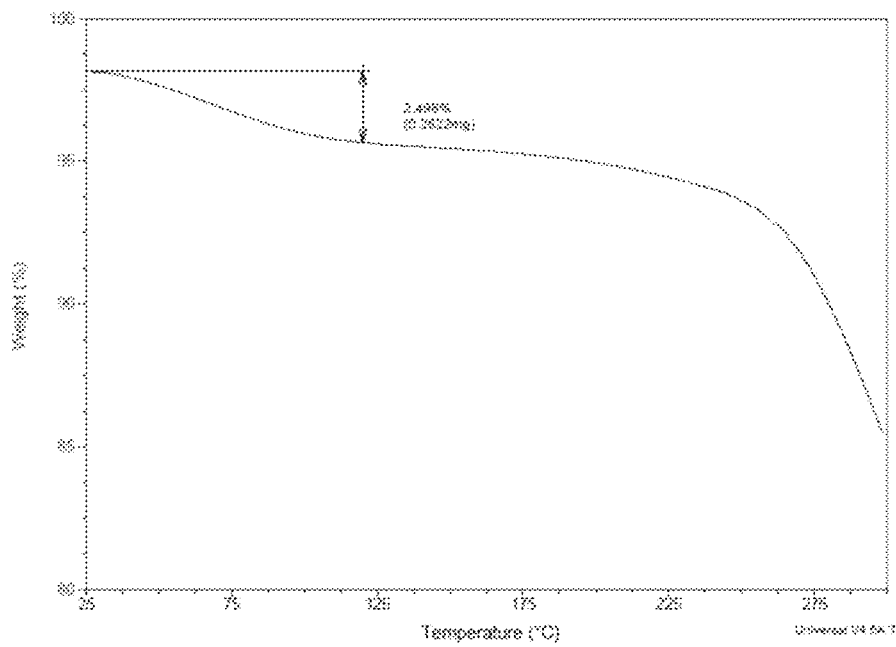
FIG. 21 illustrates the TGA of FT-1518 Esylate crystallized in acetonitrile by solvent evaporation
Figure 22:
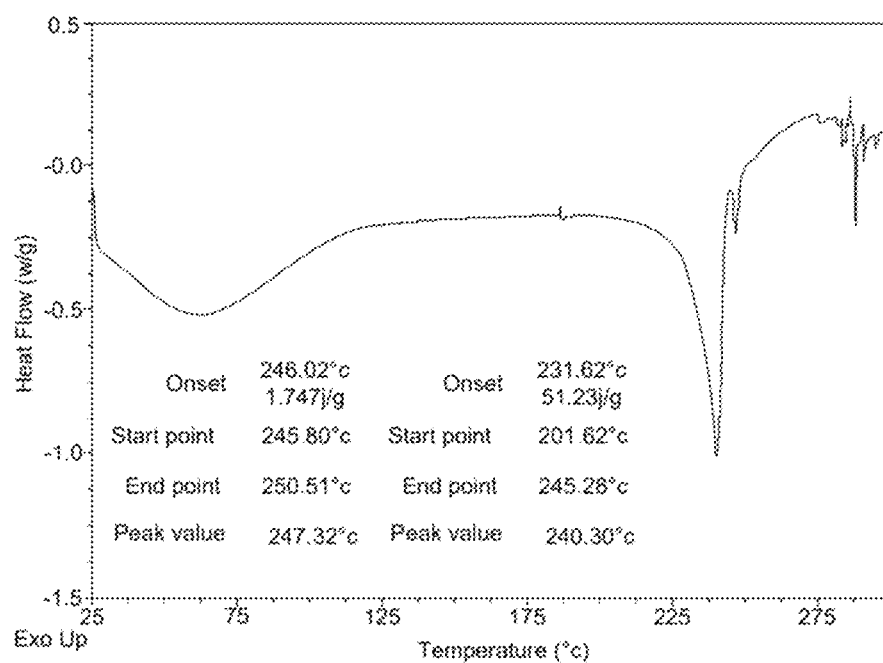
FIG. 22 illustrates the DSC of FT-1518 Esylate crystallized in acetonitrile by solvent evaporation
Figure 23:
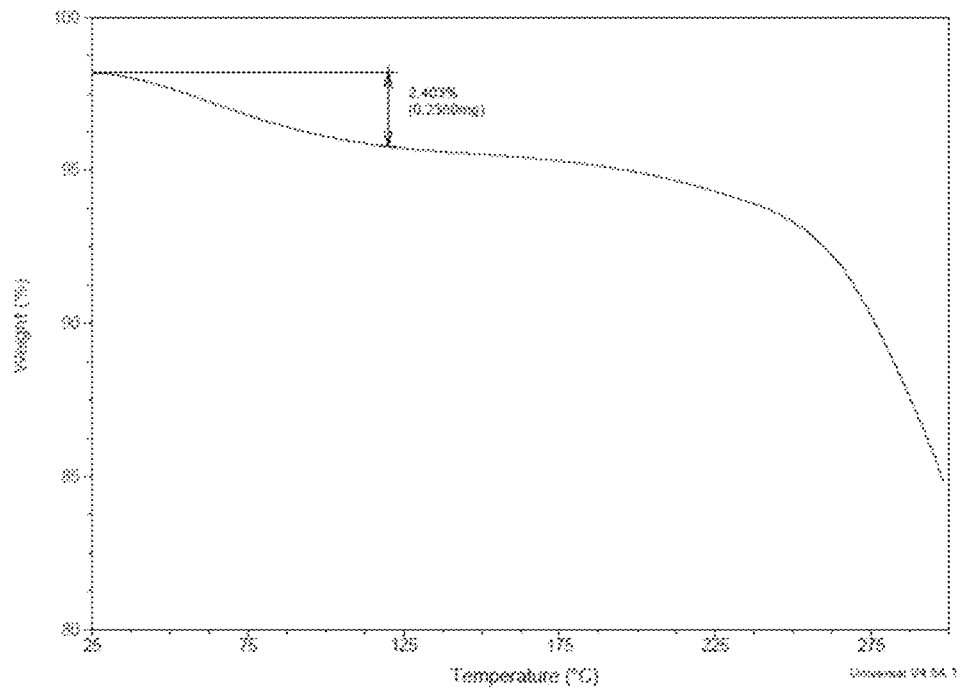
FIG. 23 illustrates the TGA of FT-1518 Esylate crystallized in Tetrahydrofuran:water (9:1) by solvent evaporation
Figure 24:
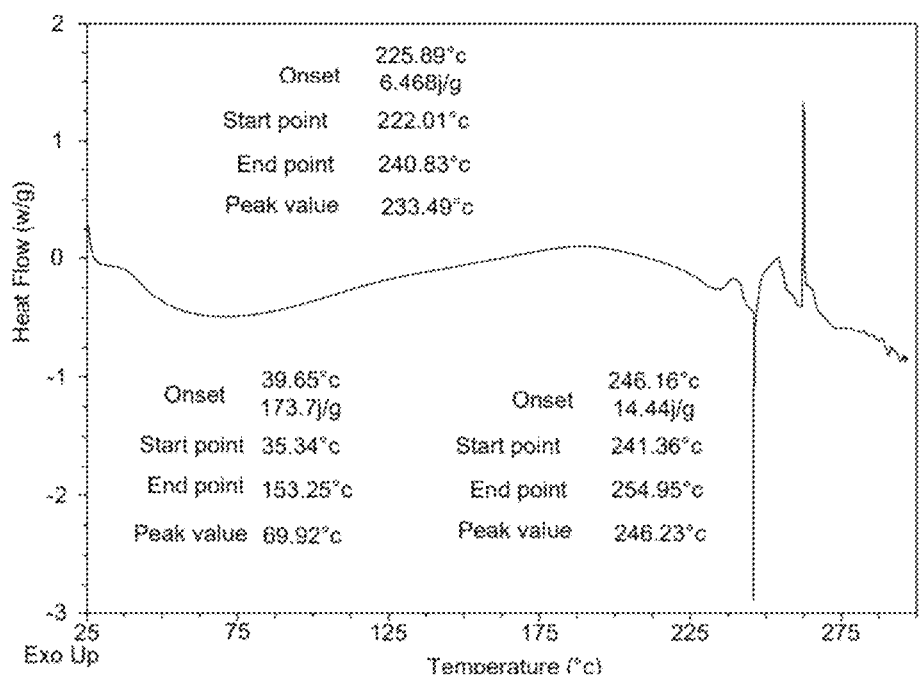
FIG. 24 illustrates the DSC of FT-1518 Esylate crystallized in methanol by solvent evaporation

The compound was dissolved in various solvents by heating at 50-55° C. to prepare solutions. Then, heated at 50° C. on a hot plate to evaporate solvent to concentrate the solution and let it at room temperature until complete solvent evaporated or recrystallization to occur with concentration. The details of the experiment and results are mentioned in the table 16 and 17. FIG. 18 depicts overlay of PXRD of physical form screening of FT-1518 esylate by solvent evaporation. In FIG. 18, XRD patterns 132, 134, 136, 138, 140, 142, 144 of esylate crystallized in methanol, THF:water (90:10), acetonitrile, DCM, ethanol, acetone, and THF respectively by solvent evaporation method are compared with the XRD patterns 120 of esylate salt and XRD pattern 100 of FT-1518 base. FIG. 19 and FIG. 20 respectively illustrate TGA and DSC of esylate crystallized in dichloromethane by solvent evaporation. FIG. 21 and FIG. 22 respectively illustrate TGA and DSC of esylate crystallized in acetonitrile by solvent evaporation. FIG. 23 illustrates TGA of esylate crystallized in tetrahydrofuran:water (9:1) by solvent evaporation, and FIG. 24 illustrates DSC of esylate crystallized in methanol by solvent evaporation.

TABLE 16

Solvent evaporation experiments of FT-1518 Esylate

| Samples | volume (mL) | Initial | 1 hour | 3 Day |
| --- | --- | --- | --- | --- |
| acetone | 8 | Dispersion | Dispersion | Crystals formed |
| 1,4-dioxane | 21 | No Soluble | Not Soluble | Crystals formed |
| DCM | 10 | soluble | soluble | Crystals formed |
| ethanol | 4 | soluble | soluble | Crystals formed |
| methanol | 2 | soluble | soluble | Crystals formed |
| acetonitrile | 1 | soluble | soluble | Crystals formed |

TABLE 17

Results of Solvent evaporation experiments of FT-1518 Esylate

| Sample | DSC | TGA |
| --- | --- | --- |
| Ethanol | Endotherm - 69.67° C. (broad), 153.19° C. (broad) followed by degradation from above 175° C. | 2.13% up to 125° C. |
| Dichloromethane | Endotherm - 74.89° C. (broad), 235.89° C., 224.93° C. (sharp) | 3.362% up to 125° C. |
| Acetonitrile | Endotherms - broad endotherm up to 120° C., 240.32° C., 247.32° C. (sharp) | 2.498% up to 125° C. |
| THF:Water (90:10) | Endotherms - broad endotherm up to 120° C., 246.37° C., 239.52° C. (sharp) | 2.403% up to 125° C. |
| Methanol | Endotherms - broad endotherm at 69.92° C., 233.49° C., 246.23° C. (sharp) along with degradation | 5.990% up to 125° C. |
| Esylate salt initial | Endotherm - 112.44° C. (broad), 231.19° C., 236.65° C. (sharp) | 0.915% up to 125° C. |
| Free base of FT-1518 | Endotherm −185.37° C. | 0.36% up to 100° C.; 1.58% up to 150° C. |

Summary of Polymorph Screening of FT-1518 Esylate by Solvent Evaporation:

No change in polymorph was observed during the investigation in various solvents except DCM. Hence, all the residues obtained may be stable forms in these experiments. Change in few peaks were observed in DCM sample.

Slurry Transformation Experiments of FT-1518 Esylate

The hydrate and solvate formation propensity of the salt was evaluated using solvents, aqueous medium and solvent: water binary mixture. The drug substance was dispersed in binary mixture of water and Tetrahydrofuran, solvents and subjected for slurry transformation at 25° C. and 40° C. for a period of 7 days using bottle rotating apparatus with excess amount of drug substance.

Figure 25:
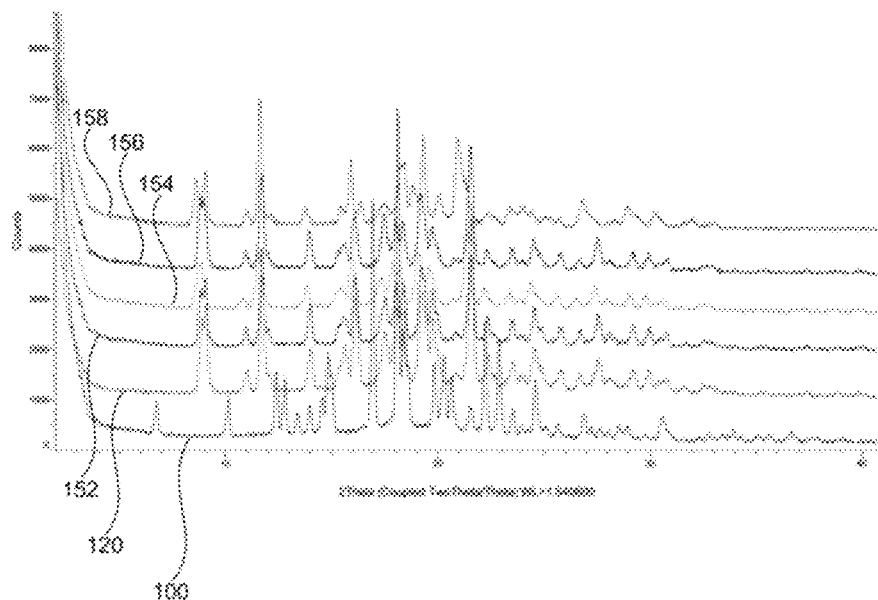
FIG. 25 illustrates the PXRD results of FT-1518 Esylate slurry transformation experiments at RT
Figure 26:
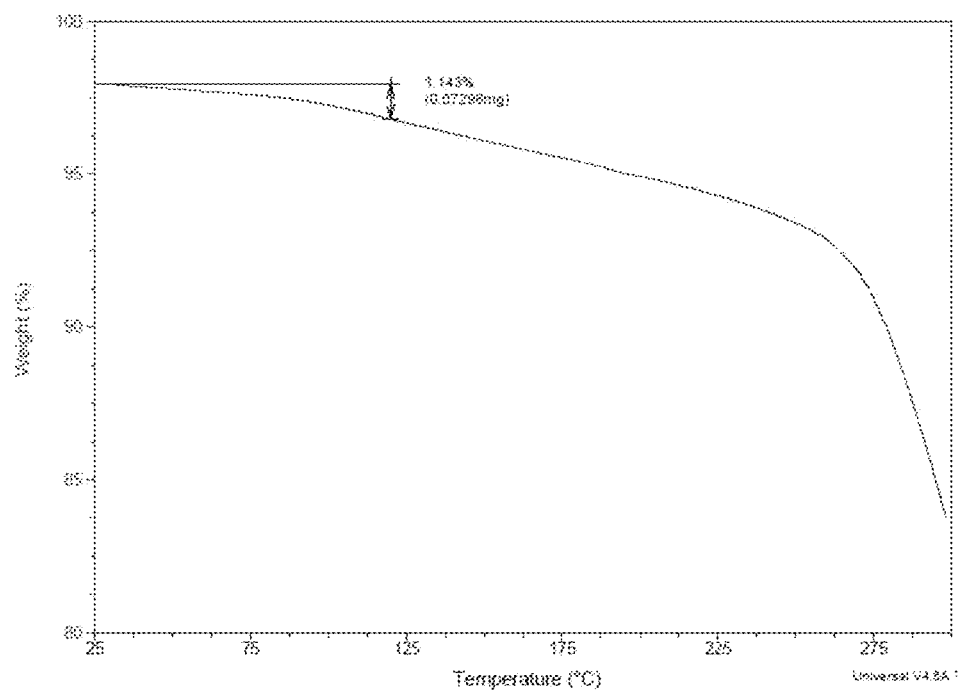
FIG. 26 illustrates the TGA of FT-1518 Esylate crystallized in ethyl acetate by slurry at 25° C.
Figure 27:
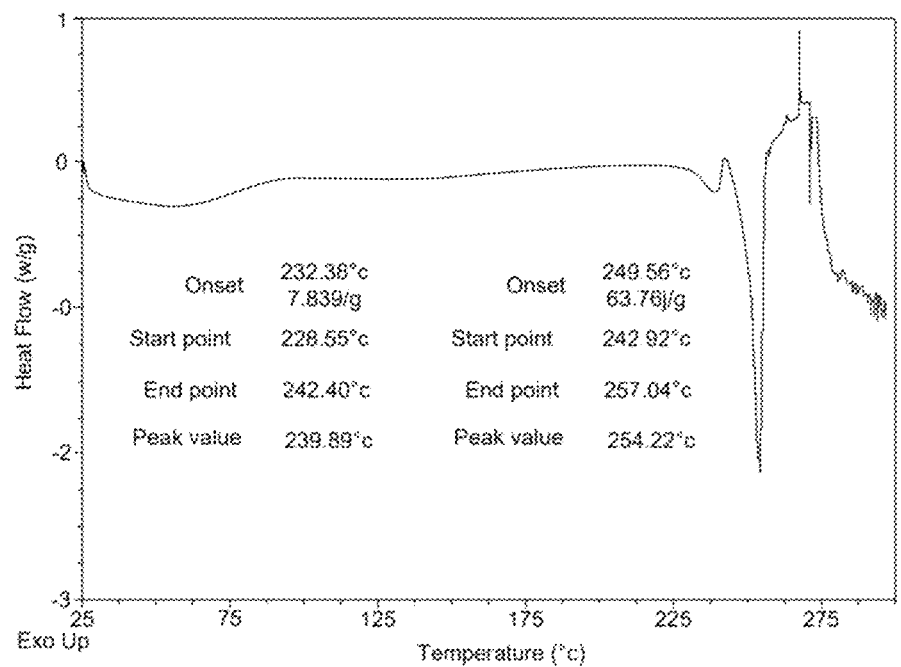
FIG. 27 illustrates the DSC of FT-1518 Esylate crystallized in ethyl acetate by slurry at 25° C.
Figure 28:
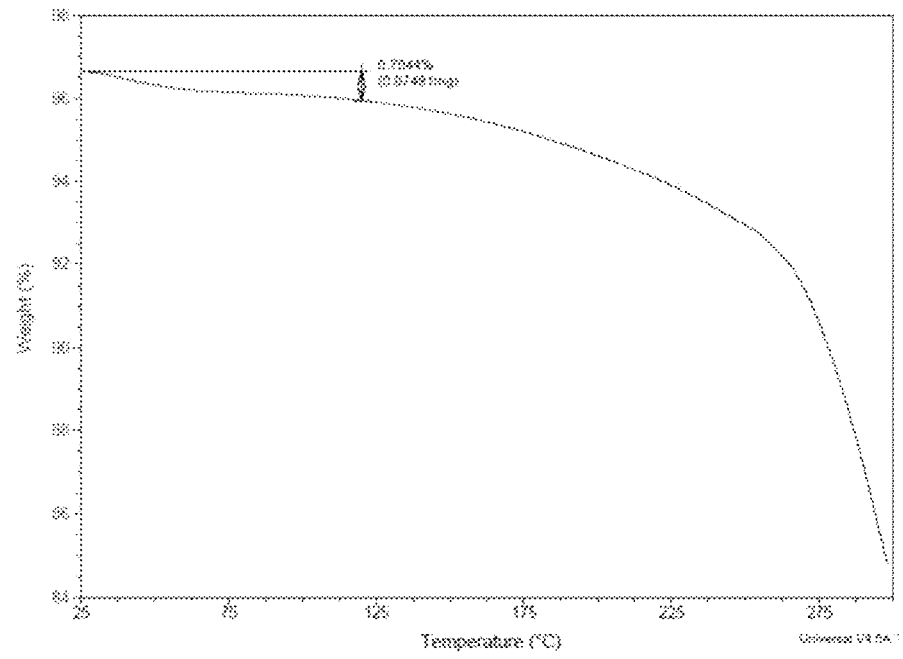
FIG. 28 illustrates the TGA of FT-1518 Esylate crystallized in Tetrahydrofuran by slurry at 25° C.
Figure 29:
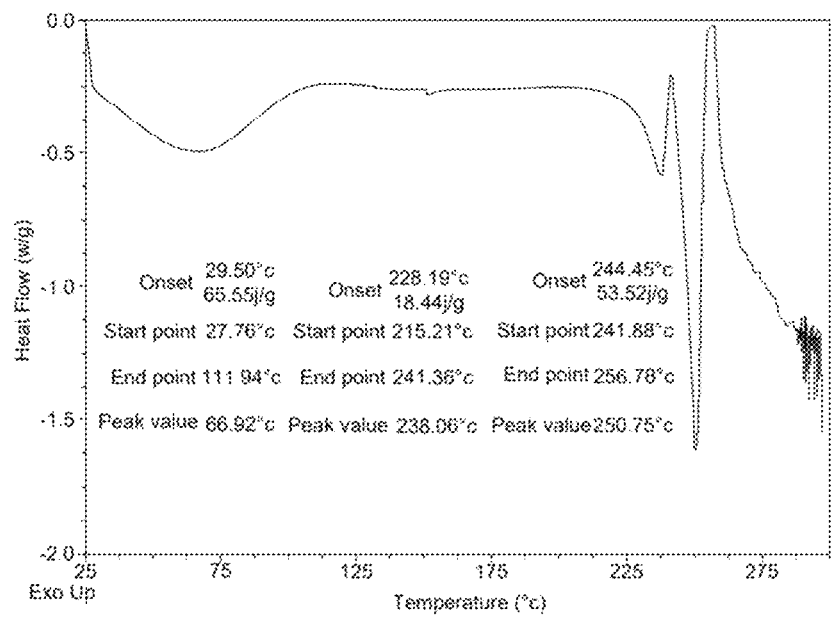
FIG. 29 illustrates the DSC of FT-1518 Esylate crystallized in Tetrahydrofuran by slurry at 25° C.
Figure 30:
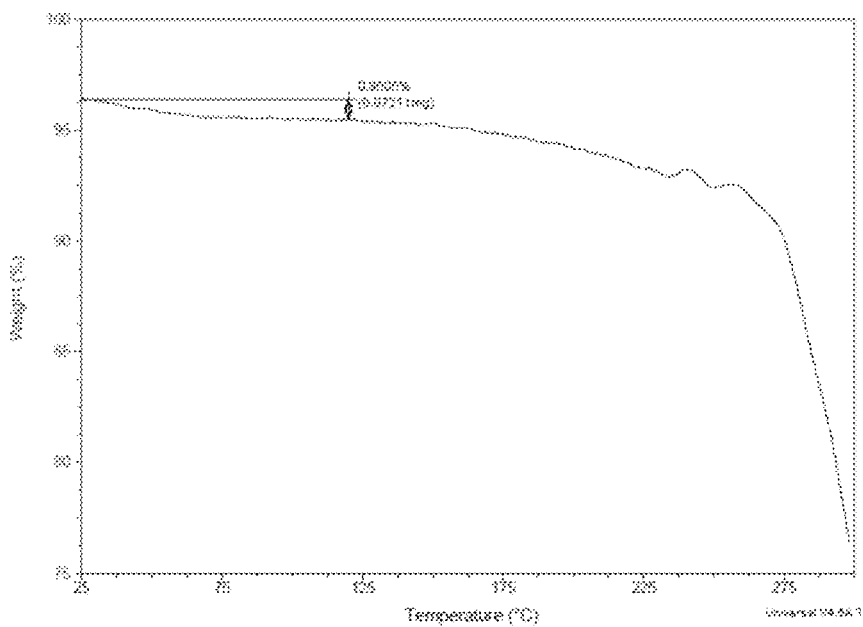
FIG. 30 illustrates the TGA of FT-1518 Esylate crystallized in Toluene by slurry at 25° C.
Figure 31:
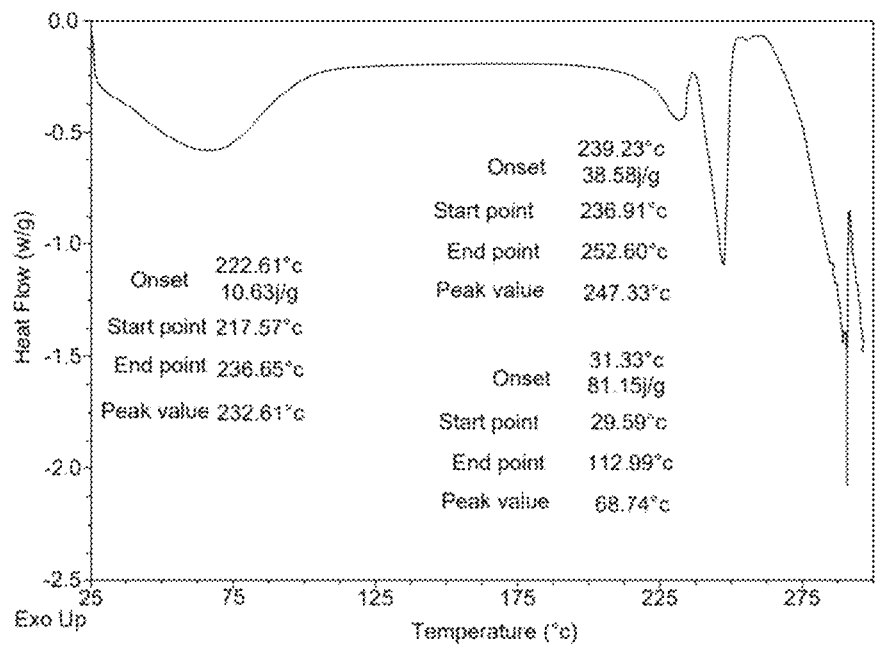
FIG. 31 illustrates the DSC of FT-1518 Esylate crystallized in THF:toluene (1:1) by slurry at 25° C.
Figure 32:
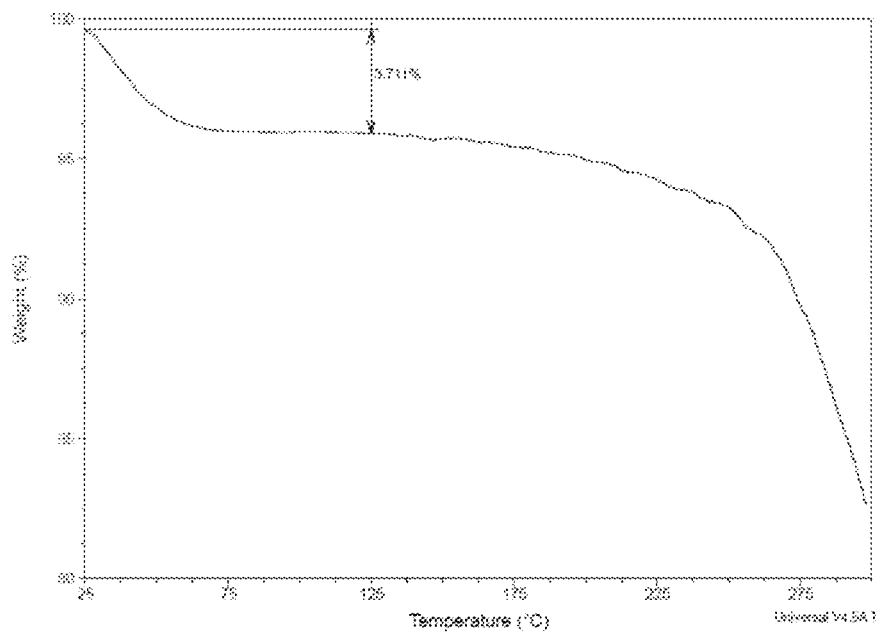
FIG. 32 illustrates the TGA of FT-1518 Esylate crystallized in THF:toluene (1:1) by slurry at 40° C.
Figure 33:
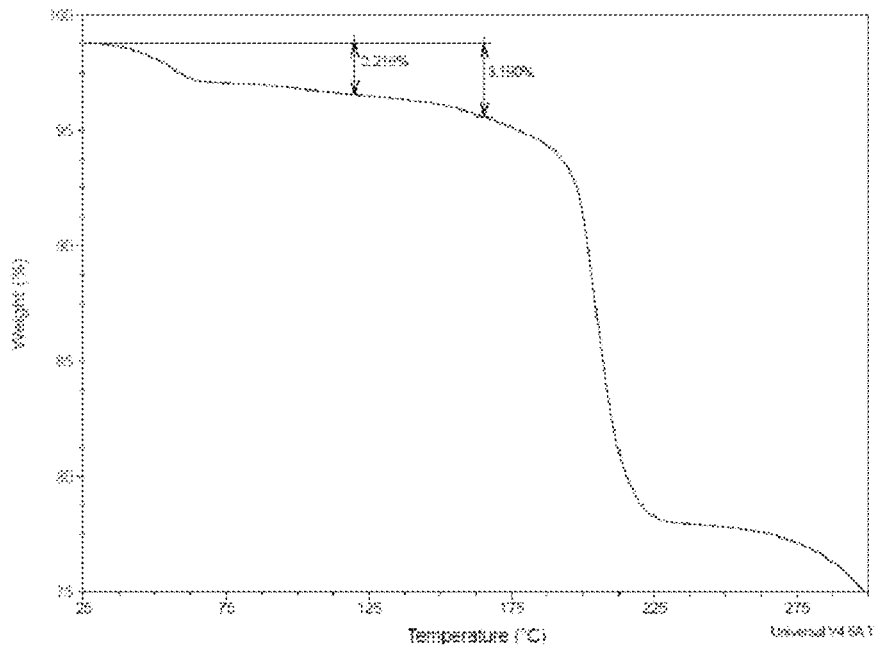
FIG. 33 illustrates the TGA of polymorph screening of FT-1518 Oxalate crystallized by cooling in THF
Figure 34:
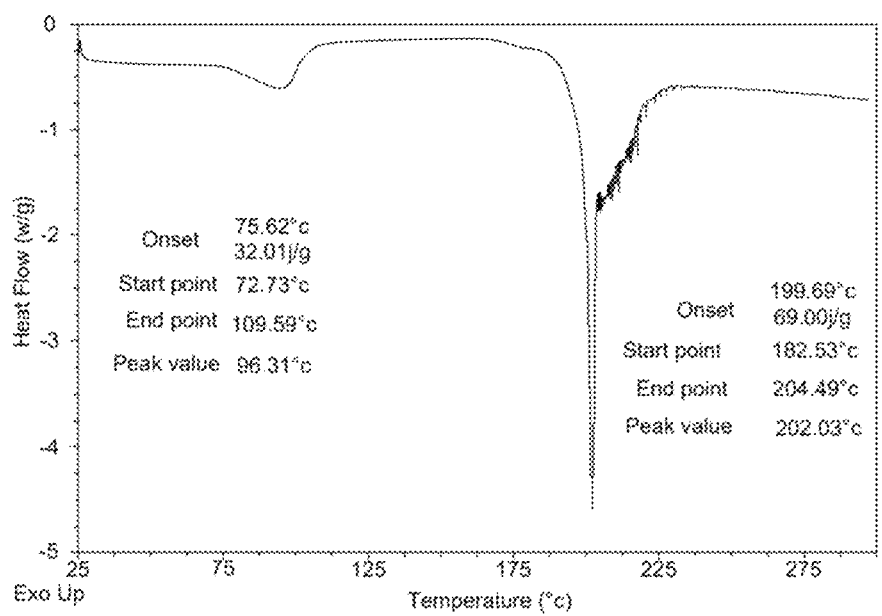
FIG. 34 illustrates the DSC of polymorph screening of FT-1518 Oxalate crystallized by cooling in THF

The experiments performed were listed out in table 18. The solid was isolated from the suspensions at RT (25° C.) and 40° C., air dried and were analysed by DSC, TGA and pXRD. FIG. 25 illustrates PXRD overlay of Esylate slurry transformation experiments at RT. In FIG. 25, XRD patterns 152, 154, 156, and 158 of esylate salts formed by slurry transformation at RT by THF:Toluene (1:1), toluene, THF, and ethyl acetate respectively, are compared with XRD pattern 120 of esylate salt and XRD pattern 100 of FT-1518 base. FIG. 26 and FIG. 27 respectively illustrate TGA and DSC of esylate crystallized in ethyl acetate by slurry at 25° C., and FIG. 28 and FIG. 29 respectively illustrate TGA and DSC of esylate crystallized in tetrahydrofuran by slurry at 25° C. FIG. 30 illustrates TGA of esylate crystallized in toluene by slurry at 25° C., FIG. 31 illustrates DSC of esylate crystallized in tetrahydrofuran:toluene (1:1) by slurry at 25° C., and FIG. 32 illustrates TGA of esylate crystallized in tetrahydrofuran:toluene (1:1) by slurry at 40° C. Results of TGA and DSC studies of various slurry transformation experiments of FT-1518 esylate are summarized in table 19.

TABLE 18

Slurry transformation (hydration) experiments of FT-1518 Esylate

| Samples | volume (mL) | Initial | 1 hr | 7 Days |
| --- | --- | --- | --- | --- |
| slurry at 25° C. | | | | |
| ethyl acetate | 1 | Dispersion | Dispersion | Dispersion |
| THF | 1 | Dispersion | Dispersion | Dispersion |
| toluene | 1 | Dispersion | Dispersion | Dispersion |
| THF:water (90:10) | 1 | soluble | soluble | Solvent evaporated, crystals collected |
| THF:Toluene (1:1) | 1 | Dispersion | Dispersion | Dispersion |
| slurry at 40° C. | | | | |
| THF | 1 | Dispersion | Dispersion | Dispersion |
| toluene | 1 | Dispersion | Dispersion | Dispersion |
| THF:water (90:10) | 1 | soluble | soluble | Solvent evaporated, crystals collected |
| THF:Toluene (1:1) | 1 | Dispersion | Dispersion | Dispersion |

TABLE 19

Results of Slurry transformation experiments of FT-1518 Esylate

| Sample name | DSC | TGA |
|---|---|---|
| Ethyl acetate | Endotherm - 240.58° C., 255° C. (sharp peaks) | 3.261% up to 125° C. |
| Toluene | Endotherm - 88.68° C. (broad), 230.49° C., 246.47° C. (sharp peaks) followed by degradation | 3.661% up to 125° C. |
| THF:toluene (1:1) | Endotherm - 78.65° C. (broad), 228.95° C., 247.44° C. (sharp peaks) followed by degradation | 3.711% up to 125° C. |
| Esylate salt initial | Endotherm - 112.44° C. (broad), 231.19° C., 236.65° C. (sharp) | 0.915% up to 125° C. |
| Free base (FT-1518) | Endotherm −185.37° C. | 0.36% up to 100° C.; 1.58% up to 150° C. |

Summary of Pseudo-Polymorph Form Screening of FT-1518 Esylate:

Slurry at 25° C.: No change in polymorph was observed during the investigation in various slurries. Hence, all the residues obtained may be stable forms in these experiments.

Slurry at 40° C.: No change in polymorph was observed during the investigation in various slurries. There may be possible new form in slurry of ethyl acetate. Even at 25° C., this sample showed a clear split near diffraction angle of 8°.

Physical Form Screening Study of FT-1518 Oxalate

Cooling Crystallization of FT-15185 Oxalate

Weighed quantity (75 mg) of drug substance was dissolved in small amount (enough volume to solubilize API) in solvent by heating at 50-55° C. Clear solutions obtained were kept for evaporation at refrigerated conditions. The experimental conditions in which the cooling crystallisation was performed is mentioned in table 20.

TABLE 20

Cooling crystallization experiments of FT-1518 Oxalate

| Samples | volume (mL) | Initial | 2 days |
|---|---|---|---|
| Tetrahydrofuran (THF) | 5 | soluble | Crystals formed |
| methanol | 8 | soluble | Crystals formed |
| ethanol | 8 | soluble | Crystals formed |
| Acetonitrile | 1.3 | soluble | Crystals formed |

Figure 35:
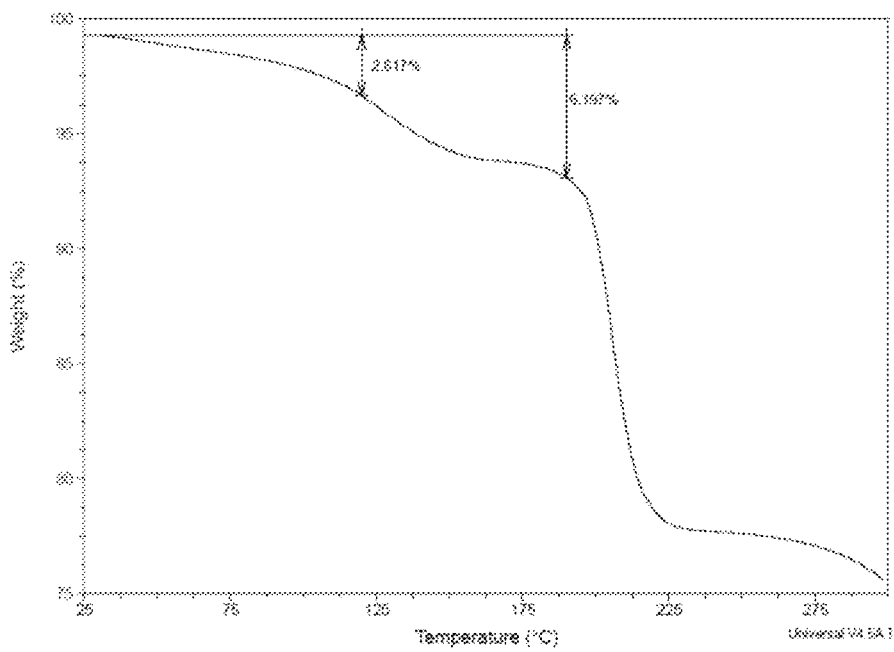
FIG. 35 illustrates the TGA of polymorph screening of FT-1518 Oxalate crystallized by cooling in Methanol
Figure 36:
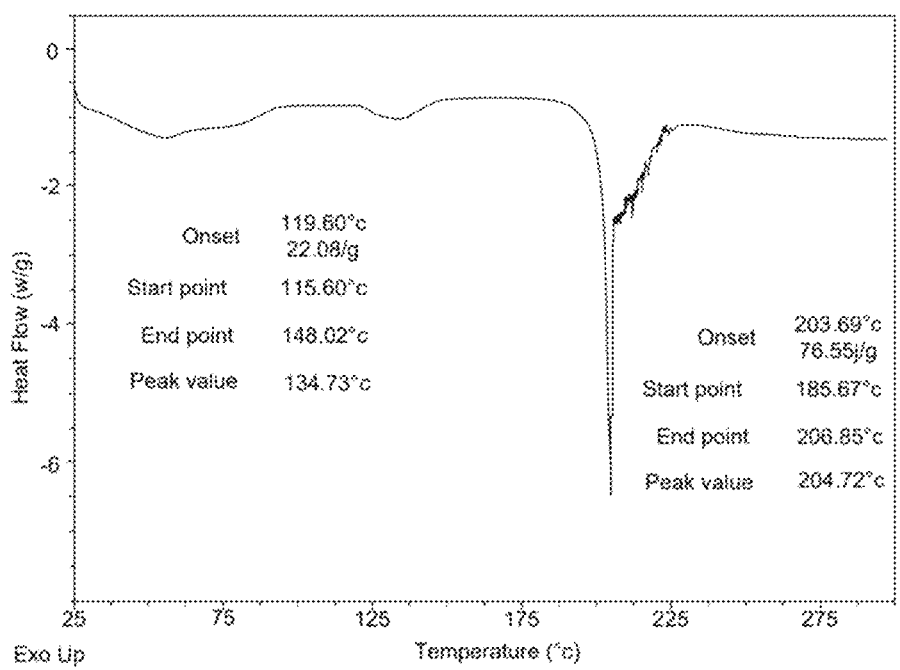
FIG. 36 illustrates the DSC of polymorph screening of FT-1518 Oxalate crystallized by cooling in Acetonitrile
Figure 37:
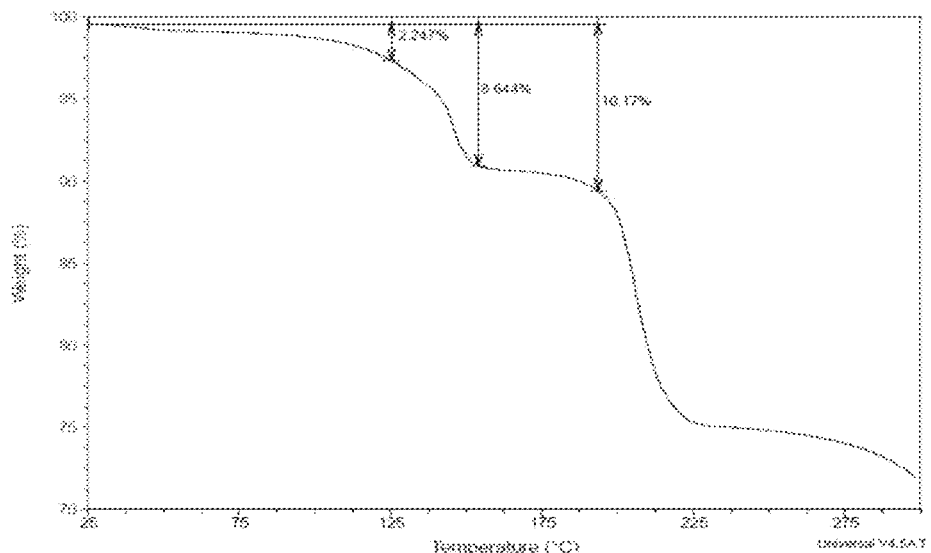
FIG. 37 illustrates the TGA of polymorph screening of FT-1518 Oxalate crystallized by cooling in ethanol

PXRD confirmed polymorph screening of FT-1518 oxalate by cooling crystallization. TGA and DSC of physical form screening samples by cooling crystallization experiment are shown in FIGS. 33-37. For example, FIGS. 33 and 34 respectively illustrate TGA and DSC of polymorph screening of FT-1518 Oxalate crystallized by cooling in tetrahydrofuran, FIG. 35 illustrates the TGA of polymorph screening of FT-1518 Oxalate crystallized by cooling in Methanol, FIG. 36 illustrates the DSC of polymorph screening of FT-1518 Oxalate crystallized by cooling in acetonitrile, and FIG. 37 illustrates the TGA of polymorph screening of FT-1518 Oxalate crystallized by cooling in ethanol. Results of TGA and DSC studies of various cooling crystallization experiments of FT-1518 oxalate are summarized in table 21.

TABLE 21

Results of cooling crystallization experiments of FT-1518 Oxalate

| Sample name | DSC | TGA |
|---|---|---|
| THF | Endotherms - 96.31° C. (broad), 202.03° C. (sharp) followed by degradation | 2.216% up to 125° C. 3.190% up to 175° C. |
| Methanol | Endotherms - 135.52° C. (broad), 204.23° C. (sharp) followed by degradation | 2.617% up to 125° C. 6.197% up to 180° C. |
| Acetonitrile | Endotherms - 134.73° C., 204.73° C. (sharp) followed by degradation | 5.404% up to 125° C. 6.182% up to 180° C. |
| Ethanol | Endotherms - 153.13° C., 204.07° C. (sharp) followed by degradation | 2.247% up to 125° C. 8.644% up to 150° C. 10.17% up to 175° C. |
| Oxalate Salt initial | Endotherm −117.95° C. (broad), degradation from around 170° C. | 0.4454% up to 125° C. |
| Free base (FT-1518) | Endotherm −185.37° C. | 0.36% up to 100° C.; 1.58% up to 150° C. |

Summary of Polymorph Screening of FT-1518 Oxalate by Cooling Crystallization:

Results of cooling crystallisation of FT-1518 Oxalate are summarized in table 46. New forms may have formed in crystallized samples of methanol, acetonitrile and ethanol. This was corroborated by new diffraction patterns in PXRD and change in DSC.

Solvent Evaporation Screening of FT-1518 Oxalate

Figure 38:
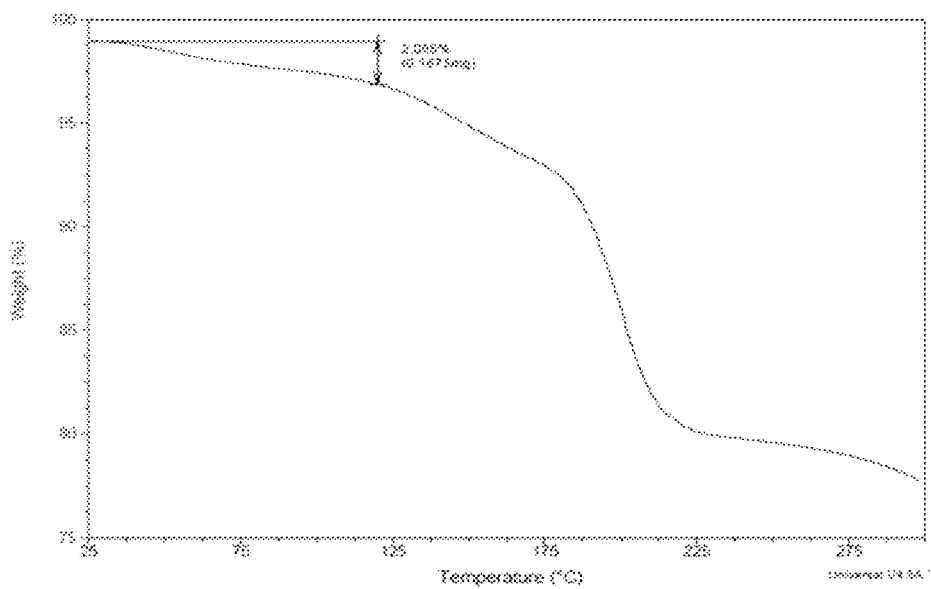
FIG. 38 illustrates the TGA of FT-1518 Oxalate crystallized using methanol by solvent evaporation
Figure 39:
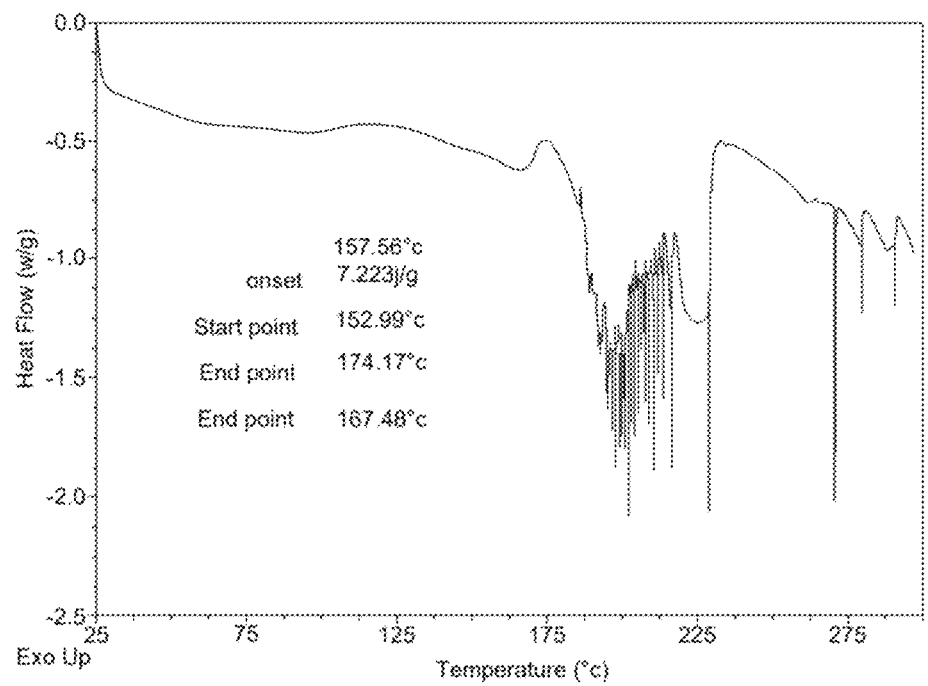
FIG. 39 illustrates the DSC of FT-1518 Oxalate crystallized using methanol by solvent evaporation
Figure 40:
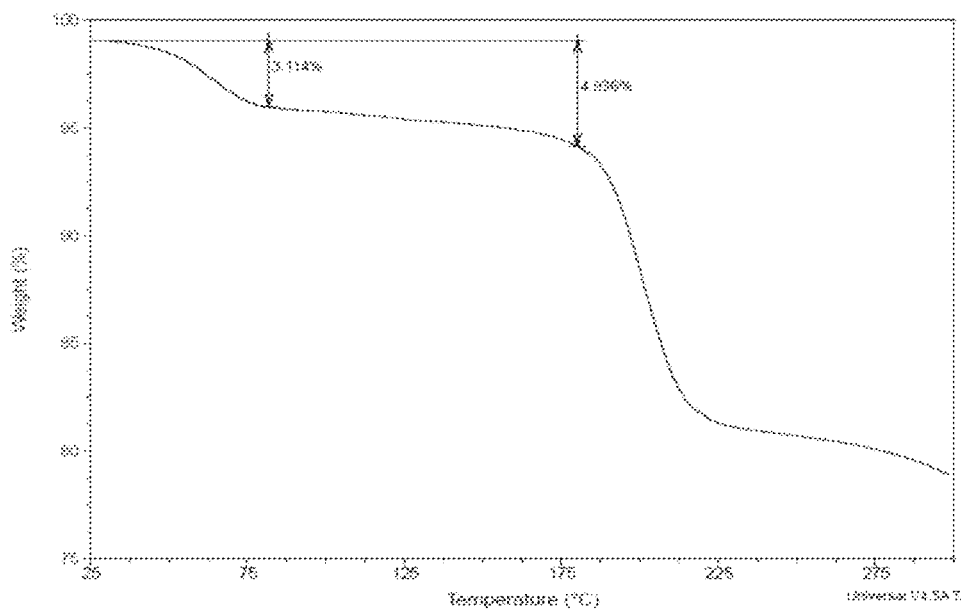
FIG. 40 illustrates the TGA of FT-1518 Oxalate crystallized using acetonitrile by solvent evaporation
Figure 41:
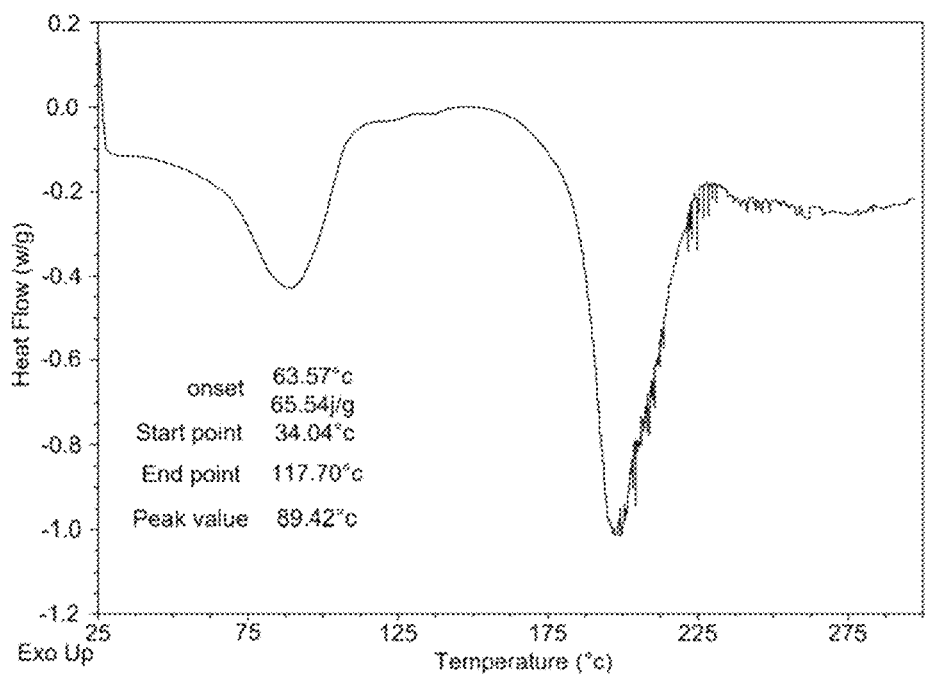
FIG. 41 illustrates the DSC of FT-1518 Oxalate crystallized using acetonitrile by solvent evaporation
Figure 42:
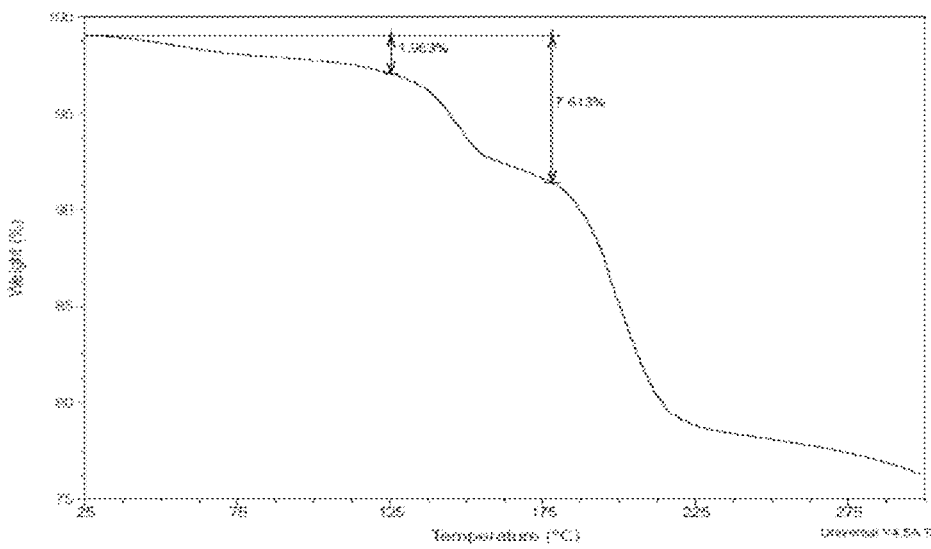
FIG. 42 illustrates the TGA of FT-1518 Oxalate crystallized using ethanol by solvent evaporation
Figure 43:
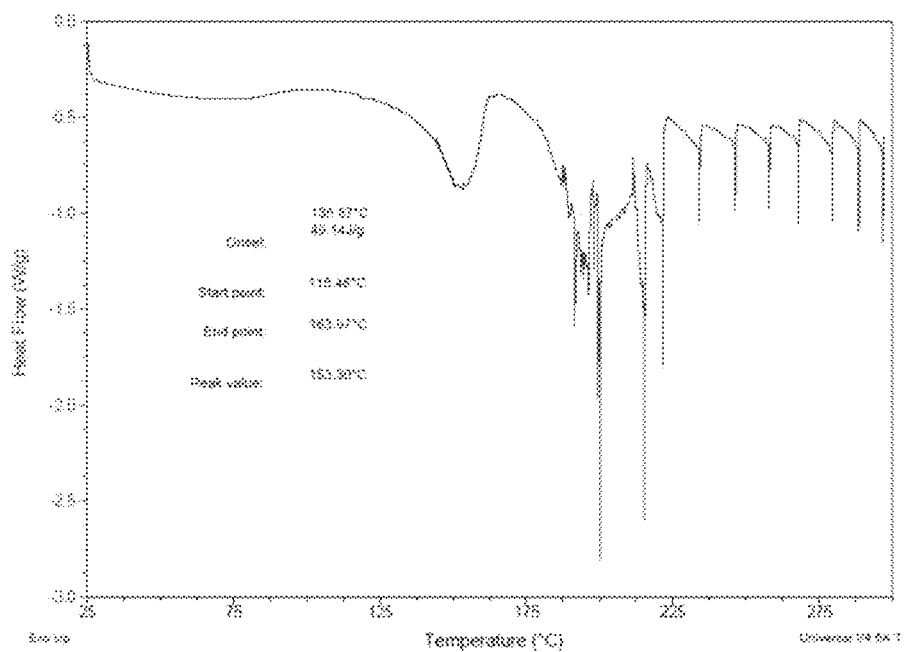
FIG. 43 illustrates the DSC of FT-1518 Oxalate crystallized using ethanol by solvent evaporation

The compound (about 75 mg) was dissolved in various solvents by heating at 50-55° C. to prepare solutions. Then, heated at 50° C. on a hot plate to evaporate solvent to concentrate the solution and let it at room temperature until complete solvent evaporated or recrystallization to occur with concentration. The details of the experiment are mentioned in the table 22. PXRD confirmed physical form screening of FT-1518 oxalate by solvent evaporation. FIGS. 38 and 39 respectively illustrate TGA and DSC of FT-1518 Oxalate crystallized by using methanol by solvent evaporation, FIGS. 40 and 41 respectively illustrate TGA and DSC of FT-1518 Oxalate crystallized by using acetonitrile by solvent evaporation, and FIGS. 42 and 43 respectively illustrate TGA and DSC of FT-1518 Oxalate crystallized by using ethanol by solvent evaporation. The results of TGA and DSC of FT-1518 oxalate crystallized by solvent evaporation are summarized in table 23.

TABLE 22

Solvent evaporation experiments of FT-1518 Oxalate

| Samples | volume (mL) | Initial | 1 hour | 2 days |
|---|---|---|---|---|
| Acetone | 20 | soluble | precipitate | Crystals formed |
| 1,4-dioxane | 10 | soluble | precipitate | Crystals formed |
| THF | 5 | soluble | soluble | Crystals formed |
| methanol | 8 | soluble | soluble | Crystals formed |
| ethanol | 8 | soluble | soluble | Crystals formed |
| Acetonitrile | 1.3 | soluble | soluble | Crystals formed |

TABLE 23

Solvent evaporation experiments of FT-1518 Oxalate

| Sample name | DSC | TGA |
|---|---|---|
| Ethanol | Endotherms - 153.30° C. (broad), followed by degradation | 1.963% up to 125° C. 7.613% up to 175° C. |
| THF | Endotherms - 97.83° C. (broad), 109.3° C. | 4.533% up to 125° C., 6.815% up to 180° C. |
| Acetonitrile | Endotherms - 89.42° C. (broad) | 3.114% up to 80° C., 4.936% up to 175° C. |
| Methanol | Endotherms - 167.48° C. (broad and small) followed by degradation | 2.085% up to 125° C. |
| Acetone | Endotherms - 95.41° C. (broad), followed by degradation from about 170° C. | 3.552% up to 125° C., 6.025% up to 175° C. |
| Oxalate salt initial | Endotherm −117.95° C. (broad), degradation from around 170° C. | 0.4454% up to 125 ° C. |
| Free base | Endotherm −185.37° C. | 0.36% up to 100° C.; 1.58% up to 150° C. |

Summary of Polymorph Screening of FT-1518 Oxalate by Solvent Evaporation:

The solvent evaporation experiments for oxalate salt of FT-1518 were performed in various solvents. The results obtained from PXRD and DSC showed that some polymorphic changes were observed in samples obtained from THF, methanol, 1,4-dioxane and ethanol.

Slurry Transformation Experiments of FT-1518 Oxalate

Figure 44:
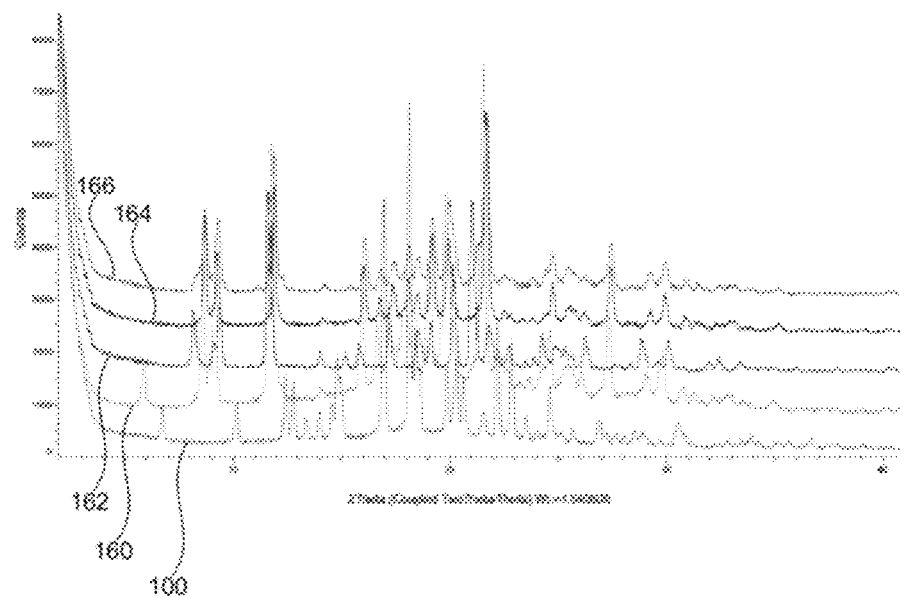
FIG. 44 illustrates the PXRD results of FT-1518 Oxalate slurry transformation experiments at RT
Figure 45:
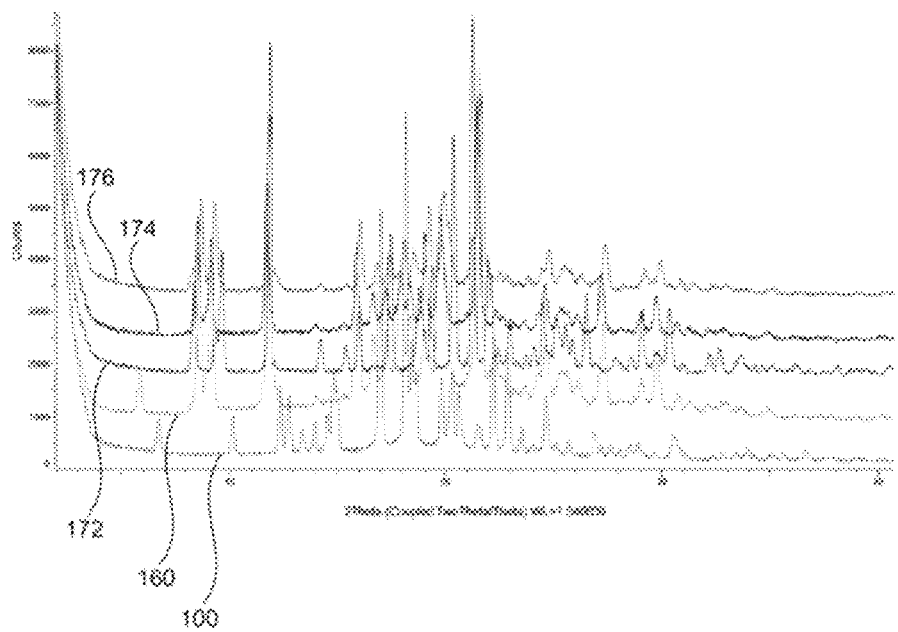
FIG. 45 illustrates the PXRD results of FT-1518 Oxalate slurry experiments at 40° C.
Figure 46:
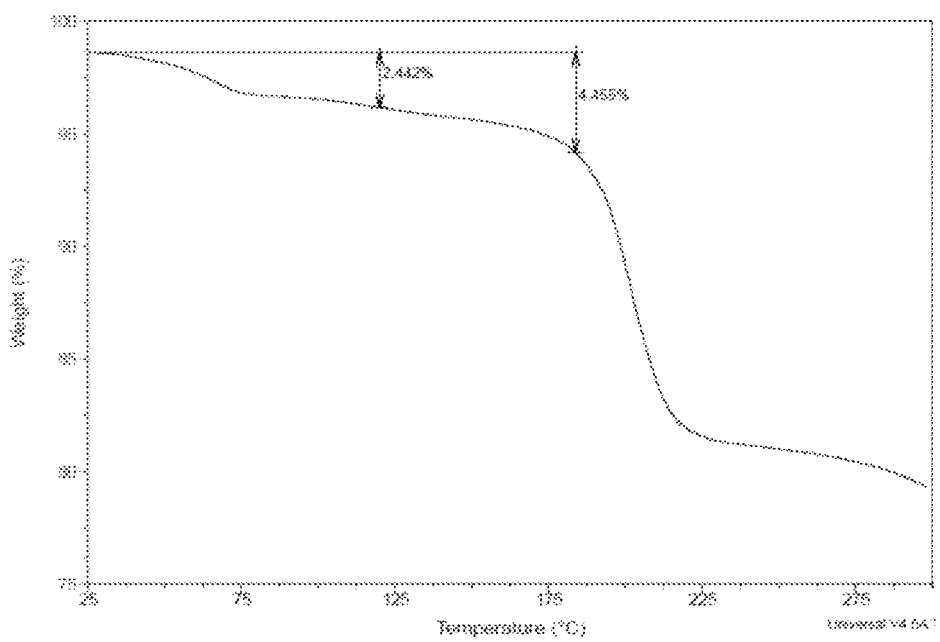
FIG. 46 illustrates the TGA results of FT-1518 Oxalate slurried at 25° C. in n-hexane
Figure 47:
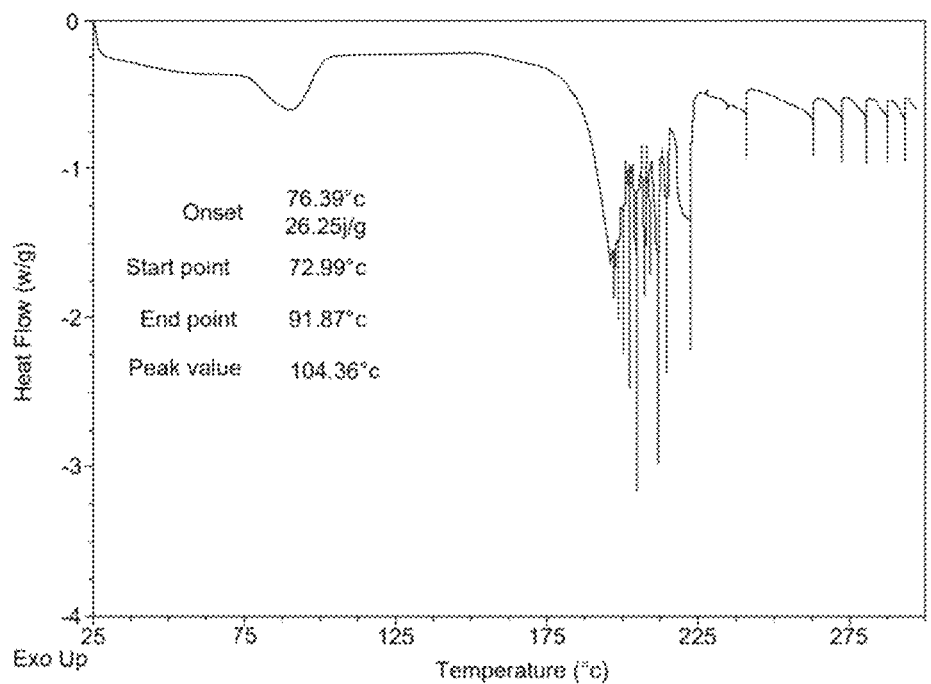
FIG. 47 illustrates the DSC results of FT-1518 Oxalate slurried at 25° C. in n-hexane
Figure 48:
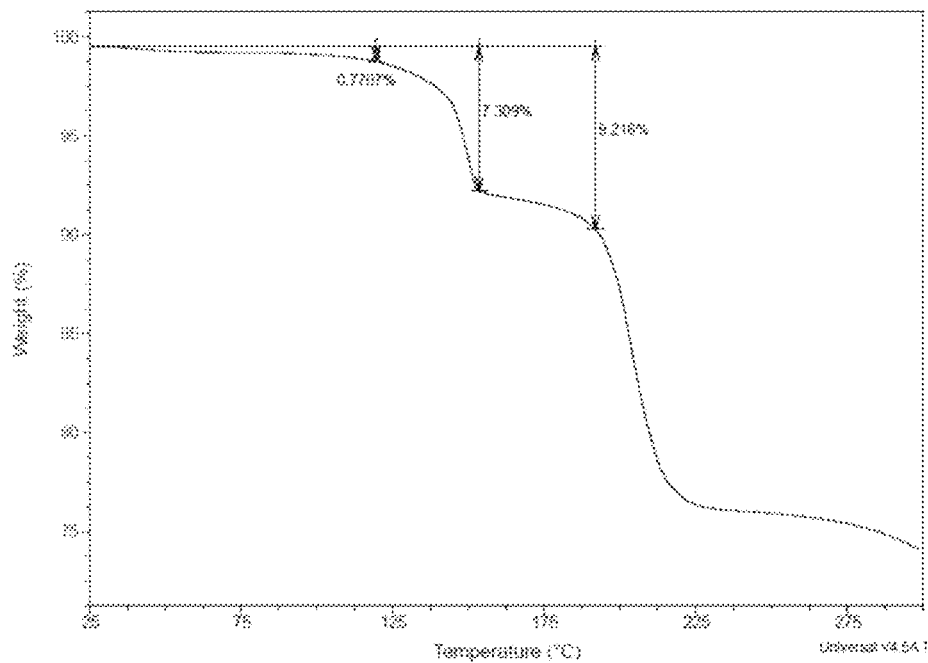
FIG. 48 illustrates the TGA results of FT-1518 Oxalate slurried at 25° C. in ethyl acetate:water (9:1)
Figure 49:
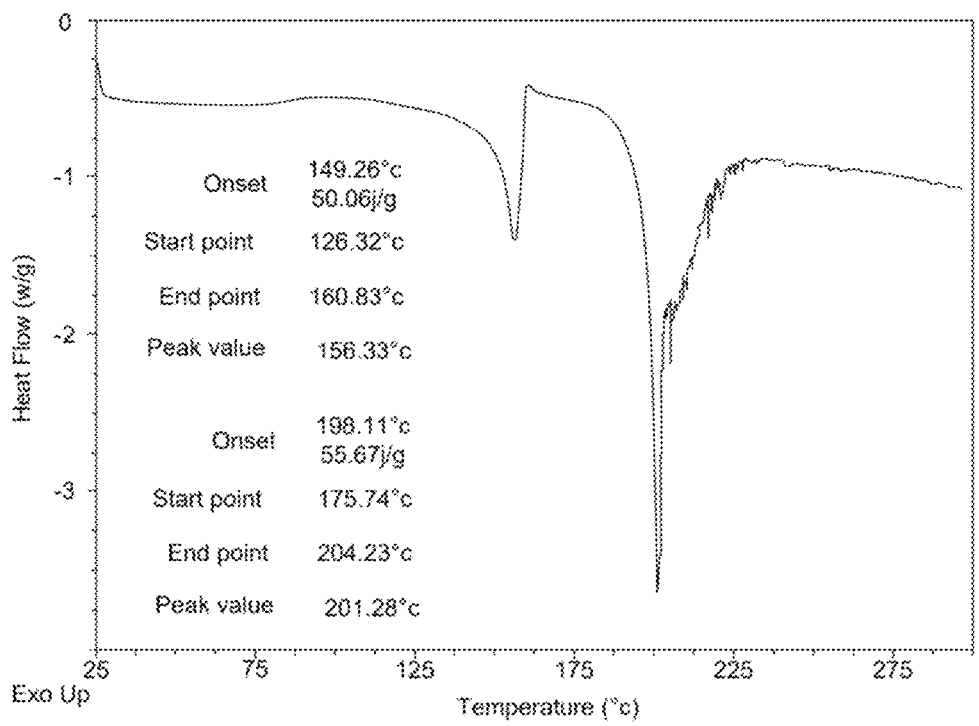
FIG. 49 illustrates the DSC results of FT-1518 Oxalate slurried at 25° C. in ethyl acetate:water (9:1)
Figure 50:
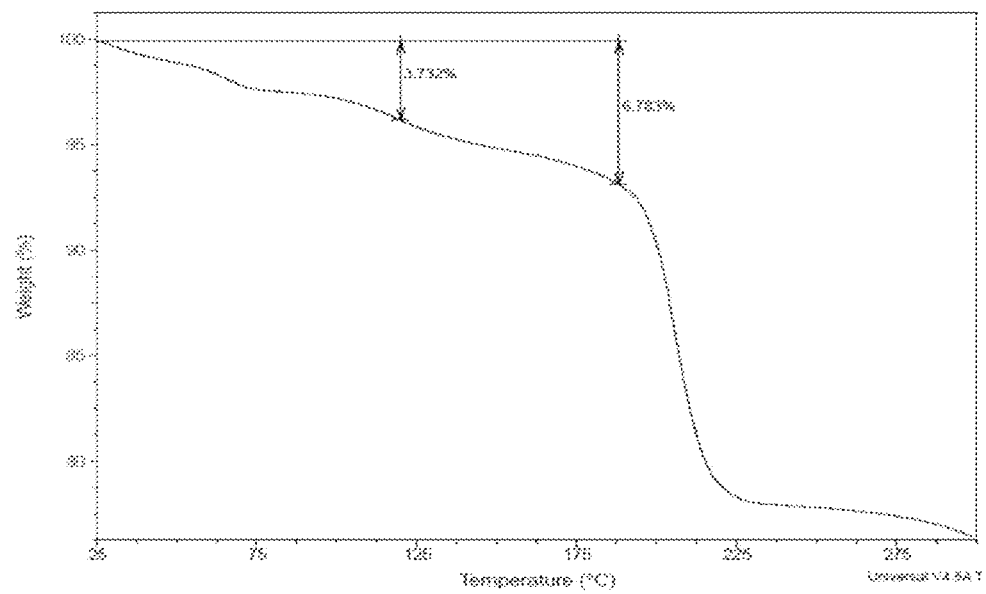
FIG. 50 illustrates the TGA results of FT-1518 Oxalate slurried at 40° C. in ethyl acetate
Figure 51:
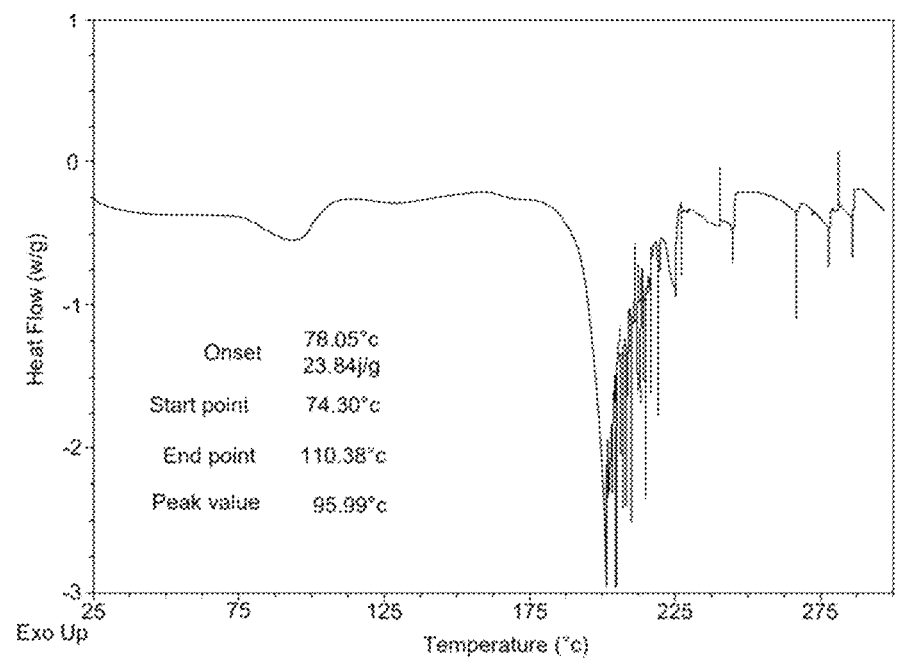
FIG. 51 illustrates the DSC results of FT-1518 Oxalate slurried at 40° C. in ethyl acetate
Figure 52:
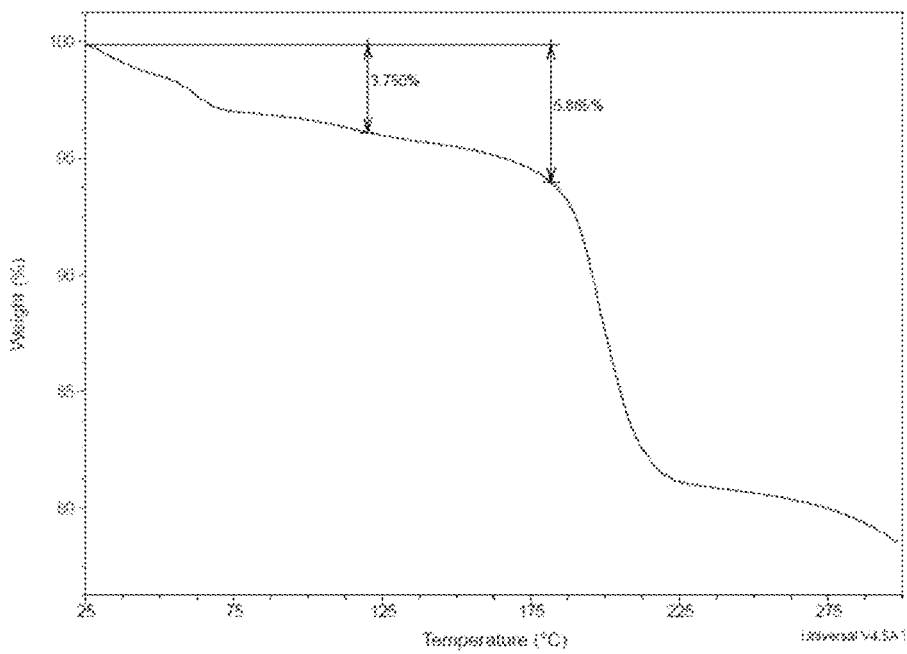
FIG. 52 illustrates the TGA results of FT-1518 Oxalate slurried at 40° C. in n-hexane.
Figure 53:
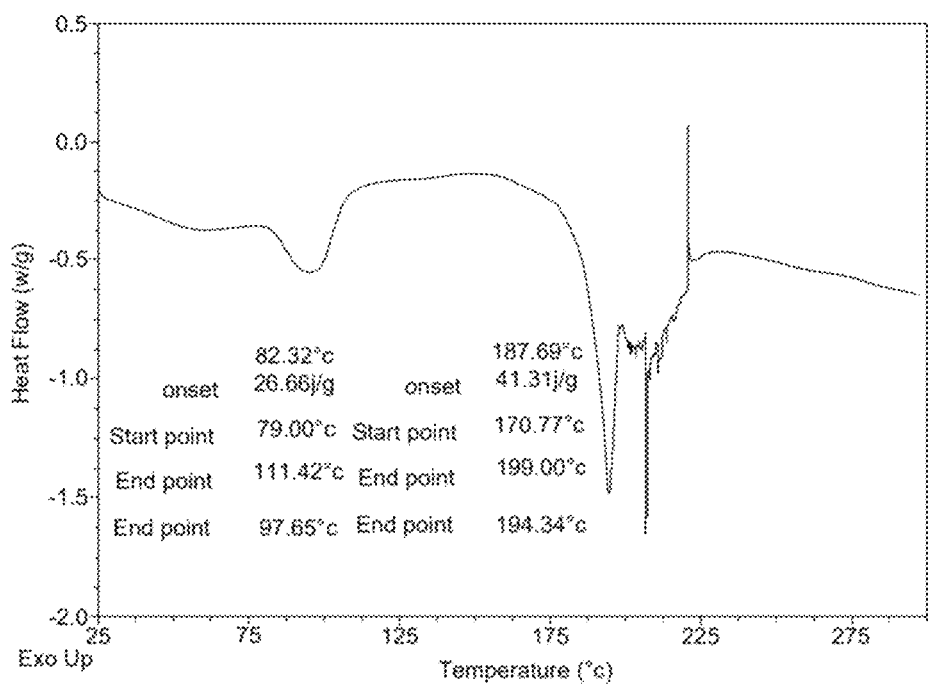
FIG. 53 illustrates the DSC results of FT-1518 Oxalate slurried at 40° C. in n-hexane.
Figure 54:
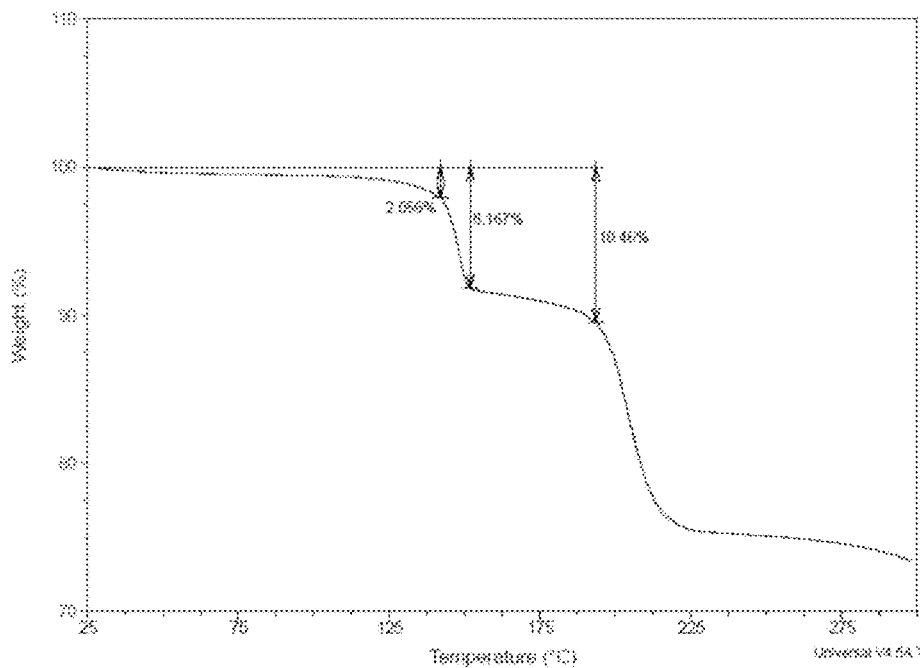
FIG. 54 illustrates the TGA results of FT-1518 Oxalate slurried at 40° C. in ethyl acetate:water (9:1)
Figure 55:
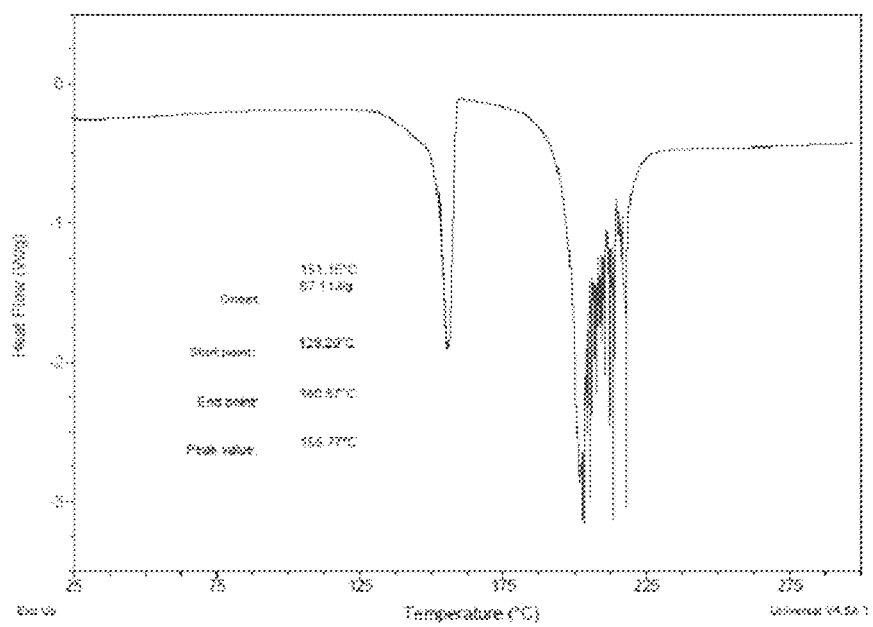
FIG. 55 illustrates the DSC results of FT-1518 Oxalate slurried at 40° C. in ethyl acetate:water (9:1)

The pseudo polymorph (solvate or hydrate) formation propensity of the compound was evaluated in few solvents. The drug substance (about 75 mg) was dispersed in the solvents and subjected for slurry transformation at 25° C. and 40° C. for a period of 7 days using bottle rotating apparatus with excess amount of drug substance. The experimentation details are shown in table 24. Results of PXRD studies of FT-1518 Oxalate slurry transformation experiments at RT is shown in FIG. 44, and FIG. 45 illustrates PXRD result of FT-1518 Oxalate slurry experiments at 40° C. In FIG. 44, XRD patterns 162, 164, and 166 of oxalate salts formed by slurry transformation at RT by ethyl acetate:water (90:10), n-hexane, and ethyl acetate respectively, are compared with XRD pattern 160 of oxalate salt and XRD pattern 100 of FT-1518 base. In FIG. 45, XRD patterns 172, 174, and 176 of oxalate salts formed by slurry transformation at 40° C. by ethyl acetate:water (90:10), n-hexane, and ethyl acetate respectively, are compared with XRD pattern 160 of oxalate salt and XRD pattern 100 of FT-1518 base. FIGS. 46 and 47 respectively illustrate TGA and DSC of FT-1518 Oxalate slurried at 25° C. in n-hexane, and FIGS. 48 and 49 respectively illustrate TGA and DSC of FT-1518 Oxalate slurried at 25° C. in ethyl acetate:water (9:1). FIGS. 50 and 51 respectively illustrate TGA and DSC of FT-1518 Oxalate slurried at 40° C. in ethyl acetate, FIGS. 52 and 53 respectively illustrate TGA and DSC of FT-1518 Oxalate slurried at 40° C. in n-hexane, and FIGS. 54 and 55 respectively illustrate TGA and DSC of FT-1518 Oxalate slurried at 40° C. in ethyl acetate:water (9:1). Results of TGA and DSC were shown in Table 25.

TABLE 24

Slurry transformation (solvate formation) experiments of FT-1518 Oxalate

| Samples | Volume (mL) | Initial | 1 hour | 4 days |
|---|---|---|---|---|
| slurry at 25° C. | | | | |
| ethyl acetate | 1 | Dispersion | Dispersion | Dispersion |
| n-hexane | 1 | Dispersion | Dispersion | Dispersion |
| ethyl acetate: water (90:10) | 1 | Dispersion | Dispersion | Turned into solution |
| slurry at 40° C. | | | | |
| ethyl acetate | 1 | Dispersion | Dispersion | Dispersion |
| n-hexane | 1 | Dispersion | Dispersion | Dispersion |
| ethyl acetate: water (90:10) | 1 | Dispersion | Dispersion | Turned in to solution |

TABLE 25

Results of Slurry transformation experiments of FT-1518 Oxalate at 40° C.

| Sample name | DSC | TGA |
|---|---|---|
| Ethyl acetate | Endotherm - 95.99° C., degradation from about 170° C. | 3.732% up to 125° C. 6.783% up to 180° C. |
| n-hexane | Endotherm - 97.65° C. (broad), 194.34° C. (sharp peaks) followed by degradation | 3.750% up to 125° C., 5.885% up to 175° C. |
| Ethyl acetate: water (90:10) | Endotherm - 155.77° C. (sharp) followed by degradation | 2.056% up to 125° C., 8.167% up to 150° C., 10.46% up to 190° C. |
| Oxalate salt initial | Endotherm −117.95° C. (broad), degradation from around 170° C. | 0.4454% up to 12° C. |
| Free base (FT-1518) | Endotherm −185.37° C. | 0.36% up to 100° C.; .58% up to 150° C. |

Summary of Solvate Form Screening by Slurry Transformation of FT-1518 Oxalate:

Slurry at 25° C.: There may be possibility of new polymorphic form in ethyl acetate:water (90:10) slurry sample at 25° C. In ethyl acetate and n-hexane, the residues obtained may be stable forms in these experiments.

Slurry at 40° C.: There may be possibility of new polymorphic form in ethyl acetate:water (90:10) slurry sample at 40° C. which is similar to that obtained at 25° slurry. In ethyl acetate and n-hexane, the residues obtained may be stable forms in these experiments.

Patterns Assigned for Esylate and Oxalate Salts of FT-1518

Various patterns were assigned for the crystallized samples from different screening experiments to identify physical forms of Esylate and oxalate salts of FT-1518 in tablet no. 26 and 27 respectively.

TABLE 26

Patterns assigned for FT-1518 Esylate

| Pattern no. | Solvent Evaporation | Slurry at 25° C. | Slurry at 40° C. | Cooling crystallization |
|---|---|---|---|---|
| 1 (Initial pattern of salt prepared and most occurred one) | THF, acetone, ethanol, acetonitrile, Methanol, THF:water (9:1) | THF, Toluene, THF: toluene (1:1) | THF, Toluene, THF: toluene (1:1) | — |
| 2 (metastable form also exists at room temp. and converts into stable after recrystallization) | — | Ethyl acetate | Ethyl acetate | DCM, ethanol |
| 3 (stable polymorph) | — | — | — | Methanol (has only single melting point indicating endotherm at around 259° C.) |

TABLE 27

Patterns assigned for FT-1518 oxalate

| Pattern no. | Solvent Evaporation | Slurry at 25° C. | Slurry at 40° C. | Cooling crystallization |
|---|---|---|---|---|
| Form-A (Initial pattern of salt prepared) | Acetone (95° C. broad), Acetonitrile (89° C. broad), Ethanol (153° C. broad) THF (partially amorphous) (97° C., 109° C. broad) | Ethyl acetate (98° C. broad, 199° C. sharp) n-hexane (104° C. broad) | Ethyl acetate (95° C. broad) n-hexane (97° C. broad, 194° C. sharp) | Acetonitrile (134° C. sharp, 204° C. sharp) THF (96° C. broad, 202° C. sharp) |
| Form-B | 1,4-dioxane (151° C. sharp) | — | — | — |
| Form-C | Methanol (167° C. broad and small) | — | — | Methanol (135° C. broad, 204° C. sharp), Ethanol (153° C. broad, 204° C. sharp) |
| Form-D (form was stable even after exposed to 40° C./75% RH for 2 weeks) | — | Ethyl acetate:water (9:1) (156° C., 201° C. sharp) | Ethyl acetate water (9:1) (155° C. sharp) | — |

Solid State Stability

Stability Study Design

Physical forms crystallized from various methods of crystallization were exposed to 40° C./75% RH for 7 days in open condition to understand the physical stability of the new physical forms in the presence of heat and humidity and also to know if there is any form conversion in the stable forms of Esylate and oxalate salts of FT-1518.

The study design is summarized in table 28.

TABLE 28

Study design for solid state stability of FT-1518 Esylate and oxalate salts

| storage conditions | 1 week |
|---|---|
| 40° C. ± 2° C./75% ± 5% RH, Open | √ |

√ = pXRD

Results of Stability Study

The results of solid state stability study of various physical forms of esylate and oxalate salts of FT-1518 with respect to heat and humidity evaluated by pXRD is summarized in table 29 and 30 respectively.

TABLE 29

Results of solid state stability of FT1518 Esylate

| Solvent | Cooling crystallization | Solvent evaporation | Slurry transformation |
| --- | --- | --- | --- |
| Ethanol | Newly physical form remained the same | formed Same as initial salt | — |
| dichloromethane | Form changed from crystallised sample | New physical form converted back to initial salt form | — |
| Methanol | — | Same as initial salt | — |
| Acetonitrile | — | Same as initial salt | — |
| THF:water (9:1) | — | Same as initial salt | — |
| Toluene | — | — | Same as initial salt |
| Ethyl acetate | — | — | Form obtained in 40° C. slurry converted back to initial salt form |
| THF | — | — | Same as initial salt |
| THF: toluene (1:1) | — | — | Same as initial salt |

TABLE 30

Results of solid state stability of FT1518 oxalate

| Solvent | Cooling crystallization | Solvent evaporation | Slurry transformation |
| --- | --- | --- | --- |
| Tetrahydrofuran | Same as initial salt | Major conversion of new form obtained happened in to initial salt form. Complete conversion may require some | — |
| Methanol | Form obtained from methanol crystallisation converted back to initial salt form | — | more time |
| Acetonitrile | Form obtained from methanol crystallisation converted back to initial salt form | Same as initial salt | — |
| Ethanol | Same as initial salt | Partial conversion of new form obtained happened in to initial salt form. Complete conversion may require some more time | — |
| Acetone | — | Same as initial salt form | — |
| Hexane | — | — | Same as initial salt form |
| Ethyl acetate | — | — | Same as initial salt form |
| Ethyl acetate: water (9:1) | — | — | New form obtained remained same |

Summary of Stability Study of Physical Forms of FT-1518 Salts:

FT-1518 Esylate salt showed very less risk of polymorphism based on experiments performed to understand the polymorphism risk and its effect on the stability.

Ft-1518 oxalate salt showed few polymorphs or physical forms when recrystallized in various solvents using various crystallization techniques. But, only in ethyl acetate:water (9:1) slurry, the new physical form persisted even after stability study at 40° C./75% RH Inference of Salt Screening, Physical Form Screening and Selection Salt Screening Various salt screening experiments were explored using acidic counterions to evaluate the salt forming affinity/propensity of FT-1518.

The salt formation was confirmed primarily by PXRD and proton NMR. The results and observations of salt screening trials showed that there was feasibility of formation of tosylate, adipate, mesylate, malate, phthalate, fumarate, succinate, oxalate, maleate, nitrate, tartarate, malonate, camphor sulfonate, esylate, besylate, sulphate, and hydrochoride salts.

Preparation of salts such as esylate, besylate, HCl, sulfonate, nitrate can be done by using precipitation from common solvent (here Tetrahydrofuran). Preparation of remaining salts among the confirmed can be prepared by solvent evaporation (slow) in a common solvent (acetone).

Based on the salt screening results, scale up of all the confirmed salts will be performed at around 100-200 mg scale and complete characterisation of each salt will be conducted. Solubility of salt in 10 mM potassium dihydrogen phosphate buffer (pH 6.8) & % purity (HPLC), crystallinity (PXRD), proton NMR, hygroscopicity & pseudopolymorph propensity (Dynamic Vapour Sorption), melting point & thermal events (DSC), % weight loss before melting point maximum up to 150° C. (TGA) will be conducted to completely characterise the salt. This compilation of characterisation of all the salts will be used for primary salt selection for polymorph screening and stability studies.

Physical Form Screening of Selected Salts (Esylate and Oxalate Salts)

The polymorph screening of the FT-1518 esylate and oxalate confirmed that there are few new physical forms identified in the experiments.

FT-1518 Esylate formed majorly three forms, form-1, form-2 and form-3. Based on the stability study, form-1 of FT-1518 esylate can be confirmed as most commonly existing physical form. Form-2 obtained from solvents (ethyl acetate and DCM) except ethanol and form-3 converted back to the initial salt form that is form-1 when exposed to heat and humidity at 40° C./75% RH for 7 days. Only form-2 obtained from cooling crystallization in ethanol remained same after stability study.

FT-1518 oxalate salt was identified and isolated as 4 physical forms, which were named as form-A, form-B, form-C and form-D. Many of these forms converted back to the initial salt form that is form-A during the stability study when exposed to heat and humidity at 40° C./75% RH for 7 days. Only form-D obtained from ethyl acetate:water (9:1) slurries remained same during this period.

Selection of Suitable Physical Forms of Esylate and Oxalate Salts of FT1518

FT-1518 Esylate salt showed very less risk of polymorphism based on experiments performed to understand the polymorphism risk and its effect on the stability. But, based on stability studies of the physical forms.

Ft-1518 oxalate salt showed few polymorphs or physical forms when recrystallized in various solvents using various crystallization techniques. But, only in ethyl acetate:water (9:1) slurry, the new physical form persisted even after stability study at 40° C./75% RH Based on the stability studies of various physical forms of both salts and various crystallisation processes in solvents of different polarity (ranging from non-polar to polar) of the physical forms of the both salts (esylate and oxalate of FT-1518), Form-1 (pattern-1) of esylate and form-A of oxalate seems to be most occurring and stable forms.

The better salt for the further development will be selected based on the above study of physical form selection of salt and pharmacokinetic study (being conducted by FTG).

Brief Outline of Experiments Conducted:

The In vitro and in vivo experiments were carried out at Vipragen Biosciences Pvt Ltd (India), Mysore. The animals were procured from Adita Biosys, Bangalore (India). All experimental animal protocols were approved by Institutional Animal Ethics Committee (IAEC). The experiments were conducted as per the recommendation of the Committee for the Purpose of Control and Supervision of Experiments on Animals (CPCSEA) guidelines for laboratory animal facility published in the gazette of India, Dec. 15, 1998.

Pharmacokinetic Workflow:

The husbandry conditions were maintained as described in animal facility SOPs during the study period. Animals procured were quarantined for 7 days followed by acclimatization for 5 days. The study was carried out for two days. Male Balb/c mice of age 10-12 weeks (18-25 g) and male Sprague Dawley rats 8-10 weeks (220-280 g) were used. The food was with held for a period of 4-12 hr prior to dosing and returned to all animals 4h post dosing and water supplied ad libitum. The doses of FT1518 were as follows: Mice: 10 mg/kg intravenous (i.v) and 50 mg/kg oral (p.o); rat—5 mg/kg intravenous (i.v) and 10 mg/kg oral (p.o). The formulation used in i.v and p.o studies were 10% dimethylsulfoxide (DMSO)+30% polyethyleneglycol 400 (PEG400)+60% water and 0.5% methylcellulose (MC)+0.1% tween 80. Blood was collected at the predetermined time points in mice (cardiac puncture) and Jugular vein (rats) over a period of 24h in eppendorf tubes containing $K_2EDTA$ as anticoagulant. The plasma was isolated from the blood and stored at −80° C. until bioanalysis.

In Vitro Tests Workflow:

All in vitro experiments like protein binding, microsomal stability, cell cytotoxicity were performed as per study protocols of respective experiments.

Intravenous and Per Oral Pharmacokinetic Profile of FT1518 (Base); FT1518-Esylate Salt and FT1518-Oxalate Salt in Male Balb/c Mice Species: BALB/C mice Gender: Male Dose: IV (10 mg/kg), Single dose PO (50 mg/kg), single dose Formulation:

IV—DMSO: PEG400:Water (10:30:60 v/v)

PO— 0.5% methylcellulose and 0.1% Tween 80 in water

Sampling Time Points:

IV: 5 min, 30 min, 1 h, 2, 4, 8 and 24 h post dose

PO: 10 min, 30 min, 1 h, 2, 4, 8 and 24 h post dose.

Figure 56:
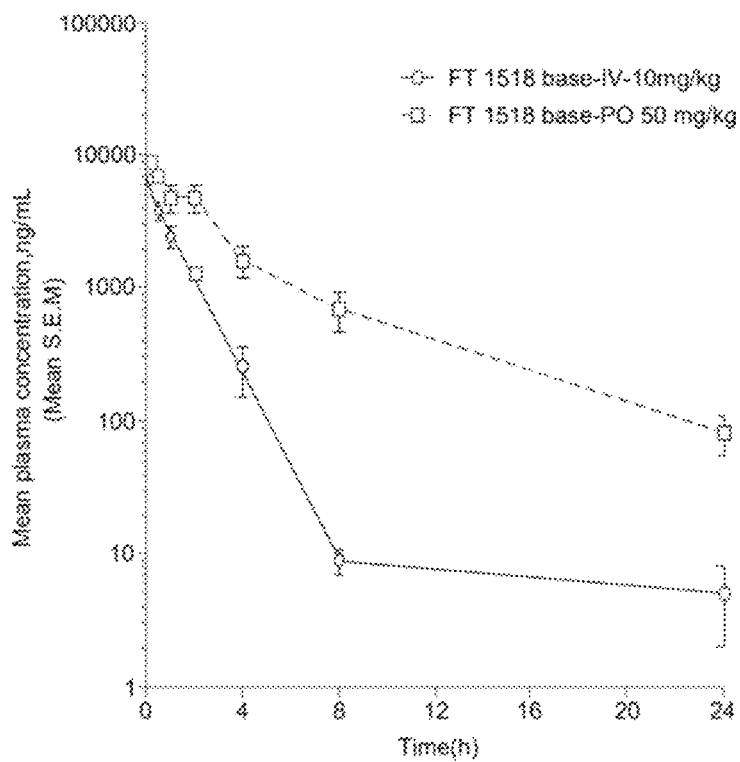
FIG. 56 illustrates pharmacokinetic profile of FT-1518 base in mice.

PK analysis: Phoenix software (Pharsight product). Non-compartmental Analysis (NCA) was used to estimate the PK parameters. FIG. 56 depicts a pharmacokinetic profile of FT-1518 base in mice. Table 31 summarizes PK parameters used in a pharmacokinetic profile with intravenous dose in mice and Table 32 summarizes PK parameters used in a pharmacokinetic profile with per oral dose in mice.

TABLE 31

PK parameters of a pharmacokinetic profile with intravenous dose in mice
IV dose (10 mg/kg)

| Parameter | Mean ± SD |
| --- | --- |
| $V_{ss}$ (L/kg) | 1.9 ± 0.4 |
| CI (L/h/kg) | 1.4 ± 0.5 |
| $T_{1/2}$(h) | 0.8 ± 0.07 |
| $AUC_0^{\infty}$ (ng · h/mL) | 7637 ± 2021 |

TABLE 32

PK parameters of a pharmacokinetic profile with per oral dose in mice
PO dose (50 mg/kg)

| Parameter | Mean ± SD |
|---|---|
| $T_{1/2}(h)$ | 4.6 ± 0.9 |
| $T_{max}(h)$ | 0.2 ± 0.0 |
| $C_{max}$ (ng/mL) | 8761 ± 718 |
| AU $C_0^{\infty}$ (ng · h/mL) | 25801 ± 404 |
| Bioavailability (% F) | 68 |

From FIG. 56 and tables 31 and 32, it can be seen that FT-1518 base showed high volume of distribution (>0.7 L/kg) and low clearance (~30% of mouse liver blood flow). The mean half life in intravenous study is about 0.8h and in per oral study about 0.46h. The study showed rapid absorption ($T_{max}$: 0.2h) and the bioavailability (68%) is moderate to high.

Figure 57:
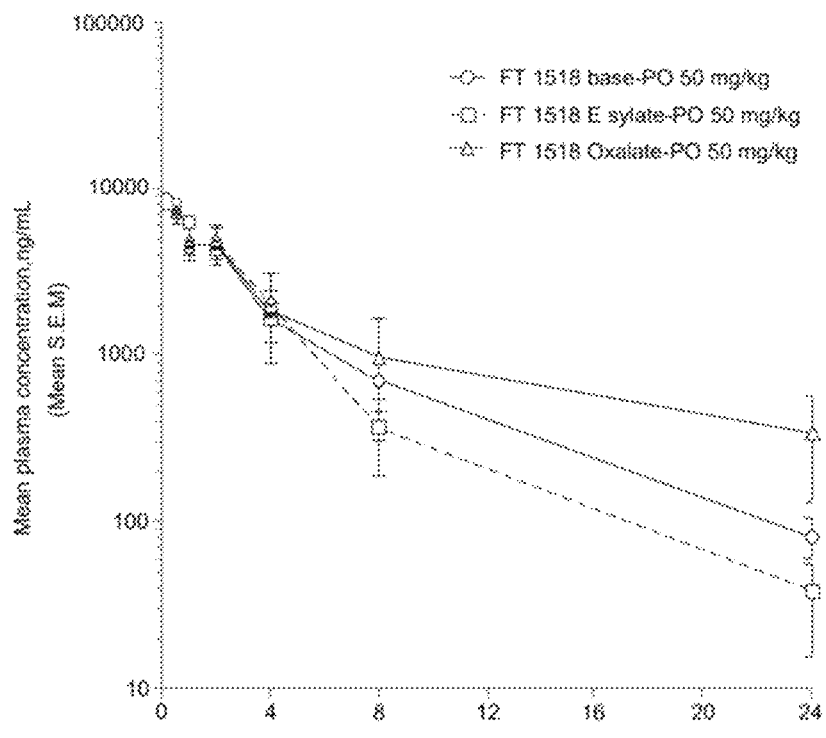
FIG. 57 compares pharmacokinetic parameters of FT-1518 base and salts in Balb/c male mice.

FIG. 57 shows a comparative pharmacokinetic study of FT-1518 base with the esylate and oxalate salts of FT-1518 Balb/c male mice. Table 33 compares PK parameters used in a pharmacokinetic profile of FT-1518 base with that of esylate and oxalate salts with per oral dose in Balb/c male mice.

TABLE 33

Comparison of PK parameters of a pharmacokinetic profile with per oral dose in Balb/c male mice.

| | Mean ± SD | | |
|---|---|---|---|
| PO dose (50 mg/kg) Parameter | FT-1518 base | FT-1518-Esylate | FT-1518-Oxalate |
| $T_{1/2}(h)$ | 4.6 ± 0.9 | 3.4 ± 1.2 | 3.5 ± 1.9 |
| $T_{max}(h)$ | 0.2 ± 0.0 | 0.3 ± 0.2 | 0.3 ± 0.2 |
| $C_{max}$ (ng/mL) | 8761 ± 718 | 8192 ± 891 | 8444 ± 1473 |
| AU $C_0^{\infty}$ (ng · h/mL) | 25801 ± 404 | 23745 ± 9249 | 28876 ± 7762 |
| Bioavailability (% F) | 68 | 62 | 76 |

FT-1518-oxalate salt showed high bioavailability in comparison to esylate salt and base.

Figure 58:
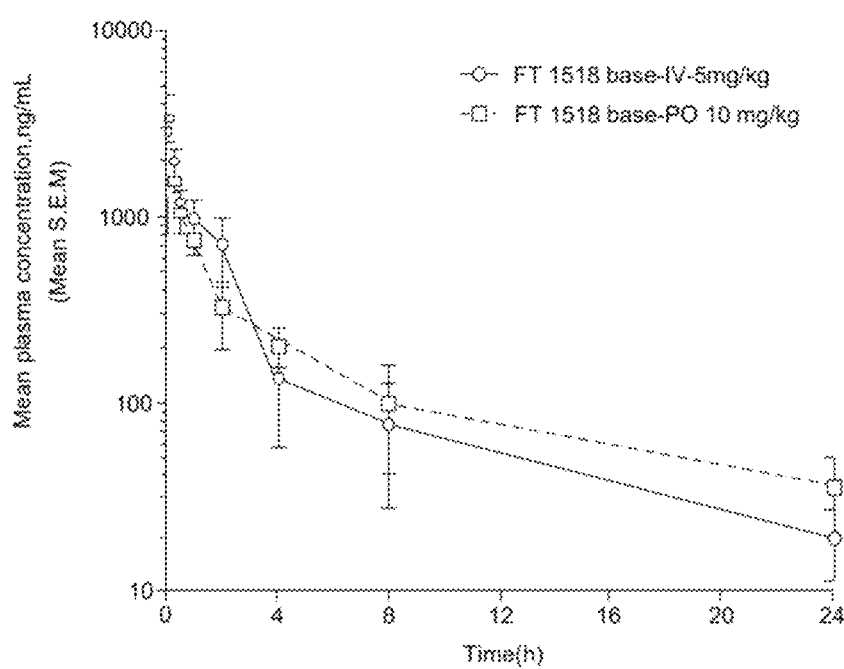
FIG. 58 compares pharmacokinetic parameters of FT-1518 base and salts in SD rats.

Intravenous and Per Oral Pharmacokinetic Profile of FT1518 (Base); FT1518-Esylate Salt and FT1518-Oxalate Salt in Male Sprague Dawley (SD) Rats
Species: SD rats
Gender: Male
Dose: IV (5 mg/kg), Single dose
  PO (10 mg/kg), single dose
Formulation:
  IV—DMSO:PEG400:Water (10:30:60 v/v)
  PO— 0.5% methylcellulose and 0.1% Tween 80 in water
Sampling Time Points:
  IV: 5 min, 15 min, 30 min, 1 h, 2, 4, 8 and 24 h post dose
  PO: 10 min, 15 min, 30 min, 1 h, 2, 4, 8 and 24 h post dose.
PK analysis: Phoenix software (Pharsight product). Non-compartmental Analysis (NCA) was used to estimate the PK parameters FIG. 58 shows a comparative pharmacokinetic study of FT-1518 base with the esylate and oxalate salts of FT-1518 in SD rats. Table 34 summarizes PK parameters used in a pharmacokinetic profile with intravenous dose in SD rats and Table 35 summarizes PK parameters used in a pharmacokinetic profile with per oral dose in SD rats.

TABLE 34

PK parameters of a pharmacokinetic profile with intravenous dose in SD rats
IV dose (5 mg/kg)

| Parameter | Mean ± SD |
|---|---|
| $V_{ss}$ (L/kg) | 3.0 ± 1.3 |
| CI (L/h/kg) | 1.4 ± 0.6 |
| $T_{1/2}(h)$ | 2.0 ± 1.3 |
| AU $C_0^{\infty}$ (ng · h/mL) | 3905 ± 1334 |

TABLE 35

PK parameters of a pharmacokinetic profile with per oral dose in SD rats Table 32.
PO dose (10 mg/kg)

| Parameter | Mean ± SD |
|---|---|
| $T_{1/2}(h)$ | 3.1 ± 2.4 |
| $T_{max}(h)$ | 0.5 ± 0.4 |
| $C_{max}$ (ng/ml) | 1592 ± 654 |
| AU $C_0^{\infty}$ (ng · h/mL) | 3422 ± 684 |
| Bioavailability (% F) | 44 |

From FIG. 58 and tables 34 and 35, it can be seen that FT-1518 base showed high volume of distribution (>0.7 L/kg) and moderate clearance (~42% of SD rat liver blood flow). The mean half life in intravenous study is about 2.0h and in per oral study about 3.1h. The study showed rapid absorption ($T_{max}$: 0.5h) and moderate bioavailability (44%).

All Compounds were tested at concentration of 3 μM (n = 3)

| | Invitro $T_{1/2}$ (min) | | |
|---|---|---|---|
| Compound | MLM | PHLM | RLM |
| FT1518-base | 43 | >60 | >60 |
| FT1618-Esylete | 24 | >60 | >60 |
| FT1518-Oxalate | 46 | >60 | >60 |

MLM: Mice liver microsomes;
PHLM: Pooled human liver microsomes;
RLM: Rat liver microsomes
✓ FT1518, FT 1518-Esylate and FT1518-Oxalate was highly stable in PHLM and RLM Plasma Protein Binding All Compounds were tested at concentration of 10 μM (n = 4)

| | % Bound | |
|---|---|---|
| Compound | Mouse plasma | Human Plasma |
| FT1518-Base | 91.52 | 97.32 |
| FT-1518-Esylate | 91.46 | 97.02 |
| FT1518-Oxalate | 91.79 | 95.54 |

✓ FT1518, FT1518-Esylate and FT1518-Oxalate showed moderate plasma protein binding in both mouse and human plasma

Caco-2 Permeability

| All Compounds were tested at concentration of 10 µM (n = 3) | | | |
|---|---|---|---|
| | Apparent permeability (Papp:nm/s) | | |
| Compound | A to B | B to A | Efflux ratio |
| FT1518-base | 215.71 ± 17.67 | 309.40 ± 4.28 | 1.4 |
| FT1518-Esylate | 215.91 ± 8.87 | 382.82 ± 4.26 | 1.8 |
| FT1518-Oxalate | 232.07 ± 18.01 | 292.03 ± 14.82 | 1.8 |

✓ FT1518 base, FT1518-Esylate and FT1518-Oxalate showed high permeability in Caco-2 assay. Efflux ratio of <2 indicates compounds that the compounds may not be substrates of P-gp or BCRP efflux transporters

| Anti-proliferative effects of FT1518 and salts in cancer cell lines | | |
|---|---|---|
| | $IC_{50}$ (nM) | |
| Compound | MDA-MB-231 | U-87 |
| FT1518-Base | >30000 | >10000 |
| FT-1518-Esytate | >10000 | >10000 |
| FT1518-Oxalate | >10000 | >10000 |

FT1518-base, FT1518-Esylate and FT1518-Oxalate showed an $IC_{50}$ value of >10000 nM in MDA-MB-231 (breast cancer) and U-87 (giloblastoma, epithelial)

Hepatic Clearance:

FT1518 esylate: FT1518 esylate showed high hepatic clearance in mouse and moderate in human, respectively; low in rat and dogs in terms of liver blood flow.

FT1518 oxalate: FT1518 oxalate showed moderate hepatic clearance in human, mouse and rat; low in dogs in terms of liver blood flow.

Pharmacokinetics in Rats:

A single dose administration of FT1518 is resulted in $C_{max}$ of 1592 ng/ml, AUC-3442 (ng·h/mL) and bioavailability of 44%.

FT1518 esylate: $C_{max}$ of 1768 ng/ml, AUC-9684 (ng·h/mL) and bioavailability of >100%.

FT1518 oxalate: $C_{max}$ of 1980 ng/ml, AUC-5288 (ng·h/mL) and bioavailability of 68%.

Ames Test:

Both base and salt forms are negative for genotoxicity in bacterial reverse mutation assay Acute Toxicity Study in Mice:

FT1518 and FT1518 esylate salt is well tolerated at 90 mg/kg in Balb/c mice.

In Vitro Assays:

FT 1518 base form showed IC50 of 246, 63 and 42 µM in breast cancer (MCF-7), colon carcinoma cancer (HCT-116) and prostate cancer (PC-3) lines, respectively.

FT 1518 esylate salt showed IC50 of 33, 64 and 67 µM in breast cancer (MCF-7), colon carcinoma cancer (HCT-116) and prostate cancer (PC-3) lines, respectively.

FT 1518 oxalate salt IC50 value of 183 µM in prostate cancer line.

Esylate Salt Single Crystal X-Ray Diffraction Analysis

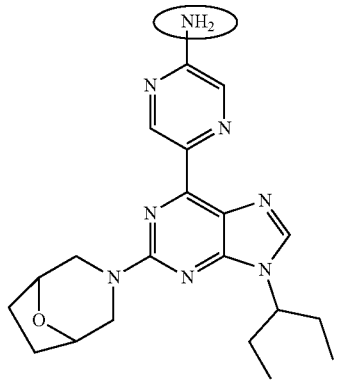 [SMILES: CCC(CC)n1cnc2c(-c3cnc(N)cn3)nc(N3CC4CCC(C3)O4)nc21]

Preliminary analysis was done by using microscope (Crystal quality) followed by cell check in Single Crystal X-ray Diffraction technique. From this analysis we find that crystal quality is not good (little fade), twinning due to this moderate diffraction is observed during cell check. Hence for this reason we collected data about 15 hours to establish the crystal structure coordinates.

The X-ray crystal structure of FS00067855-Esylate-salt was solved and refined in the monoclinic space group $P2_1/n$ with four molecules of esylate-salt and hydrate (Z'=1) in the asymmetric unit as 1:1:1 stoichiometric ratio. The esylate anion and FS00067855 cation associated through N—H . . . O ionic hydrogen interaction in the crystal lattice and water molecule incorporated in voids (FIG. 1 to FIG. 4)

FIG. 1: The FS00067855cation . . . esylate anion existed in the crystal lattice though N—H . . . O and extended in 1d lattice through N—H . . . O interaction.

Figure 2:
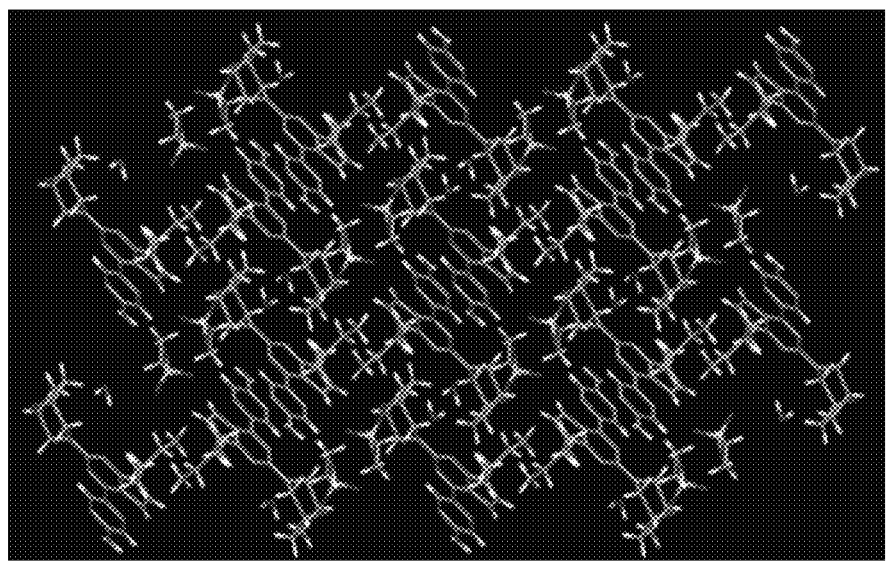
FIG. 2 depicts an illustrative example of water molecules incorporated in the crystal lattice of esylate salt crystal according to an embodiment.

FIG. 2: water molecules incorporated in the crystal lattice.

Figure 3:
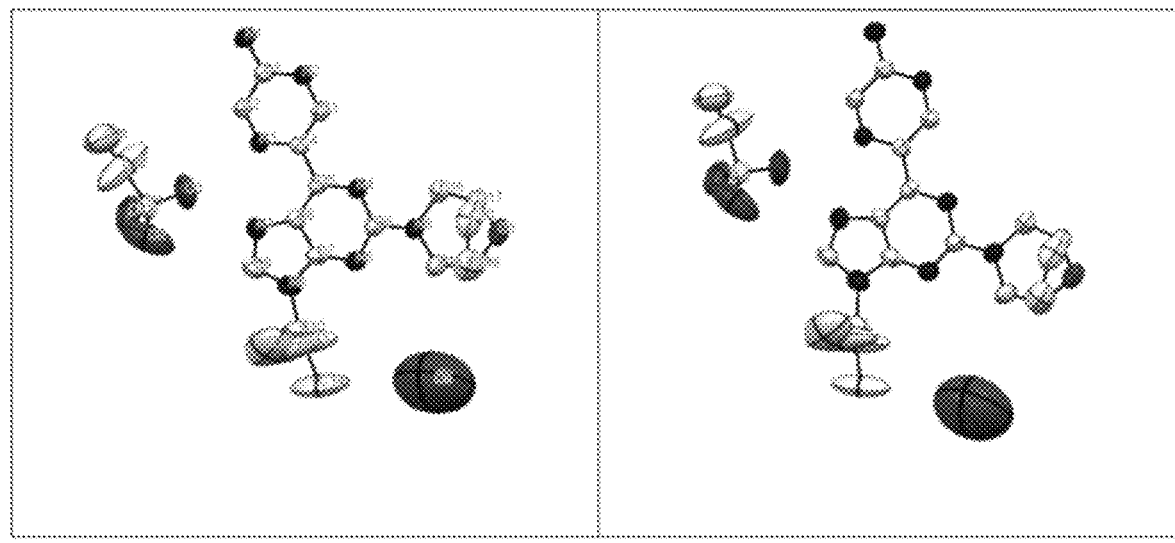
FIG. 3 depicts an ORTEP structures with hydrogens of esylate salt crystal according to an embodiment.

FIG. 3: ORTEP structures with hydrogens.

Figure 4:
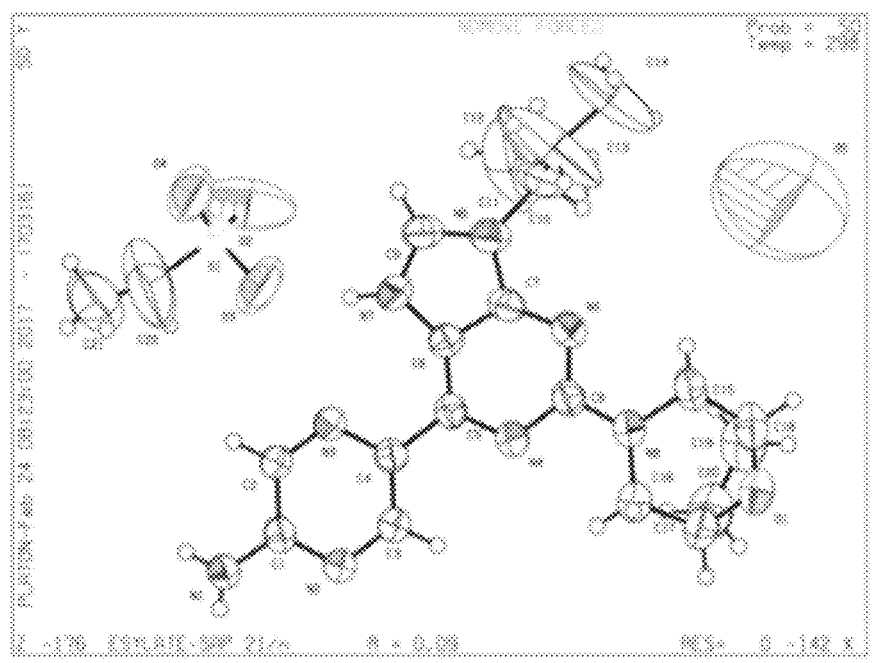
FIG. 4 depicts the structure refinement for esylate salt according to an embodiment.

FIG. 4: structure refinement for Esylate salt

| Crystal data and structure refinement for Esylate salt | |
|---|---|
| Identification code | Esylate salt |
| Empirical formula | C22 H34 N8 O5 S |
| Formula weight | 522.63 |
| Temperature | 298(2) K |
| Wavelength | 0.71073 Å |
| Crystal system | Monoclinic |
| Space group | P 21/n |
| Unit cell dimensions | a = 11.54(4) Å a = 90°. |
| | b = 11.33(3) Å b = 94.3(2)°. |
| | c = 19.98(7) Å g = 90°. |
| Volume | 2606(13) Å$^3$ |
| Z | 4 |
| Density (calculated) | 1.332 Mg/m$^3$ |
| Absorption coefficient | 0.173 mm$^{-1}$ |
| F(000) | 1112 |
| Crystal size | 0.36 × 0.24 × 0.12 mm$^3$ |
| Theta range for data collection | 1.976 to 25.493°. |
| Index ranges | −13 <= h <= 13, −13 <= k <= 13, −24 <= l <= 24 |
| Reflections collected | 39089 |
| Independent reflections | 4802 [R(int) = 0.0622] |
| Completeness to theta = 25.000° | 100.0% |
| Refinement method | Full-matrix least-squares on F$^2$ |
| Data/restraints/parameters | 4802/2/340 |
| Goodness-of-fit on F$^2$ | 1.066 |
| Final R indices [I >2 sigma(I)] | R1 = 0.0916, wR2 = 0.2493 |
| R indices (all data) | R1 = 0.1502, wR2 = 0.2963 |
| Extinction coefficient | n/a |
| Largest diff. peak and hole | 0.584 and −0.370 e.Å$^{-3}$ |

Datablock: ESYLATE-SALT Bond precision: C—C=0.0116 A Wavelength=0.71073 Cell: a=11.54(4) b=11.33(3) c=19.98(7) alpha=90 beta=94.3(2) gamma=90 Temperature: 298 K Calculated Reported Volume 2605(15) 2606(13) Space group P 21/n P 21/n Hall group -P 2yn -P 2yn Moiety formula C20 H27 N8 O, C2 H5 O3 S, H2 O? Sum formula C22 H34 N8 O5 S C22 H34 N8 O5 S Mr 522.63 522.63 Dx,g cm-3 1.333 1.332 Z 4 4 Mu (mm-1) 0.173 0.173 F000 1112.0 1112.0 F000' 1112.93 h,k,lmax 13,13,24 13,13,24 Nref 4842 4802 Tmin,Tmax 0.951, 0.979 Tmin' 0.940 Correction method=Not given Data completeness=0.992 Theta(max)=25.493 R (reflections)=0.0906 (2911) wR2(reflections)=0.2947(4802) S=1.060 Npar=345 The following ALERTS were generated. Each ALERT has the format test-name_ALERT_alert-type_alert-level. Click on the hyperlinks for more details of the test. Alert level A SHFSU01_ALERT_2_A The absolute value of parameter shift to su ratio >0.20 Absolute value of the parameter shift to su ratio given 0.250 Additional refinement cycles may be required. PLAT080_ALERT_2_A Maximum Shift/Error . . . 0.25 Why? PLAT245_ALERT_2_A U(iso) H5A Smaller than U(eq) O5 by . . . 0.670 AngSq PLAT245_ALERT_2_A U(iso) H5B Smaller than U(eq) O5 by . . . 0.698 AngSq PLAT360_ALERT_2_A Short C(sp3)-C(sp3) Bond C11-C12 . . . 1.20 Ang. PLAT410_ALERT_2_A Short Intra H . . . H Contact H10 . . . H11B . . . 1.76 Ang. PLAT417_ALERT_2_A Short Inter D-H . . . H-D H5A H5B . . . 1.30 Ang. PLAT417_ALERT_2_A Short Inter D-H . . . H-D H5B H5B . . . 1.13 Ang. Alert level B PLAT149_ALERT_3_B s.u. on the beta Angle is Too Large . . . 0.20 Degree PLAT234_ALERT_4_B Large Hirshfeld Difference C11-C12 . . . 0.26 Ang. PLAT241_ALERT_2_B High 'MainMol' Ueq as Compared to Neighbors of C11 Check PLAT241_ALERT_2_B High 'MainMol' Ueq as Compared to Neighbors of C13 Check PLAT242_ALERT_2_B Low 'MainMol' Ueq as Compared to Neighbors of C10 Check PLAT340_ALERT_3_B Low Bond Precision on C—C Bonds . . . 0.0116 Ang. PLAT360_ALERT_2_B Short C(sp3)-C(sp3) Bond C21-C22 . . . 1.26 Ang. Alert level C PLAT084_ALERT_3_C High wR2 Value (i.e. >0.25) . . . 0.29 Report PLAT148_ALERT_3_C s.u. on the a—Axis is (Too) Large . . . 0.040 Ang. PLAT148_ALERT_3_C s.u. on the b—Axis is (Too) Large . . . 0.0300 Ang. PLAT148_ALERT_3_C s.u. on the c—Axis is (Too) Large . . . 0.070 Ang. PLAT193_ALERT_1_C Cell and Diffraction Temperatures Differ by . . . 5 Degree PLAT213_ALERT_2_C Atom C11 has ADP max/min Ratio . . . 3.7 prolat PLAT213_ALERT_2_C Atom C13 has ADP max/min Ratio . . . 3.2 prolat PLAT220_ALERT_2_C Non-Solvent Resd 1 C Ucq(max)/Ucq(min) Range 6.0 Ratio PLAT222_ALERT_3_C Non-Solvent Resd 1 H Uiso(max)/Uiso(min) Range 5.4 Ratio PLAT241_ALERT_2_C High 'MainMol' Ueq as Compared to Neighbors of C20 Check PLAT243_ALERT_4_C High 'Solvent' Ueq as Compared to Neighbors of C22 Check PLAT244_ALERT_4_C Low 'Solvent' Ueq as Compared to Neighbors of 51 Check PLAT245_ALERT_2_C U(iso) H1B Smaller than U(eq) N1 by . . . 0.012 AngSq PLAT250_ALERT_2_C Large U3/U1 Ratio for Average U(i,j) Tensor . . . 2.1 Note PLAT352_ALERT_3_C Short N—H (X0.87,N1.01A) N1-H1B . . . 0.76 Ang. PLAT360_ALERT_2_C Short C(sp3)-C(sp3) Bond C10-C11 . . . 1.39 Ang. PLAT360_ALERT_2_C Short C(sp3)-C(sp3) Bond C10-C13 . . . 1.35 Ang. PLAT397_ALERT_2_C Deviating C—O—C Angle from 120 Deg for O1 101.6 Degree PLAT410_ALERT_2_C Short Intra H . . . H Contact H10 H13A . . . 1.97 Ang. PLAT413_ALERT_2_C Short Inter XH3 . . . XHn H12C . . . H14C . . . 2.14 Ang. PLAT417_ALERT_2_C Short Inter D-H . . . H-D H5A H5A . . . 2.12 Ang. Alert level G PLAT002_ALERT_2_G Number of Distance or Angle Restraints on AtSite 3 Note PLAT072_ALERT_2_G SHELXL First Parameter in WGHT Unusually Large 0.14 Report PLAT152_ALERT_1_G The Supplied and Calc. Volume s.u. Differ by . . . 2 Units PLAT172_ALERT_4_G The CIF-Embedded .res File Contains DFIX Records 2 Report PLAT199_ALERT_1_G Reported_cell_measurement_temperature . . . (K) 293 Check PLAT343_ALERT_2_G Unusual sp3 Angle Range in Main Residue for C10 Check PLAT343_ALERT_2_G Unusual sp3 Angle Range in Main Residue for C11 Check PLAT344_ALERT_2_G Unusual sp3 Angle Range in Solvent/Ion for. C22 Check PLAT793_ALERT_4_G The Model has Chirality at C17 (Centro SPGR) R Verify PLAT793_ALERT_4_G The Model has Chirality at C18 (Centro SPGR) S Verify PLAT860 ALERT_3_G Number of Least-Squares Restraints . . . 2 Note 8 ALERT level A=Most likely a serious problem—resolve or explain 7 ALERT level B=A potentially serious problem, consider carefully 21 ALERT level C=Check. Ensure it is not caused by an omission or oversight 11 ALERT level G=General information/check it is not something unexpected 3.

Oxalate Salt Single Crystal X-Ray Diffraction Analysis

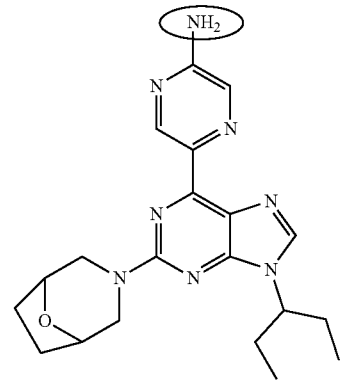 [SMILES: CCC(CC)n1cnc2c(-c3cnc(N)cn3)nc(N3CC4CCC(C3)O4)nc21]

Preliminary analysis was done by using microscope (Crystal quality) followed by cell check in Single Crystal X-ray Diffraction technique. From this analysis we find that crystal quality is good and moderate diffraction is observed. Hence further we collected data for 12 hours to establish the crystal structure coordinates.

The X-ray crystal structure of FS00067855-Oxalate-salt was solved and refined in the monoclinic space group $P2_1/n$ with four molecules of oxalate-salt and methanol solvate (Z'=1) in the asymmetric unit as 1:1:1 stoichiometric ratio. The mono-oxalate anion interacts with cation of FS00067855 through N—H . . . O ionic hydrogen bonds in a bifurcated $R_1^2(5)$ ring motif and methanol solvate is connected to oxalate anion through single point O—H . . . O interaction in the crystal lattice (FIG. 5 to FIG. 8).

Figure 5:
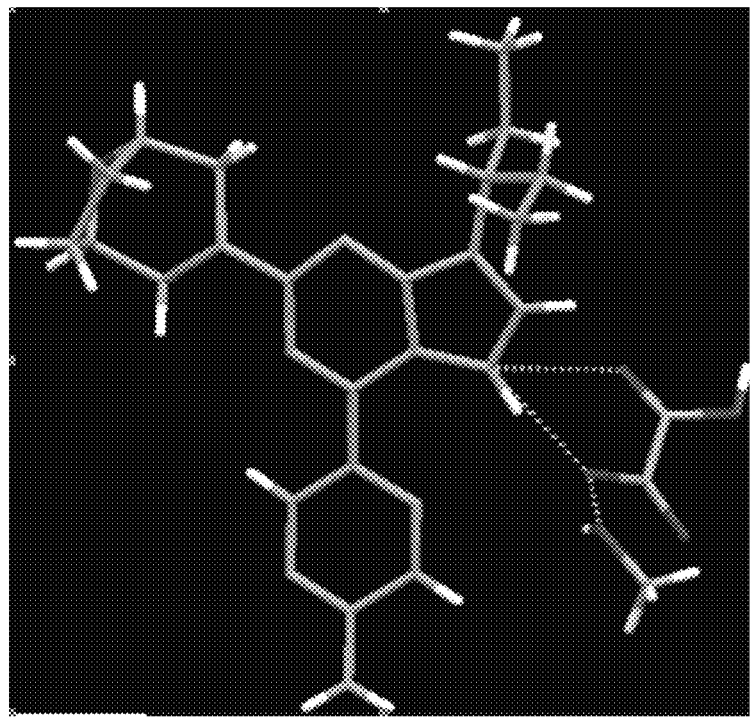
FIG. 5 depicts the FS00067855cation . . . oxalate anion and methanol solvate existed in the crystal lattice though N—H . . . O and O—H . . . O respectively according to an embodiment.

FIG. 5: The FS00067855cation . . . oxalate anion and methanol solvate existed in the crystal lattice though N—H . . . O and O—H . . . O respectively.

Figure 6:
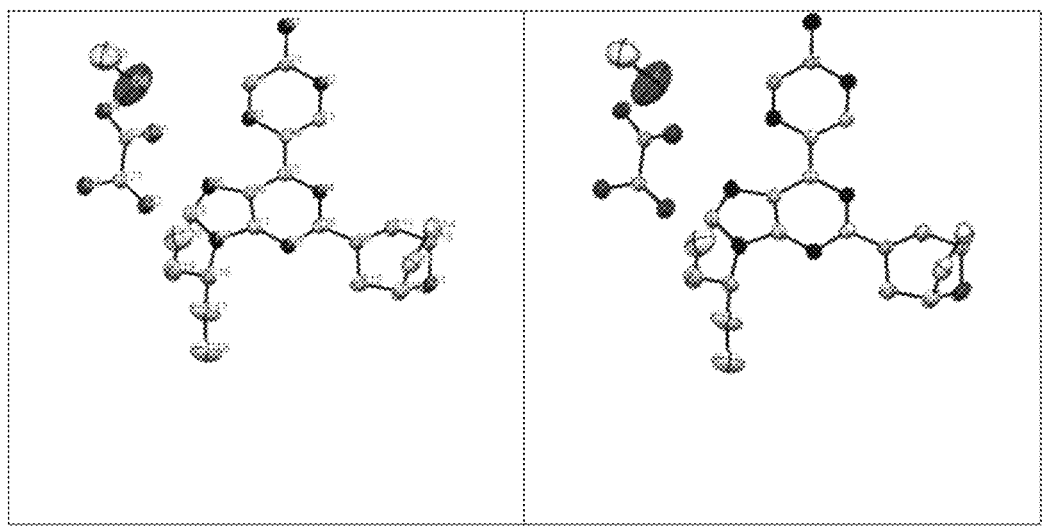
FIG. 6 depicts an illustrative example of ORTEP structures of Oxalate salt without hydrogens according to an embodiment.

FIG. 6: ORTEP structures of oxalate salt without hydrogens.

Figure 7:
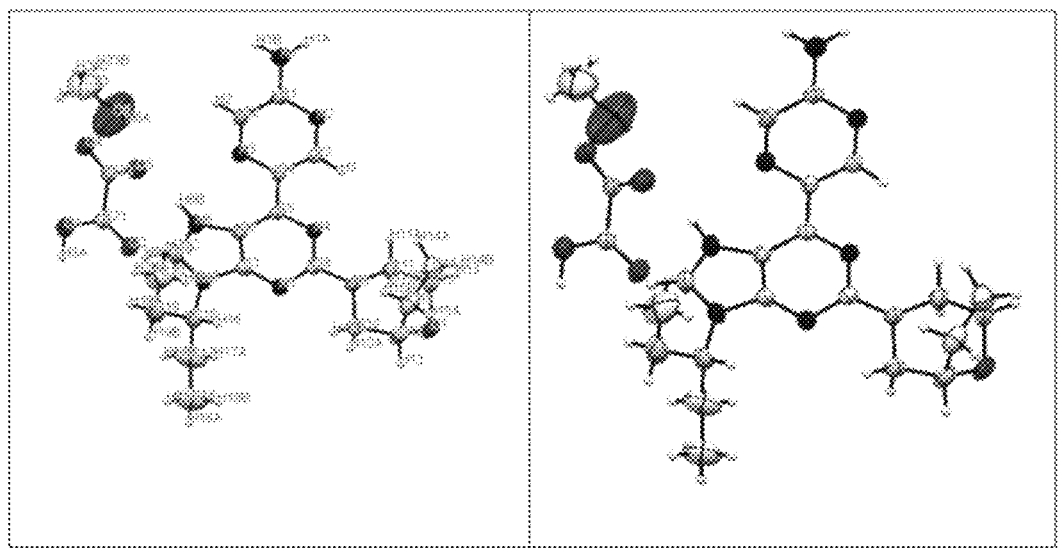
FIG. 7 depicts an ORTEP structures of Oxalate salt with hydrogens according to an embodiment.

FIG. 7: ORTEP structures of oxalate salt with hydrogens.

Figure 8:
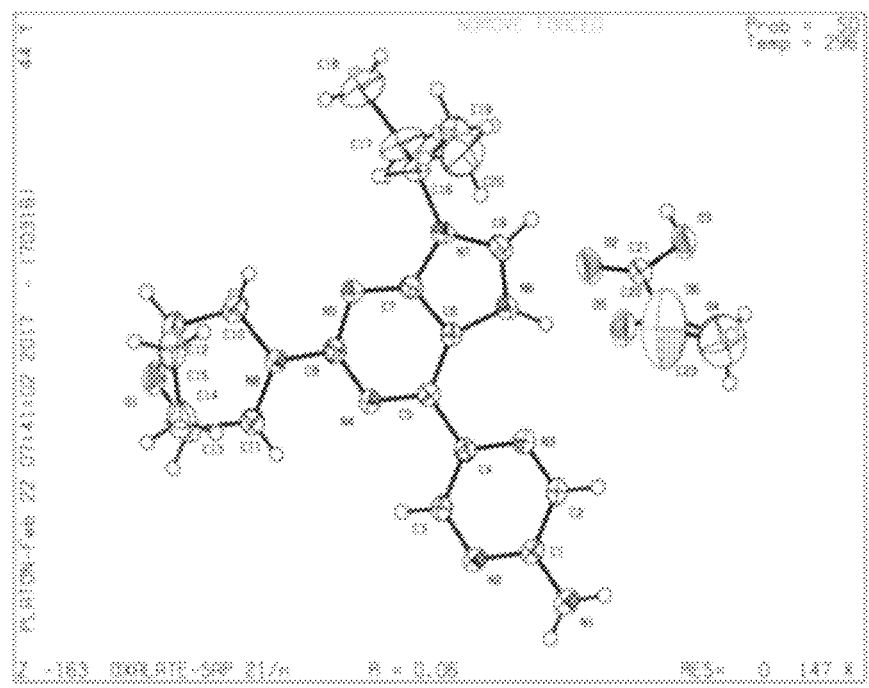
FIG. 8 depicts structure refinement for Oxalate salt according to an embodiment.

FIG. 8: Structure refinement of oxalate salt with hydrogens.

Crystal data and structure refinement for OXALATE SALT

| | |
|---|---|
| Identification code | OXALATE SALT |
| Empirical formula | C23 H32 N8 O6 |
| Formula weight | 516.56 |
| Temperature | 298(2) K |
| Wavelength | 0.71073 Å |
| Crystal system | Monoclinic |
| Space group | P 21/n |
| Unit cell dimensions | a = 12.9096(8) Å a= 90°. |
| | b = 10.3149(6) Å b = 94.023(3)°. |
| | c = 19.0837(11) Å g = 90°. |
| Volume | 2534.9(3) Å$^3$ |
| Z | 4 |
| Density (calculated) | 1.354 Mg/m$^3$ |
| Absorption coefficient | 0.100 mm$^{-1}$ |
| F(000) | 1096 |
| Crystal size | 0.24 × 0.15 × 0.10 mm$^3$ |
| Theta range for data collection | 2.140 to 25.447°. |
| Index ranges | −15 <= h <= 15, −12 <= k <= 12, |
| | −21 <= l <= 23 |
| Reflections collected | 39830 |
| Independent reflections | 4659 [R(int) = 0.0920] |
| Completeness to theta =25.242° | 99.9% |
| Refinement method | Full-matrix least-squares on F$^2$ |
| Data/restraints/parameters | 4659/1/352 |
| Goodness-of-fit on F$^2$ | 1.028 |
| Final R indices [I >2 sigma(I)] | R1 = 0.0627, wR2 = 0.1248 |
| R indices (all data) | R1 = 0.1230, wR2 = 0.1520 |
| Extinction coefficient | n/a |

Largest duff. peak and hole 0.358 and −0.40 Merely for illustration, only representative number/type of graph, chart, block and sub-block diagrams were shown. Many environments often contain many more block and sub-block diagrams or systems and sub-systems, both in number and type, depending on the purpose for which the environment is designed.

Datablock: OXALATE-SALT Bond precision: C—C=0.0046 A Wavelength=0.71073 Cell: a=12.9096(8) b=10.3149(6) c=19.0837(11) alpha=90 beta=94.023 (3) gamma=90 Temperature: 296 K Calculated Reported Volume 2535.0(3) 2534.9(3) Space group P 21/n P 21/n Hall group -P 2yn -P 2yn Moiety formula C20 H27 N8 O, C2 H O4, C H4 O? Sum formula C23 H32 N8 O6 C23 H32 N8 O6 Mr 516.57 516.56 Dx,g cm-3 1.354 1.354 Z 4 4 Mu (mm-1) 0.100 0.100 F000 1096.0 1096.0 F000' 1096.49 h,k,lmax 15,12,23 15,12,23 Nref 4691 4659 Tmin,Tmax 0.982, 0.990 Tmin' 0.976 Correction method=Not given Data completeness=0.993 Theta(max)=25.447 R (reflections)=0.0627 (2805) wR2(reflections)=0.1520(4659) S=1.028 Npar=352 The following ALERTS were generated. Each ALERT has the format test-name_ALERT_alert-type_alert-level. Click on the hyperlinks for more details of the test. Alert level C PLAT052_ALERT_1_C Info on Absorption Correction Method Not Given Please Do ! PLAT193_ALERT_1_C Cell and Diffraction Temperatures Differ by . . . 2 Degree PLAT220_ALERT_2_C Non-Solvent Resd 1 C Ueq(max)/Ueq(min) Range 3.3 Ratio PLAT242_ALERT_2_C Low 'MainMol' Ueq as Compared to Neighbors of C16 Check PLAT250_ALERT_2_C Large U3/U1 Ratio for Average U(i,j) Tensor . . . 2.3 Note PLAT340_ALERT_3_C Low Bond Precision on C—C Bonds . . . 0.0046 Ang. PLAT397_ALERT_2_C Deviating C—O—C Angle from 120 Deg for O1 101.5 Degree Alert level G PLAT002_ALERT_2_G Number of Distance or Angle Restraints on AtSite 2 Note PLAT007_ALERT_5_G Number of Unrefined Donor-H Atoms . . . 1 Report PLAT172_ALERT_4_G The CIF-Embedded .res File Contains DFIX Records 1 Report PLAT793_ALERT_4_G The Model has Chirality at C12 (Centro SPGR) S Verify PLAT793_ALERT_4_G The Model has Chirality at C13 (Centro SPGR) R Verify PLAT860_ALERT_3_G Number of Least-Squares Restraints . . . 1 Note 0 ALERT level A=Most likely a serious problem—resolve or explain 0 ALERT level B=A potentially serious problem, consider carefully 7 ALERT level C=Check. Ensure it is not caused by an omission or oversight 6 ALERT level G=General information/check it is not something unexpected 2 ALERT type 1 CIF construction/syntax error, inconsistent or missing data 5 ALERT type 2 Indicator that the structure model may be wrong or deficient 2 ALERT type 3 Indicator that the structure quality may be low 3 ALERT type 4 Improvement, methodology, query or suggestion 1 ALERT type 5.

While specific embodiments of the invention have been shown and described in detail to illustrate the inventive principles, it will be understood that the invention may be embodied otherwise without departing from such principles.

Reference throughout this specification to "one embodiment", "an embodiment", or similar language means that a particular feature, structure, or characteristic described in connection with the embodiment is included in at least one embodiment of the present invention. Thus, appearances of the phrases "in one embodiment", "in an embodiment" and similar language throughout this specification may, but do not necessarily, all refer to the same embodiment.

This disclosure is not limited to the particular systems, devices and methods described, as these may vary. The terminology used in the description is for the purpose of describing the particular versions or embodiments only, and is not intended to limit the scope.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

As will be understood by one skilled in the art, for any and all purposes, such as in terms of providing a written description, all ranges disclosed herein also encompass any and all possible subranges and combinations of subranges thereof.

What is claimed is:

1. A pharmaceutically acceptable esylate or oxalate salt of 5-[2-(8-oxa-3-azabicyclo[3.2.1]octan-3-yl)-9-pentan-3-yl-purin-6-yl]pyrazin-2-amine (also referred as FT 1518), wherein the esylate or the oxalate salt of 5-[2-(8 oxa-3-azabicyclo[3.2.1]octan-3-yl)-9-pentan-3-ylpurin-6-yl] pyrazin-2-amine has a bioavailability at least 20% greater than the bioavailability of the FT 1518 in a subject.

2. A method for preparing a pharmaceutically acceptable esylate or oxalate salt of 5-[2-(8-oxa-3-azabicyclo[3.2.1] octan-3-yl)-9-pentan-3-ylpurin-6-yl]pyrazin-2-amine comprising precipitating the esylate from a solvent of tetrahydrofuran or precipitating the oxalate by slow evaporation from acetone, wherein the esylate or the oxalate salt is crystalline in nature.

3. The method as claimed in claim 2, wherein acidic counter-ion for the oxalate salt of 5-[2-(8-oxa-3-azabicyclo[3.2.1]octan-3-yl)-9-pentan-3-ylpurin-6-yl]pyrazin-2-amine is oxalic acid anhydrous with pKa value comprising 1.25 and 4.23, wherein the acidic counter-ion for the esylate salt of 5-[2-(8-oxa-3-azabicyclo[3.2.1]octan-3-yl)-9-pentan-3-ylpurin-6-yl]pyrazin-2-amine is ethane sulfonic acid with the pKa value comprising 1.68.

4. The method as claimed in claim 3, wherein a ratio of the FT 1518 to the counter-ion is 1:1.125.

5. The method as claimed in claim 2, further comprising screening of the pharmaceutically acceptable esylate or oxalate salt, wherein the formation of the esylate salt or the oxalate salt is confirmed by performing solubility study in 10 mM potassium dihydrogen phosphate buffer (pH 6.8), % purity study by high-performance liquid chromatography, crystallinity study by powder X-ray diffraction, structure elucidation by proton NMR, hygroscopicity and pseudo-polymorph-propensity study by dynamic vapour sorption, melting point & thermal events study by differential scanning calorimetry, % weight loss study before melting point maximum up to 150° C. by thermogravimetric analysis.

6. The method as claimed in claim 2, further comprising selection and structural elucidation of the pharmaceutically acceptable salt of 5-[2-(8-oxa-3-azabicyclo[3.2.1]octan-3-yl)-9-pentan-3-ylpurin-6-yl]pyrazin-2-amine (FT1518 base), wherein the selection is based on the stability studies of various physical forms of the salts by crystallization processes from a solvent system of ethylacetate:water in 9:1 ratio for the esylate salt and the oxalate salt of FT-1518, Form-1 of the esylate salt and form-A of the oxalate salt, wherein structural elucidation is based on the single crystal analysis of the salts.

7. The pharmaceutically acceptable esylate or oxalate salt as claimed in claim 1, wherein the salt forms have stability in human, rat, mice and dog microsomes.

8. The pharmaceutically acceptable esylate or oxalate salt as claimed in claim 1, wherein the FT 1518 esylate salt shows IC50 value of 33 µM in breast cancer (MCF-7) lines, 64 µM in colon cancer (HCT-116) lines, and 67 µM in prostate cancer (PC-3) lines respectively; wherein the FT 1518 oxalate salt shows IC50 value of 183 µM in prostate cancer lines.

9. The pharmaceutically acceptable esylate or oxalate salt as claimed in claim 1, wherein a single dose administration of the FT 1518-esylate results at a $C_{max}$ of 1768 ng/ml, AUC-9684 (ng·h/mL) with a bioavailability of >100%, and a single dose administration of the FT 1518-oxalate results at a $C_{max}$ of 1980 ng/ml, AUC-5288 (ng·h/mL) with a bioavailability of 68% in rats compared with a single dose administration of the FT1518 resulted at a $C_{max}$ of 1592 ng/ml, AUC-3442 (ng·h/mL) with a bioavailability of 44%.

10. The pharmaceutically acceptable esylate or oxalate salt as claimed in claim 1, wherein the esylate salt has a bioavailability at least 56% greater than the bioavailability of the FT 1518 in the subject.

11. The pharmaceutically acceptable esylate or oxalate salt as claimed in claim 1, wherein a single dose administration of the esylate salt or the oxalate salt has a bioavailability at least 20% greater than the bioavailability of the FT 1518 in the subject.

12. The pharmaceutically acceptable esylate or oxalate salt as claimed in claim 11, wherein a single dose administration of the esylate salt has a bioavailability at least 56% greater than the bioavailability of the FT 1518 in the subject.

* * * * *